US008399647B2

(12) United States Patent
Bender et al.

(10) Patent No.: US 8,399,647 B2
(45) Date of Patent: Mar. 19, 2013

(54) ALPHA5-BETA1 ANTIBODIES AND THEIR USES

(75) Inventors: Steven L. Bender, Oceanside, CA (US); Gerald F. Casperson, Ballwin, MO (US); Dana D. Hu-Lowe, Encinitas, CA (US); Xin Jiang, San Diego, CA (US); Gang Li, San Diego, CA (US); Michael A. North, Rancho Santa Fe, CA (US); Jianying Wang, San Diego, CA (US); Grant Wickman, Glasgow (GB); Peter Brams, Sacramento, CA (US); Haichun Huang, Fremont, CA (US); Brigitte Devaux, Palo Alto, CA (US); Haibin Chen, Sunnyvale, CA (US); Dawn M. Tanamachi, Miltpitas, CA (US); Kristopher Toy, San Jose, CA (US); Lan Yang, Morgan Hill, CA (US); Tim W. Sproul, Livermore, CA (US); Mark Yamanaka, Pleasanton, CA (US)

(73) Assignees: Pfizer Inc., New York, NY (US); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/237,502

(22) Filed: Sep. 20, 2011

(65) Prior Publication Data
US 2012/0009622 A1 Jan. 12, 2012

Related U.S. Application Data

(63) Continuation of application No. 12/365,638, filed on Feb. 4, 2009, now Pat. No. 8,039,596.

(60) Provisional application No. 61/026,207, filed on Feb. 5, 2008, provisional application No. 61/095,429, filed on Sep. 9, 2008.

(51) Int. Cl.
*C07H 21/04* (2006.01)
*C12P 21/06* (2006.01)
*C12N 15/87* (2006.01)
*C12N 1/20* (2006.01)
*C12N 15/74* (2006.01)

(52) U.S. Cl. ............... 536/23.53; 435/69.1; 435/455; 435/252.3; 435/320.1

(58) Field of Classification Search ............ None
See application file for complete search history.

(56) References Cited

U.S. PATENT DOCUMENTS

| 5,262,520 | A | 11/1993 | Plow et al. |
| 5,500,362 | A | 3/1996 | Robinson et al. |
| 5,821,337 | A | 10/1998 | Carter et al. |
| 6,242,577 | B1 | 6/2001 | Ruoslahti et al. |
| 6,737,056 | B1 | 5/2004 | Presta |
| 6,852,318 | B1 | 2/2005 | Varner |
| 7,276,589 | B2 | 10/2007 | Ramakrishnan et al. |
| 2003/0103978 | A1 | 6/2003 | Deshpande et al. |
| 2005/0069869 | A1 | 3/2005 | Ambrosino et al. |
| 2005/0260210 | A1 | 11/2005 | Ramakrishnan et al. |
| 2006/0008415 | A1 | 1/2006 | Kaisheva et al. |
| 2006/0040325 | A1 | 2/2006 | Wu et al. |
| 2007/0275460 | A1 | 11/2007 | Desjarlais et al. |
| 2009/0081207 | A1 | 3/2009 | Menrad et al. |

FOREIGN PATENT DOCUMENTS

| WO | WO-00/42072 | 4/2000 |
| WO | WO-01/04157 | 1/2001 |
| WO | WO-2004/056308 | 7/2004 |
| WO | WO-2004/089988 | 10/2004 |
| WO | WO-2005/056713 | 6/2005 |
| WO | WO-2005/092073 | 10/2005 |
| WO | WO-2005/103081 | 11/2005 |
| WO | WO-2005/123780 | 12/2005 |
| WO | WO-2007/134876 | 11/2007 |
| WO | WO-2008/060645 | 5/2008 |

OTHER PUBLICATIONS

Adams et al, "Monoclonal Antibody Therapy of Cancer," *Nature Biology*, 2005, 1147-1157, vol. 23, No. 9.
Clynes et al., "Fc Receptors are Required in Passive and Active Immunity to Melanoma," *Proc. Natl. Acad. Sci. USA*, 1998, 652-656, vol. 95.
Danen et al., "Emergence of α5β1 Fibronectin- and αvβ3 Vitronectin-Receptor Expression in Melanocytic Tumour Progression," *Histopathlogy*, 1994, 249-256.
Drake et al., "Antibodies to β$_1$-Integrins Cause Alterations of Aortic Vasculogenesis, In Vivo," *Developmental Dynamics*, 1992, 83-91, vol. 193.
Enaida et all;, "Effect of Growth Factors on Expression of Integrin Subtypes in Microvascular Endothelial Cells Isolated from Bovine Reintas," *Fukushima J. Med. Sci.*, 1998, 43-52, vol. 44, No. 1.
Jin et al., "Integrins: Roles in Cancer Development and as Treatment Targets," *British Journal of Cancer*, 2004, 561-565, vol. 90.
Kim et al., "Regulation of Angiogenesis In Vivo by Ligation of Integrin α5β11 with the Central Cell-Binding Domain of Fibronectin," *American Journal of Pathology*, 2000, 1345-1362, vol. 156, No. 4.
Klein et al., "Basic Fibroblast Growth Factor Modulates Integrin Expression in Microvascular Endothelial Cells," *Molecular Biology of the Cell*, 1993, 973-982, vol. 4.
Mousa et al., "Role of Hypoxia and Extracellular Matrix-Integrin Binding in the Modulation of Angiiogenic Growth Factors Secretion by Retinal Pigmented Epithelial Cells," *Journal of Cellular Biochemistry*, 1999, 135-143, vol. 74.

(Continued)

*Primary Examiner* — Maher Haddad
(74) *Attorney, Agent, or Firm* — Dickstein Shapiro LLP

(57) ABSTRACT

The present disclosure provides isolated monoclonal antibodies, particularly human monoclonal antibodies, or antigen binding portions thereof, that specifically bind to integrin α5β1 with high affinity. Nucleic acid molecules encoding the antibodies of the disclosure, expression vectors, host cells and methods for expressing the antibodies of the disclosure are also provided. Immunoconjugates, bispecific molecules and pharmaceutical compositions comprising the antibodies or antigen binding portions thereof are also provided. The disclosure also provides methods for treating various cancers using the anti-α5β1 antibodies or antigen binding portions thereof described herein.

8 Claims, 23 Drawing Sheets

OTHER PUBLICATIONS

Muschler et al., "Down-regulation of the Chicken $\alpha_5\beta_1$ Integrin Fibronectin Receptor During Development," *Development*, 1991, 327-337, vol. 113.

Newton et al., "Inhibition of Experimental Metastasis of Human Breast Carcinoma Cells in Athymic Nude Mice by anti-$\alpha_5\beta_1$ Fibronectin Receptor Integrin Antibodies," *International Journal of Oncology*, 1995, 1063-1070, vol. 6.

Presotto et al., "A Novel Muscle Protein Located Inside the Terminal Cisternae of the Sarcoplasmic Reticulum," *The Journal of Biological Chemistry*, 1997, 6534-6538, vol. 272, No. 10.

Ramakrishnan et al., "Preclinical Evaluation of an Anti-Alpha5beta Integrin Antibody as a Novel Anit-Angiogenic Agent," *Journal of Experimental Therapeutics and Oncology*, Rapid Science Publishers, London, GB, vol. 5 May 4, 2006, pp. 273-286.

Ravetch et al. "Fc Receptors," *Annu. Rev. Immunol.*, 1991, 457-492.

Shields et al., "High Resolution Mapping of the Binding Site on Human IgG1 for FcγRI, FcγRII, FcγRIII, and FcRn and Design of IgG1 Variants with Improved Binding to the FcγR," *The Journal of Biological Chemistry*, 2001, 6591-6604, vol. 276, No. 9.

Shinohara et al., "Expression of Integrins in Squamous Cell Carcinoma of the Oral Cavity," *American Journal of Clinical Pathology*, 1999, 75-88, vol. 111.

Takagi et al., Structure of Integrin $\alpha_5\beta_1$ in Complex with Fibronectin, *The EMBO Journal*, 2003, 4607-4615, vol. 22, No. 18.

Treon et al., "Polymorphisms in FcγRIIIA (CD16) Receptor Expression are Associated with Clinical Response to Rituximab in Waldenström's Macroglobulinemia," *Journal of Clinical Oncology*, 2005, 474-481, vol. 23, No. 3.

Trikha et al., "CNTO 95, A Fully Human Monocolonal Antibody that Inhibits αv Integrins, Has Antitumor and Antiangiogenic Acticity In Vivo," *Int. J. Cancer*, 2004, 326-335, vol. 110.

Uchida et al., "The Innate Mononuclear Phagocyte Network Depletes B Lymphocytes Through Fc Receptor Development Mechanisms During Anti-CD20 Antibody Immunotherapy," *The Journal of Experimental Medicine*, 2004, 1659-1669, vol. 199, No. 12.

Yao et al., "Expression of the Integrin $\alpha_5$ Subunit and its Mediated Cell Adhesion in Hepatocellular Carcinoma," *J. Cancer Res. Clin. Oncology*, 1997, 435-440, vol. 123.

International Search Report dated Jun. 22, 2009.

CAGCTGCAGCTGCAGGAGTCGGGCCCAGGACTGGTGAAGCCTTCGGAGAC
CCTGTCCCTCACCTGCACTGTCTCTGGTGGCTCCATCAGCAGTAGTAGCT
ACTGGGGCTGGATCCGCCAGCCCCCAGGGAAGGGGCTGGAGTGGATTGGG
AGTATCTACTATAGTGGGAGAAACTACAACAACCCGTCCCTCAAGAGTCG
AGTCACCATATCCGTAGACACGTCCAAGAACCAGTTCTCCCTGAAGCTGA
GCTCTGTGACCGCCGCAGACACGGCTGTGTATTACTGTGCGAGACATTAC
TATGGTTCGGGGAGTTCCTACTACTACGATCTGGACGTCTGGGGCCA
AGGGACCACGGTCACCGTCTCCTCA

Figure 1A: DNA sequence of 22B5 heavy chain variable region

QLQLQESGPGLVKPSETLSLTCTVSGGSISSSSYWGWIRQPPGKGLEWIGSIYYSG
RNYNNPSLKSRVTISVDTSKNQFSLKLSSVTAADTAVYYCARHYYGSGSSYYYY
DLDVWGQGTTVTVSS

Figure 1B: Amino acid sequence of 22B5 heavy chain variable region

GAAATTGTGTTGACACAGTCTCCAGCCACCCTGTCTTTGTCTCCAGGGGA
AAGAGCCACCCTCTCCTGCAGGGCCAGTCAGAGTGTTAGCAGCTACTTAG
CCTGGTACCAACAGAAACCTGGCCAGGCTCCCAGGCTCCTCATCTATGAT
GCATCCAACAGGGCCACTGGCATCCCAGCCAGGTTCAGTGGCAGTGGGTC
TGGGACAGACTTCACTCTCACCATCAGCAGCCTAGAGCCTGAAGATTTTG
CAGTTTATTACTGTCAGCAGCGTAGCAACTGGCCTCTCACTTTCGGCGGA
GGGACCAAGGTGGAGATCAAA

Figure 1C: DNA sequence of 22B5 light chain variable region

EIVLTQSPATLSLSPGERATLSCRASQSVSSYLAWYQQKPGQAPRLLIYDASNRA
TGIPARFSGSGSGTDFTLTISSLEPEDFAVYYCQQRSNWPLTFGGGTKVEIK

Figure 1D: Amino acid sequence of 22B5 light chain variable region

CAGGTGCAGTTGGTGGAGTCTGGGGGAGGCGTGGTCCAGCCTGGGAGGTCCC
TGAGACTCTCCTGTGCAGCCTCTGGATTCACCTTCAGT<u>AGTTATGCTATGCAC</u>
TGGGTCCGCCAGGCTCCAGGCAAGGGGCTGGAGTGGGTGGCA<u>GTTATATCAT
TTGATGGAAGCAATAAAAACTACGCAGACTCCGTGAAGGGC</u>CGATTCACCAT
CTCCAGAGACAATTCCAAGAACACGCTGTATCTGCAAATGAACAGCCTGAGA
GCTGAGGACACGGCTATGTATTACTGTGCGAGA<u>GAATACTGGGGAACCTACT
ACTACGGTATGGACGTC</u>TGGGGCCAAGGGACCACGGTCACCGTCTCCTCA

Figure 1E: DNA sequence of 24C7 heavy chain variable region

QVQLVESGGGVVQPGRSLRLSCAASGFTFSS<u>YAMH</u>WVRQAPGKGLEWVA<u>VISF
DGSNKNYADSVKG</u>RFTISRDNSKNTLYLQMNSLRAEDTAMYYCAR<u>EYWGTYY
YGMDV</u>WGQGTTVTVSS

Figure 1F: Amino acid sequence of 24C7 heavy chain variable region

GAAATTGTGTTGACACAGTCTCCAGCCACCCTGTCTTTGTCTCCAGGGGAAAG
AGCCACCCTCTCCTGC<u>AGGGCCAGTCAGAGTGTTAGCAACTACTTAGCCTGG</u>
TACCAACAGAAACCTGGCCAGGCTCCCAGGCTCCTCATCTAT<u>GATGCATCCA
ACAGGGCCACT</u>GGCATCCCAGCCAGGTTCAGTGGCAGTGGGTCTGGGACAGA
CTTCACTCTCACCATCAGCAGCCTAGAGCCTGAAGATTTTGCAGTTTATTACT
GT<u>CAGCAGCGTACCAACTGGCCGTACACT</u>TTTGGCCAGGGGACCAAGCTGGA
GATCAAA

Figure 1G: DNA sequence of 24C7 light chain variable region

EIVLTQSPATLSLSPGERATLSC<u>RASQSVSNYLA</u>WYQQKPGQAPRLLIY<u>DASNRA
T</u>GIPARFSGSGSGTDFTLTISSLEPEDFAVYYC<u>QQRTNWPYT</u>FGQGTKLEIK

Figure 1H: Amino acid sequence of 24C7 light chain variable region

CAGGTGCAGCTGGTGGAGTCTGGGGGAGGCGTGGTCCAGCCTGGGAGGTCCC
TGAGACTCTCCTGTGCAGCCTCTGGATTCCCCTTC<u>AGTACCTATGCTATGCAC</u>
TGGGTCCGCCAGGCTCCAGGCAAGGGGCTGGAGTGGGTGGCA<u>GTTATATCAT
ATGATGGAAGCAATAAATACTACGCAGACTCCGTGAAGGGC</u>CGATTCACCAT
CTCCAGAGACAATTCCAAGAACACGCTGTATCTGCAAATGAACAGCCTGAGA
GCTGAGGACACGGCTGTGTATTACTGTGCG<u>AGAGAGTCCCCCCCCATCTACT
ACTACTACGGTATGGACGT</u>CTGGGGCCAAGGGACCACGGTCACCGTCTCCTC
A

Figure 1I: DNA sequence of 1D9 heavy chain variable region

QVQLVESGGGVVQPGRSLRLSCAASGFPF<u>STYAMH</u>WVRQAPGKGLEWVA<u>VISY
DGSNKYYADSVKG</u>RFTISRDNSKNTLYLQMNSLRAEDTAVYYCA<u>RESPPIYYYY
GMDV</u>WGQGTTVTVSS

Figure 1J: Amino acid sequence of 1D9 heavy chain variable region

GAAATTGTGTTGACACAGTCTCCAGCCACCCTGTCTTTGTCTCCAGGGGAAAG
AGCCACCCTCTCCTGC<u>AGGGCCAGTCAGAGTGTTAGCAGCTACTTAGCC</u>TGG
TACCAACAGAAACCTGGCCAGGCTCCCAGGCTCCTCATCTAT<u>GATGCATCCA</u>
<u>ACAGGGCC</u>ACTGGCATCCCAGCCAGGTTCAGTGGCAGTGGGTCTGGGACAGA
CTTCACTCTCACCATCAGCAGCCTAGAGCCTGAAGATTTTGCAGTTTATTACT
GT<u>CAGCAGCGTAGCAACTGGCCTCGGACG</u>TTCGGCCAAGGGACCAAGGTGG
AAATCAAA

Figure 1K: DNA sequence of 1D9 light chain variable region

EIVLTQSPATLSLSPGERATLSC<u>RASQSVSSYLA</u>WYQQKPGQAPRLLIY<u>DASNRA</u>
<u>T</u>GIPARFSGSGSGTDFTLTISSLEPEDFAVYYC<u>QQRSNWPRT</u>FGQGTKVEIK

Figure 1L: Amino acid sequence of 1D9 light chain variable region

CAGGTGCAACTGGTGGAGTCTGGGGGAGGCGTGGTCCAGCCTGGGAGGTCCC
TGAGACTCTCCTGTGCAGCCTCTGGATTCACCTTCAGT<u>AGCTATGCTATGCAC</u>
TGGGTCCGCCAGGCTCCAGGCAAGGGGCTGGAGTGGGTGGC<u>AGTTATATCAT
TTGATGGAAGCACTAAATACTACGCAGACTCCGTGAAGGGC</u>CGATTCACCAT
CTCCAGAGACAATTCCAAGAACACGCTGGATCTGCAAATGAACAGCCTGAGA
GCTGAGGACACGGCTCTGTATTACTGTGCGAGA<u>GAATACTGGGGAACCTACT
ACTACGGGACGGACGT</u>CTGGGGCCAAGGGACCACGGTCATCGTCTCCTCA

Figure 1M: DNA sequence of 2D2 heavy chain variable region

QVQLVESGGGVVQPGRSLRLSCAASGFTFS<u>SYAMH</u>WVRQAPGKGLEWVA<u>VISF
DGSTKYYADSVK</u>GRFTISRDNSKNTLDLQMNSLRAEDTALYYCAR<u>EYWGTYYY
GTDV</u>WGQGTTVIVSS

Figure 1N: Amino acid sequence of 2D2 heavy chain variable region

GAAATTGTGTTGACACAGTCTCCAGCCACCCTGTCTTTGTCTCCAGGGGAAAG
AGCCACCCTCTCCTGC<u>AGGGCCAGTCAGAGTGTTAACAGCTACTTAGCCTGG</u>
TACCAACAGAAACCTGGCCAGGCTCCCAGGCTCCTCATCTAT<u>GATGCATCCA
ACAGGGCCACT</u>GGCATCCCAGCCAGGTTCAGTGGCAGTGGGTCTGGGACAGA
CTTCACTCTCACCATCAGCAGCCTAGAGCCTGAAGATTTTGCAGTTTATTACT
GT<u>CAGCAGCGTAGCAACTGGCCTCGGAC</u>GTTCGGCCAAGGGACCAAGGTGG
AAATCAAA

Figure 1O: DNA sequence of 2D2 light chain variable region

EIVLTQSPATLSLSPGERATLSC<u>RASQSVNSYLA</u>WYQQKPGQAPRLLIY<u>DASNRA
T</u>GIPARFSGSGSGTDFTLTISSLEPEDFAVYYC<u>QQRSNWPRT</u>FGQGTKVEIK

Figure 1P: Amino acid sequence of 2D2 light chain variable region

ASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCP
PCPAPELLGGPDVFLFPPKPKDTLMISRTPEVTCVVVDVSHEDPEVKFNWYVDG
VEVHNAKTKPREEQYNSTYRVVSVLTVLHQDWLNGKEYKCKVSNKALPLPEEK
TISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSL
SPGK

Figure 1Q: Amino acid sequence of IgG1 heavy chain constant region with S247D, A338L, and I340E mutations in bold and underlined (SEQ ID NO:43)

RTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC

Figure 1R: Amino acid sequence of IgG1 light chain constant region (SEQ ID NO:44)

V<sub>H</sub>

```
       Germline    QLQLQESGPGLVKPSETLSLTCTVSGGSISSSYYWGWIRQPPGKGLEWI
22b5 I30S N33S    ------------------------------------------------

Germline    GSIYYSGSTYYNPSLKSRVTISVDTSKNQFSLKLSSVTAADTAVYYCAR
22b5 I30S N33S    ------RN-N---------------------------------------

Germline    QYYYGSGSYYNYYYYYGMDWGQGTTVTVSS
22b5 I30S N33S     H------...S----DL-------------
```

V<sub>κ</sub>

```
       Germline    EIVLTQSPATLSLSPGERATLSCRASQSVSSYLAWYQQKPGQAPRLLIYD
22b5 I30S N33S    --------------------------------------------------

Germline    ASNRATGIPARFSGSGSGTDFTLTISSLEPEDFAVYYCQQRSNWPLTFGG
22b5 I30S N33S    --------------------------------------------------

Germline    GTKVEIK
22b5 I30S N33S    -------
```

V<sub>H</sub> germline sequence = SEQ ID NO:45
V<sub>k</sub> germline sequence = SEQ ID NO:46

Figure 2

```
                       SEQUENCE LISTING

<160> NUMBER OF SEQ ID NOS: 46

<210> SEQ ID NO 1
<211> LENGTH: 6
<212> TYPE: PRT
<213> ORGANISM: Human

<400> SEQUENCE: 1

Ser Ser Ser Tyr Trp Gly
1               5

<210> SEQ ID NO 2
<211> LENGTH: 16
<212> TYPE: PRT
<213> ORGANISM: Human

<400> SEQUENCE: 2

Ser Ile Tyr Tyr Ser Gly Arg Asn Tyr Asn Asn Pro Ser Leu Lys Ser
1               5                   10                  15

<210> SEQ ID NO 3
```

```
<211> LENGTH: 15
<212> TYPE: PRT
<213> ORGANISM: Human

<400> SEQUENCE: 3

His Tyr Tyr Gly Ser Gly Ser Tyr Tyr Tyr Asp Leu Asp
1               5                   10                  15

<210> SEQ ID NO 4
<211> LENGTH: 11
<212> TYPE: PRT
<213> ORGANISM: Human

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Human

<400> SEQUENCE: 5

Asp Ala Ser Asn Arg Ala Thr
1               5

<210> SEQ ID NO 6
<211> LENGTH: 9
<212> TYPE: PRT
<213> ORGANISM: Human

<400> SEQUENCE: 6

Gln Gln Arg Ser Asn Trp Pro Leu Thr
1               5

<210> SEQ ID NO 7
<211> LENGTH: 125
<212> TYPE: PRT
<213> ORGANISM: Human

<400> SEQUENCE: 7

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Trp Gly Trp Ile Arg Gln Pro Pro Gly Lys Gly Leu Glu Trp
            35                  40                  45

Ile Gly Ser Ile Tyr Tyr Ser Gly Arg Asn Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg His Tyr Tyr Gly Ser Gly Ser Tyr Tyr Tyr Asp Leu
            100                 105                 110

Asp Val Trp Gly Gln Gly Thr Thr Val Thr Val Ser Ser
        115                 120                 125

<210> SEQ ID NO 8
<211> LENGTH: 107
<212> TYPE: PRT
<213> ORGANISM: Human
```

-continued

```
<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 9
<211> LENGTH: 455
<212> TYPE: PRT
<213> ORGANISM: Human

<400> SEQUENCE: 9

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Trp Gly Trp Ile Arg Gln Pro Pro Gly Lys Gly Leu Glu Trp
        35                  40                  45

Ile Gly Ser Ile Tyr Tyr Ser Gly Arg Asn Tyr Asn Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg His Tyr Tyr Gly Ser Gly Ser Ser Tyr Tyr Tyr Tyr Asp Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Asp Val Phe Leu Phe Pro Pro Lys Pro Lys
                245                 250                 255

Asp Thr Leu Met Ile Ser Arg Thr Pro Glu Val Thr Cys Val Val Val
```

```
              260                 265                 270
Asp Val Ser His Glu Asp Pro Glu Val Lys Phe Asn Trp Tyr Val Asp
            275                 280                 285
Gly Val Glu Val His Asn Ala Lys Thr Lys Pro Arg Glu Glu Gln Tyr
            290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Leu Pro Glu Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
            355                 360                 365
Asn Gln Val Ser Leu Thr Cys Leu Val Lys Gly Phe Tyr Pro Ser Asp
            370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
            435                 440                 445
Leu Ser Leu Ser Pro Gly Lys
            450                 455

<210> SEQ ID NO 10
<211> LENGTH: 214
<212> TYPE: PRT
<213> ORGANISM: Human

<400> SEQUENCE: 10

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
                20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
        50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
```

```
                    180                 185                 190
Ala Cys Glu Val Thr His Gln Gly Leu Ser Ser Pro Val Thr Lys Ser
            195                 200                 205

Phe Asn Arg Gly Glu Cys
        210

<210> SEQ ID NO 11
<211> LENGTH: 375
<212> TYPE: DNA
<213> ORGANISM: Human

<400> SEQUENCE: 11
cagctgcagc tgcaggagtc gggcccagga ctggtgaagc cttcggagac cctgtccctc      60
acctgcactg tctctggtgg ctccatcagc agtagtagct actggggctg gatccgccag     120
cccccaggga aggggctgga gtggattggg agtatctact atagtgggag aaactacaac     180
aacccgtccc tcaagagtcg agtcaccata tccgtagaca cgtccaagaa ccagttctcc     240
ctgaagctga gctctgtgac cgccgcagac acggctgtgt attactgtgc gagacattac     300
tatggttcgg ggagttccta ctactactac gatctggacg tctggggcca agggaccacg     360
gtcaccgtct cctca                                                      375

<210> SEQ ID NO 12
<211> LENGTH: 321
<212> TYPE: DNA
<213> ORGANISM: Human

<400> SEQUENCE: 12
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac tttcggcgga     300
gggaccaagg tggagatcaa a                                               321

<210> SEQ ID NO 13
<211> LENGTH: 5
<212> TYPE: PRT
<213> ORGANISM: Human

<400> SEQUENCE: 13

Ser Tyr Ala Met His
1               5

<210> SEQ ID NO 14
<211> LENGTH: 17
<212> TYPE: PRT
<213> ORGANISM: Human

<400> SEQUENCE: 14

Val Ile Ser Phe Asp Gly Ser Asn Lys Asn Tyr Ala Asp Ser Val Lys
1               5                   10                  15

Gly

<210> SEQ ID NO 15
<211> LENGTH: 12
<212> TYPE: PRT
<213> ORGANISM: Human
```

-continued

<400> SEQUENCE: 15

Glu Tyr Trp Gly Thr Tyr Tyr Tyr Gly Met Asp Val
1               5                   10

<210> SEQ ID NO 16
<211> LENGTH: 11
<212> TYPE: PRT
<213> ORGANISM: Human

<400> SEQUENCE: 16

Arg Ala Ser Gln Ser Val Ser Asn Tyr Leu Ala
1               5                   10

<210> SEQ ID NO 17
<211> LENGTH: 7
<212> TYPE: PRT
<213> ORGANISM: Human

<400> SEQUENCE: 17

Asp Ala Ser Asn Arg Ala Thr
1               5

<210> SEQ ID NO 18
<211> LENGTH: 9
<212> TYPE: PRT
<213> ORGANISM: Human

<400> SEQUENCE: 18

Gln Gln Arg Thr Asn Trp Pro Tyr Thr
1               5

<210> SEQ ID NO 19
<211> LENGTH: 121
<212> TYPE: PRT
<213> ORGANISM: Human

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Glu Tyr Trp Gly Thr Tyr Tyr Tyr Gly Met Asp Val Trp Gly
            100                 105                 110

Gln Gly Thr Thr Val Thr Val Ser Ser
        115                 120

<210> SEQ ID NO 20
<211> LENGTH: 107
<212> TYPE: PRT
<213> ORGANISM: Human

<400> SEQUENCE: 20

Glu Ile Val Leu Thr Gln Ser Pro Ala Thr Leu Ser Leu Ser Pro Gly
1               5                   10                  15

```
Glu Arg Ala Thr Leu Ser Cys Arg Ala Ser Gln Ser Val Ser Asn Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Thr Asn Trp Pro Tyr
                 85                  90                  95

Thr Phe Gly Gln Gly Thr Lys Leu Glu Ile Lys
            100                 105
```

<210> SEQ ID NO 21
<211> LENGTH: 363
<212> TYPE: DNA
<213> ORGANISM: Human

<400> SEQUENCE: 21

```
caggtgcagt tggtggagtc tgggggaggc gtggtccagc ctggggaggtc cctgagactc    60
tcctgtgcag cctctggatt caccttcagt agttatgcta tgcactgggt ccgccaggct   120
ccaggcaagg ggctggagtg ggtggcagtt atatcatttg atggaagcaa taaaaactac   180
gcagactccg tgaagggccg attcaccatc tccagagaca attccaagaa cacgctgtat   240
ctgcaaatga acagcctgag agctgaggac acggctatgt attactgtgc gagagaatac   300
tggggaaccct actactacgg tatggacgtc tggggccaag gaccacggt caccgtctcc   360
tca                                                                 363
```

<210> SEQ ID NO 22
<211> LENGTH: 321
<212> TYPE: DNA
<213> ORGANISM: Human

<400> SEQUENCE: 22

```
gaaattgtgt tgacacagtc tccagccacc ctgtctttgt ctccagggga aagagccacc    60
ctctcctgca gggccagtca gagtgttagc aactacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtaccaact ggccgtacac ttttggccag   300
gggaccaagc tggagatcaa a                                             321
```

<210> SEQ ID NO 23
<211> LENGTH: 6
<212> TYPE: PRT
<213> ORGANISM: Human

<400> SEQUENCE: 23

```
Ser Thr Tyr Ala Met His
 1               5
```

<210> SEQ ID NO 24
<211> LENGTH: 17
<212> TYPE: PRT
<213> ORGANISM: Human

<400> SEQUENCE: 24

Val Ile Ser Tyr Asp Gly Ser Asn Lys Tyr Tyr Ala Asp Ser Val Lys
1               5                   10                  15
Gly

<210> SEQ ID NO 25
<211> LENGTH: 14
<212> TYPE: PRT
<213> ORGANISM: Human

<400> SEQUENCE: 25

Arg Glu Ser Pro Pro Ile Tyr Tyr Tyr Gly Met Asp Val
1               5                   10

<210> SEQ ID NO 26
<211> LENGTH: 10
<212> TYPE: PRT
<213> ORGANISM: Human

<400> SEQUENCE: 26

Arg Ala Ser Gln Ser Val Ser Ser Tyr Leu
1               5                   10

<210> SEQ ID NO 27
<211> LENGTH: 7
<212> TYPE: PRT
<213> ORGANISM: Human

<400> SEQUENCE: 27

Asp Ala Ser Asn Arg Ala Thr
1               5

<210> SEQ ID NO 28
<211> LENGTH: 9
<212> TYPE: PRT
<213> ORGANISM: Human

<400> SEQUENCE: 28

Gln Gln Arg Ser Asn Trp Pro Arg Thr
1               5

<210> SEQ ID NO 29
<211> LENGTH: 122
<212> TYPE: PRT
<213> ORGANISM: Human

<400> SEQUENCE: 29

Gln Val Gln Leu Val Glu Ser Gly Gly Gly Val Gln Pro Gly Arg
1               5                   10                  15

Ser Leu Arg Leu Ser Cys Ala Ala Ser Gly Phe Pro Phe Ser Thr Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Pro Pro Ile Tyr Tyr Tyr Gly Met Asp Val Trp
            100                 105                 110

Gly Gln Gly Thr Thr Val Thr Val Ser Ser
        115                 120

<210> SEQ ID NO 30
<211> LENGTH: 107
<212> TYPE: PRT
<213> ORGANISM: Human

<400> SEQUENCE: 30

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105
```

<210> SEQ ID NO 31
<211> LENGTH: 366
<212> TYPE: DNA
<213> ORGANISM: Human

<400> SEQUENCE: 31

```
caggtgcagc tggtggagtc tgggggaggc gtggtccagc ctgggaggtc cctgagactc    60
tcctgtgcag cctctggatt ccccttcagt acctatgcta tgcactgggt ccgccaggct   120
ccaggcaagg ggctggagtg ggtggcagtt atatcatatg atggaagcaa taaatactac   180
gcagactccg tgaagggccg attcaccatc tccagagaca attccaagaa cacgctgtat   240
ctgcaaatga acagcctgag agctgaggac acggctgtgt attactgtgc gagagagtcc   300
ccccccatct actactacta cggtatggac gtctggggcc aagggaccac ggtcaccgtc   360
tcctca                                                              366
```

<210> SEQ ID NO 32
<211> LENGTH: 321
<212> TYPE: DNA
<213> ORGANISM: Human

<400> SEQUENCE: 32

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctcggac gttcggccaa   300
gggaccaagg tggaaatcaa a                                             321
```

<210> SEQ ID NO 33
<211> LENGTH: 5
<212> TYPE: PRT
<213> ORGANISM: Human

<400> SEQUENCE: 33

```
Ser Tyr Ala Met His
1               5

<210> SEQ ID NO 34
<211> LENGTH: 17
<212> TYPE: PRT
<213> ORGANISM: Human

<400> SEQUENCE: 34

Val Ile Ser Phe Asp Gly Ser Thr Lys Tyr Tyr Ala Asp Ser Val Lys
1               5                   10                  15

Gly

<210> SEQ ID NO 35
<211> LENGTH: 12
<212> TYPE: PRT
<213> ORGANISM: Human

<400> SEQUENCE: 35

Glu Tyr Trp Gly Thr Tyr Tyr Gly Thr Asp Val
1               5                   10

<210> SEQ ID NO 36
<211> LENGTH: 11
<212> TYPE: PRT
<213> ORGANISM: Human

<400> SEQUENCE: 36

Arg Ala Ser Gln Ser Val Asn Ser Tyr Leu Ala
1               5                   10

<210> SEQ ID NO 37
<211> LENGTH: 7
<212> TYPE: PRT
<213> ORGANISM: Human

<400> SEQUENCE: 37

Asp Ala Ser Asn Arg Ala Thr
1               5

<210> SEQ ID NO 38
<211> LENGTH: 9
<212> TYPE: PRT
<213> ORGANISM: Human

<400> SEQUENCE: 38

Gln Gln Arg Ser Asn Trp Pro Arg Thr
1               5

<210> SEQ ID NO 39
<211> LENGTH: 121
<212> TYPE: PRT
<213> ORGANISM: Human

<400> SEQUENCE: 39

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
                35                  40                  45

Ala Val Ile Ser Phe Asp Gly Ser Thr Lys Tyr Tyr Ala Asp Ser Val
                50                  55                  60
```

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Leu Tyr Tyr Cys
                85                  90                  95

Ala Arg Glu Tyr Trp Gly Thr Tyr Tyr Tyr Gly Thr Asp Val Trp Gly
            100                 105                 110

Gln Gly Thr Thr Val Ile Val Ser Ser
        115                 120

<210> SEQ ID NO 40
<211> LENGTH: 107
<212> TYPE: PRT
<213> ORGANISM: Human

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 41
<211> LENGTH: 363
<212> TYPE: DNA
<213> ORGANISM: Human

<400> SEQUENCE: 41
caggtgcaac tggtggagtc tgggggaggc gtggtccagc ctggagggtc cctgagactc      60
tcctgtgcag cctctggatt caccttcagt agctatgcta tgcactgggt ccgccaggct     120
ccaggcaagg ggctggagtg ggtggcagtt atatcatttg atggaagcac taaatactac     180
gcagactccg tgaagggccg attcaccatc tccagagaca attccaagaa cacgctggat     240
ctgcaaatga acagcctgag agctgaggac acggctctgt attactgtgc gagagaatac     300
tggggaacct actactacgg gacggacgtc tggggccaag gaccacggt catcgtctcc      360 tca                                                                   363

<210> SEQ ID NO 42
<211> LENGTH: 321
<212> TYPE: DNA
<213> ORGANISM: Human

<400> SEQUENCE: 42
gaaattgtgt tgacacagtc tccagccacc ctgtctttgt ctccagggga aagagccacc      60
ctctcctgca gggccagtca gagtgttaac agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctcggac gttcggccaa     300
gggaccaagg tggaaatcaa a                                              321

<210> SEQ ID NO 43
<211> LENGTH: 330
<212> TYPE: PRT
<213> ORGANISM: Human

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 44
<211> LENGTH: 107
<212> TYPE: PRT
<213> ORGANISM: Human

<400> SEQUENCE: 44

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 45
<211> LENGTH: 130
<212> TYPE: PRT
<213> ORGANISM: Human

<400> SEQUENCE: 45

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Tyr Tyr Tyr Gly Ser Gly Ser Tyr Tyr Asn Tyr Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 46
<211> LENGTH: 107
<212> TYPE: PRT
<213> ORGANISM: Human

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Gln Gln Arg Ser Asn Trp Pro Leu
                85                  90                  95
Thr Phe Gly Gly Gly Thr Lys Val Glu Ile Lys
            100                 105
```

ALPHA5-BETA1 ANTIBODIES AND THEIR USES

CROSS-REFERENCE TO RELATED APPLICATIONS

This application is a continuation application of U.S. application Ser. No. 12/365,638, filed Feb. 4, 2009 now U.S. Pat. No. 8,039,596, which also claims priority to U.S. Provisional Application No. 61/026,207 filed on Feb. 5, 2008, and to U.S. Provisional Application No. 61/095,429 filed on Sep. 9, 2008, each of which are incorporated herein by reference in their entirety.

FIELD

The present disclosure relates to antibodies and antigen-binding portions thereof that bind to α5β1. The disclosure also relates to nucleic acid molecules encoding such antibodies and antigen-binding portions, methods of making α5β1 antibodies and antigen-binding portions, compositions comprising these antibodies and antigen-binding portions and methods of using the antibodies, antigen-binding portions, and compositions.

BACKGROUND

Integrin α5β1 is a heterodimeric cell surface protein that binds fibronectin and is involved in cell attachment and angiogenesis. This heterodimer is made up of an α5 subunit and a β1 subunit. Integrin α5β1 is referred to as the "classic fibronectin receptor" that plays key roles in matrix adhesion, migration, proliferation, differentiation, and survival. Although several integrins bind to fibronectin (FN), α5β1 is selective for FN as it requires both peptide sequences on the ninth (PHSRN) and tenth (RGDS) type III repeats of FN for ligand recognition and optimal interaction. (Danen et al. *J. Biol. Chem.* 270(37):21612-21618 (1995); Redick et al. *J. Cell Biol.* 149(2):521-527 (2000); Takagi et al. *EMBO J.* 22:4607-4615 (2003)). Integrin-mediated cell adhesion to FN, can trigger calcium fluxes, activate tyrosine and serine/threonine protein kinases and inositol lipid metabolism, and regulate the activity of the Rho family of small GTPases that controls the actin cytoskeleton and cell cycle progression.

Expression of α5β1 is observed in most embryonic tissues, but the level diminishes after birth in a manner consistent with terminal cell differentiation (Muschler & Horwitz *Development* 113(1):327-337 (1991)). In wild type adult mice, expression is mainly in the vasculature and connective tissue, although low levels of the receptor are widely distributed. Expression of both α5β1 and FN are significantly and coordinately enhanced on blood vessels of human tumors and in growth factor and cytokine stimulated tissues. Angiogenic cytokines such as bFGF, VEGF, IL-8, TGF-beta, and TNF-α upregulate α5β1 expression on endothelial cells in-vitro and in-vivo, whereas these molecules are minimally expressed on normal human vessels and tissues (Kim et al. *Am. J. Path.* 156(4):1345-62 (2000); Enaida et al. *Fukushima J. Med. Sci.* 44(1):43-52 (1998); Klein et al. *Mol. Biol. Cell* 4(10):973-982 (1993)).

High levels of α5β1 expression are not limited to the vasculature, as tumor cells are also frequently observed to express α5β1 in many types of cancer. Tumor hypoxia has been associated with increased tumor α5β1 expression (Mousa et al. *J. Cell. Biochem.* 74:135-143 (1999)). Integrins are thought to be important for tumor intravasation into newly formed capillaries and extravasation to distant sites, leading to tumor spreading and metastatic disease. Altogether, the expression pattern of α5β1 is consistent with multiple roles in promoting cancer, by mediating both stromal and tumor cell activities. Various clinical studies have associated α5β1 upregulation on tumor cells with progression of human melanoma, oral squamous cell carcinoma, and B-cell leukemias (Jin & Varner, *Br. J. Cancer* 90:561-565 (2004); Danen et al. *Histopathology* 24(3):249-256 (1994); Shinohara et al., *Am. J. Clin. Pathol.* 111(1):75-88 (1999)).

SUMMARY

The present disclosure provides isolated monoclonal antibodies, in particular human monoclonal antibodies, that exhibit high affinity binding to human integrin α5β1. The antibodies described in the present disclosure are typically human antibodies, although in alternative cases the antibodies can be murine antibodies, chimeric antibodies, or humanized antibodies.

In one aspect, the disclosure pertains to an isolated monoclonal antibody, or an antigen-binding portion thereof, wherein the antibody: (a) binds to human integrin α5β1 with a $K_D$ of $1 \times 10^{-7}$ M or less; and (b) is capable of inducing antibody dependent cellular cytotoxicity. For example, in one case, the antibody belongs to a subclass that is capable of inducing ADCC, such as IgG1 or IgG3. In another case, the ADCC activity is the result of introducing carbohydrate modifications, such as altered glycosylation patterns, into the Fc region as compared to the native carboyhydrate pattern.

In certain cases, the antibody binds to human integrin α5β1 with a $K_D$ of $5 \times 10^{-8}$ M or less, $2 \times 10^{-8}$ M or less, $1 \times 10^{-8}$ M or less, $5 \times 10^{-9}$ M or less, $4 \times 10^{-9}$ M or less, $3 \times 10^{-9}$ M or less, or $2.7 \times 10^{-9}$ M or less.

In a further aspect, the present disclosure provides an isolated monoclonal antibody, or an antigen-binding portion thereof, wherein the antibody: (a) binds to human integrin α5β1 with a $K_D$ of $1 \times 10^{-7}$ M or less; and (b) demonstrates enhanced ADCC activity relative to a comparable antibody. For example, in one case, the antibody with enhanced ADCC activity comprises at least one mutation in the Fc region as compared to the wild type Fc region, and the enhanced ADCC activity is relative to the same antibody, but comprising the wild type Fc region. In certain examples, the antibody binds to human integrin α5β1 with a $K_D$ of $5 \times 10^{-8}$ M or less, $2 \times 10^{-8}$ M or less, $1 \times 10^{-8}$ M or less, $5 \times 10^{-9}$ M or less, $4 \times 10^{-9}$ M or less, $3 \times 10^{-9}$ M or less, or $2.7 \times 10^{-9}$M or less. In further examples, the antibody demonstrates enhanced ADCC activity relative to a comparable antibody that is at least 1.1 fold, at least 1.2 fold, at least 1.3 fold, at least 1.5 fold, at least 2-fold, at least 3-fold, at least 5-fold, at least 10-fold, at least 20-fold, at least 30-fold, at least 40-fold, at least 50-fold, at least 100-fold, at least 200-fold, at least 500-fold, or at least 1000-fold as compared to a comparable antibody, wherein the comparable antibody is the same antibody, but with the wild type Fc region.

In a further aspect, the present disclosure provides an isolated monoclonal antibody, or antigen binding portion thereof, wherein the antibody: (a) binds to human integrin α5β1 with a $K_D$ of $1 \times 10^{-7}$ M or less; and (b) comprises at least one mutation in the Fc region as compared to the wild type Fc region. For example, in one case, the subclass of the antibody is IgG1 and at least one amino acid in the Fc region of the IgG1 subclass is mutated. In a further example, the at least one mutation occurs at position serine 247, alanine 338, or isoleucine 340 in the Fc region of the IgG1 subclass. In a further example, the at least one mutation is selected from the group consisting of S247D, A338L, and I340E. In yet a further example, the antibody comprises the mutations S247D, A338L, and I340E.

A further aspect of the present disclosure is an isolated monoclonal antibody, or antigen binding portion thereof, wherein the antibody cross-competes or competes for binding to human integrin α5β1 with an antibody that comprises: (a) a heavy chain variable region comprising the amino acid sequence of SEQ ID NO: 7, or conservative modifications thereof; and (b) a light chain variable region comprising the amino acid sequence of SEQ ID NO: 8, or conservative modifications thereof.

A further aspect of the present disclosure is an isolated monoclonal antibody, or an antigen-binding portion thereof, comprising a heavy chain variable region that is the product of or derived from a human $V_H$ 4-39 gene, wherein the antibody specifically binds human integrin α5β1.

A further aspect of the present disclosure is an isolated monoclonal antibody, or an antigen-binding portion thereof, comprising a light chain variable region that is the product of or derived from a human $V_K$ L6 gene, wherein the antibody specifically binds human integrin α5β1.

In another aspect, the disclosure provides an isolated monoclonal antibody or antigen binding portion thereof comprising a heavy chain variable region CDR1 comprising SEQ ID NO: 1, or conservative modifications thereof. In another aspect, the disclosure provides an isolated monoclonal antibody or antigen binding portion thereof comprising a heavy chain variable region CDR2 comprising SEQ ID NO: 2, or conservative modifications thereof. In another aspect, the disclosure provides an isolated monoclonal antibody or antigen binding portion thereof comprising a heavy chain variable region CDR3 comprising SEQ ID NO: 3, or conservative modifications thereof. In another aspect, the disclosure provides an isolated monoclonal antibody or antigen binding portion thereof comprising a light chain variable region CDR1 comprising SEQ ID NO: 4, or conservative modifications thereof. In another aspect, the disclosure provides an isolated monoclonal antibody or antigen binding portion thereof comprising a light chain variable region CDR2 comprising SEQ ID NO: 5, or conservative modifications thereof. In another aspect, the disclosure provides an isolated monoclonal antibody or antigen binding portion thereof comprising a light chain variable region CDR3 comprising SEQ ID NO: 6, or conservative modifications thereof. In another aspect, the disclosure provides an isolated monoclonal antibody or antigen binding portion thereof comprising:
  (a) a heavy chain variable region CDR1 comprising SEQ ID NO: 1, or conservative modifications thereof;
  (b) a heavy chain variable region CDR2 comprising SEQ ID NO: 2, or conservative modifications thereof;
  (c) a heavy chain variable region CDR3 comprising SEQ ID NO: 3, or conservative modifications thereof;
  (d) a light chain variable region CDR1 comprising SEQ ID NO: 4, or conservative modifications thereof;
  (e) a light chain variable region CDR2 comprising SEQ ID NO: 5, or conservative modifications thereof; and
  (f) a light chain variable region CDR3 comprising SEQ ID NO: 6, or conservative modifications thereof.

In a further aspect, the present disclosure provides an isolated monoclonal antibody or antigen binding portion thereof comprising a heavy chain variable region comprising the amino acid sequence of SEQ ID NO: 7, or conservative modifications thereof. For example, the disclosure provides an antibody or antigen-binding portion thereof comprising a heavy chain variable region that is at least 80%, at least 85%, at least 90%, at least 95%, at least 97%, at least 98%, or at least 99% identical to the amino acid sequence set forth in SEQ ID NO:7. In a further aspect, the disclosure provides an isolated monoclonal antibody or antigen binding portion thereof comprising a light chain variable region comprising the amino acid sequence of SEQ ID NO: 8, or conservative modifications thereof. For example, the disclosure provides an antibody or antigen-binding portion thereof comprising a light chain variable region that is at least 80%, at least 85%, at least 90%, at least 95%, at least 97%, at least 98%, or at least 99% identical to the amino acid sequence set forth in SEQ ID NO:8. In a further aspect, the disclosure provides an isolated monoclonal antibody or antigen binding portion thereof comprising a heavy chain variable region comprising the amino acid sequence of SEQ ID NO: 7, or conservative modifications thereof, and a light chain variable region comprising the amino acid sequence of SEQ ID NO: 8, or conservative modifications thereof. For example, the disclosure provides an isolated monoclonal antibody or antigen binding portion thereof comprising a heavy chain variable region that is at least 80%, at least 85%, at least 90%, at least 95%, at least 97%, at least 98%, or at least 99% identical to the amino acid sequence set forth in SEQ ID NO: 7, and a light chain variable region that is at least 80%, at least 85%, at least 90%, at least 95%, at least 97%, at least 98%, or at least 99% identical to the amino acid sequence set forth in SEQ ID NO: 8.

In another aspect, the disclosure provides an isolated monoclonal antibody or antigen binding portion thereof comprising a heavy chain variable region CDR1 comprising SEQ ID NO: 13, or conservative modifications thereof. In another aspect, the disclosure provides an isolated monoclonal antibody or antigen binding portion thereof comprising a heavy chain variable region CDR2 comprising SEQ ID NO: 14, or conservative modifications thereof. In another aspect, the disclosure provides an isolated monoclonal antibody or antigen binding portion thereof comprising a heavy chain variable region CDR3 comprising SEQ ID NO: 15, or conservative modifications thereof. In another aspect, the disclosure provides an isolated monoclonal antibody or antigen binding portion thereof comprising a light chain variable region CDR1 comprising SEQ ID NO: 16, or conservative modifications thereof. In another aspect, the disclosure provides an isolated monoclonal antibody or antigen binding portion thereof comprising a light chain variable region CDR2 comprising SEQ ID NO: 17, or conservative modifications thereof. In another aspect, the disclosure provides an isolated monoclonal antibody or antigen binding portion thereof comprising a light chain variable region CDR3 comprising SEQ ID NO: 18, or conservative modifications thereof. In another aspect, the disclosure provides an isolated monoclonal antibody or antigen binding portion thereof comprising:
  (a) a heavy chain variable region CDR1 comprising SEQ ID NO: 13, or conservative modifications thereof;
  (b) a heavy chain variable region CDR2 comprising SEQ ID NO: 14, or conservative modifications thereof;
  (c) a heavy chain variable region CDR3 comprising SEQ ID NO: 15, or conservative modifications thereof;
  (d) a light chain variable region CDR1 comprising SEQ ID NO: 16, or conservative modifications thereof;
  (e) a light chain variable region CDR2 comprising SEQ ID NO: 17, or conservative modifications thereof; and
  (f) a light chain variable region CDR3 comprising SEQ ID NO: 18, or conservative modifications thereof.

In a further aspect, the present disclosure provides an isolated monoclonal antibody or antigen binding portion thereof comprising a heavy chain variable region comprising the amino acid sequence of SEQ ID NO: 19, or conservative modifications thereof. In a further aspect, the disclosure provides an isolated monoclonal antibody or antigen binding portion thereof comprising a light chain variable region comprising the amino acid sequence of SEQ ID NO: 20, or conservative modifications thereof. In a further aspect, the disclosure provides an isolated monoclonal antibody or antigen binding portion thereof comprising a heavy chain variable region comprising the amino acid sequence of SEQ ID NO: 19, or conservative modifications thereof, and a light chain variable region comprising the amino acid sequence of SEQ ID NO: 20, or conservative modifications thereof.

In another aspect, the disclosure provides an isolated monoclonal antibody or antigen binding portion thereof comprising a heavy chain variable region CDR1 comprising SEQ ID NO: 23, or conservative modifications thereof. In another aspect, the disclosure provides an isolated monoclonal antibody or antigen binding portion thereof comprising a heavy chain variable region CDR2 comprising SEQ ID NO: 24, or conservative modifications thereof. In another aspect, the disclosure provides an isolated monoclonal antibody or antigen binding portion thereof comprising a heavy chain variable region CDR3 comprising SEQ ID NO: 25, or conservative modifications thereof. In another aspect, the disclosure provides an isolated monoclonal antibody or antigen binding portion thereof comprising a light chain variable region CDR1 comprising SEQ ID NO: 26, or conservative modifications thereof. In another aspect, the disclosure provides an isolated monoclonal antibody or antigen binding portion thereof comprising a light chain variable region CDR2 comprising SEQ ID NO: 27, or conservative modifications thereof. In another aspect, the disclosure provides an isolated monoclonal antibody or antigen binding portion thereof comprising a light chain variable region CDR3 comprising SEQ ID NO: 28, or conservative modifications thereof. In another aspect, the disclosure provides an isolated monoclonal antibody or antigen binding portion thereof comprising:

(a) a heavy chain variable region CDR1 comprising SEQ ID NO: 23, or conservative modifications thereof;
(b) a heavy chain variable region CDR2 comprising SEQ ID NO: 24, or conservative modifications thereof;
(c) a heavy chain variable region CDR3 comprising SEQ ID NO: 25, or conservative modifications thereof;
(d) a light chain variable region CDR1 comprising SEQ ID NO: 26, or conservative modifications thereof;
(e) a light chain variable region CDR2 comprising SEQ ID NO: 27, or conservative modifications thereof; and
(f) a light chain variable region CDR3 comprising SEQ ID NO: 28, or conservative modifications thereof.

In a further aspect, the present disclosure provides an isolated monoclonal antibody or antigen binding portion thereof comprising a heavy chain variable region comprising the amino acid sequence of SEQ ID NO: 29, or conservative modifications thereof. In a further aspect, the disclosure provides an isolated monoclonal antibody or antigen binding portion thereof comprising a light chain variable region comprising the amino acid sequence of SEQ ID NO: 30, or conservative modifications thereof. In a further aspect, the disclosure provides an isolated monoclonal antibody or antigen binding portion thereof comprising a heavy chain variable region comprising the amino acid sequence of SEQ ID NO: 29, or conservative modifications thereof, and a light chain variable region comprising the amino acid sequence of SEQ ID NO: 30, or conservative modifications thereof.

In another aspect, the disclosure provides an isolated monoclonal antibody or antigen binding portion thereof comprising a heavy chain variable region CDR1 comprising SEQ ID NO: 33, or conservative modifications thereof. In another aspect, the disclosure provides an isolated monoclonal antibody or antigen binding portion thereof comprising a heavy chain variable region CDR2 comprising SEQ ID NO: 34, or conservative modifications thereof. In another aspect, the disclosure provides an isolated monoclonal antibody or antigen binding portion thereof comprising a heavy chain variable region CDR3 comprising SEQ ID NO: 35, or conservative modifications thereof. In another aspect, the disclosure provides an isolated monoclonal antibody or antigen binding portion thereof comprising a light chain variable region CDR1 comprising SEQ ID NO: 36, or conservative modifications thereof. In another aspect, the disclosure provides an isolated monoclonal antibody or antigen binding portion thereof comprising a light chain variable region CDR2 comprising SEQ ID NO: 37, or conservative modifications thereof. In another aspect, the disclosure provides an isolated monoclonal antibody or antigen binding portion thereof comprising a light chain variable region CDR3 comprising SEQ ID NO: 38, or conservative modifications thereof. In another aspect, the disclosure provides an isolated monoclonal antibody or antigen binding portion thereof comprising: (a) a heavy chain variable region CDR1 comprising SEQ ID NO: 33, or conservative modifications thereof; (b) a heavy chain variable region CDR2 comprising SEQ ID NO: 34, or conservative modifications thereof; (c) a heavy chain variable region CDR3 comprising SEQ ID NO: 35, or conservative modifications thereof; (d) a light chain variable region CDR1 comprising SEQ ID NO: 36, or conservative modifications thereof; (e) a light chain variable region CDR2 comprising SEQ ID NO: 37, or conservative modifications thereof; and (f) a light chain variable region CDR3 comprising SEQ ID NO: 38, or conservative modifications thereof.

In a further aspect, the present disclosure provides an isolated monoclonal antibody or antigen binding portion thereof comprising a heavy chain variable region comprising the amino acid sequence of SEQ ID NO: 39, or conservative modifications thereof. In a further aspect, the disclosure provides an isolated monoclonal antibody or antigen binding portion thereof comprising a light chain variable region comprising the amino acid sequence of SEQ ID NO: 40, or conservative modifications thereof. In a further aspect, the disclosure provides an isolated monoclonal antibody or antigen binding portion thereof comprising a heavy chain variable region comprising the amino acid sequence of SEQ ID NO: 39, or conservative modifications thereof, and a light chain variable region comprising the amino acid sequence of SEQ ID NO: 40, or conservative modifications thereof.

In a further aspect there is provided an isolated antibody or antigen binding portion thereof that binds to the same epitope on human integrin α5β1 as any of the antibodies disclosed herein and/or competes for binding to human integrin α5β1 with such an antibody.

In one embodiment, the disclosure provides the material deposited at the ATCC as Deposit No. PTA-9377. In another embodiment, the disclosure provides the material deposited at the ATCC as Deposit No. PTA-9378. In another embodiment, the disclosure provides an isolated antibody that comprises the heavy chain variable region as deposited at the ATCC as Deposit No. PTA-9377. In another embodiment, the disclosure provides an isolated antibody that comprises the light chain variable region as deposited at the ATCC as Deposit No. PTA-9378. In another embodiment, the disclosure provides an isolated antibody comprising the heavy chain variable region as deposited at the ATCC as Deposit No. PTA-9377, but wherein the germline mutations I30S and N33S have been made in the VH region. In a further embodiment, the disclosure provides an isolated antibody that comprises the heavy chain and light chain variable regions as deposited at the ATCC as Deposit Nos. PTA-9377 and PTA-9378, respectively, or said antibody wherein the germline mutations I30S and N33S have been made in the VH region. In a further embodiment, the disclosure provides an isolated antibody that comprises the heavy chain CDR1, CDR2, and CDR3 regions of the heavy chain variable region as deposited at the ATCC as Deposit No. PTA-9377, or comprises said CDR1, CDR2, and CDR3 when said heavy chain variable region contains the germline mutations I30S and N33S. In a further embodiment, the disclosure provides an isolated antibody that comprises the light chain CDR1, CDR2, and CDR3 regions of the light chain variable region as deposited at the ATCC as Deposit No. PTA-9378. In a further embodiment, the disclosure provides an isolated antibody that comprises the light chain CDR1, CDR2, and CDR3 regions and the heavy chain CDR1, CDR2, and CDR3 regions of the heavy and light chain variable regions as deposited at the ATCC as Deposit Nos. PTA-9377 and PTA-9378, respectively, or comprises said CDR1, CDR2, and CDR3 regions when said heavy chain variable region contains the germline mutations I30S and N33S.

The antibodies of the disclosure can be, for example, full-length antibodies, for example of an IgG1 or IgG4 subclass. Alternatively, the antibodies can be antibody fragments, such as Fab or Fab'2 fragments, or single chain antibodies. In one case, the present disclosure provides any of the antibodies as described above, which is a human full-length antibody of subclass IgG1, wherein at least one amino acid in the Fc region of the IgG1 subclass is mutated. In a further case, the at least one mutation occurs at position serine 247, alanine 338, or isoleucine 340. In a further case, the at least one mutation is selected from the group consisting of S247D, A338L, and I340E. In yet a further case, the antibody comprises the mutations S247D, A338L, and I340E.

In a further aspect, the disclosure provides an isolated monoclonal antibody comprising a heavy chain as shown in SEQ ID NO: 9, or conservative modifications thereof. For example, the antibody comprises a heavy chain that is at least 80%, at least 85%, at least 90%, at least 95%, at least 97%, at least 98%, or at least 99% identical to the amino acid sequence set forth in SEQ ID NO:9. In a further aspect, the disclosure provides an isolated monoclonal antibody comprising a light chain as shown in SEQ ID NO: 10, or conservative modifications thereof. For example, the antibody comprises a light chain that is at least 80%, at least 85%, at least 90%, at least 95%, at least 97%, at least 98%, or at least 99% identical to the amino acid sequence set forth in SEQ ID NO:10. In a further aspect, the disclosure provides an isolated monoclonal antibody comprising a heavy chain as shown in SEQ ID NO: 9, or conservative modifications thereof, and a light chain as shown in SEQ ID NO: 10, or conservative modifications thereof. For example, the antibody comprises a heavy chain that is at least 80%, at least 85%, at least 90%, at least 95%, at least 97%, at least 98%, or at least 99% identical to the amino acid sequence set forth in SEQ ID NO:9, and a light chain that is at least 80%, at least 85%, at least 90%, at least 95%, at least 97%, at least 98%, or at least 99% identical to the amino acid sequence set forth in SEQ ID NO:10.

In some embodiments, the C-terminal lysine of the heavy chain of any of the anti-α5β1 antibodies of the disclosure as described is cleaved, and is thus not present. For example, in some embodiments antibodies of the present disclosure comprise the IgG1 constant heavy region as shown in SEQ ID NO: 43, but where the C-terminal lysine is not present. In various cases, the heavy and light chains of the anti-α5β1 antibodies may optionally include a signal sequence.

In a further aspect, the disclosure provides a composition comprising any of the antibodies, or antigen-binding portions thereof, as described herein, and a pharmaceutically acceptable carrier.

In a further aspect, the disclosure provides an immunoconjugate comprising any of the antibodies, or antigen-binding portions thereof, as described herein, linked to a therapeutic agent. In one case, the therapeutic agent is a cytotoxin or a radioactive isotope. In a further aspect, the disclosure provides a composition comprising any of the immunoconjugates described herein and a pharmaceutically acceptable carrier. The disclosure also provides a bispecific molecule comprising an antibody, or antigen-binding portion thereof, linked to a second functional moiety having a different binding specificity than said antibody, or antigen binding portion thereof.

Compositions comprising an antibody, or antigen-binding portion thereof, or immunoconjugate or bispecific molecule of the disclosure and a pharmaceutically acceptable carrier are also provided.

Nucleic acid molecules encoding the antibodies, or antigen-binding portions thereof, are also encompassed by the disclosure, as well as expression vectors comprising such nucleic acids and host cells comprising such expression vectors. One aspect, for example, is an isolated nucleic acid molecule, or an expression vector, comprising the sequence as shown in SEQ ID NO: 11, or conservative modifications thereof. A further aspect is an isolated nucleic acid molecule, or an expression vector, comprising the sequence as shown in SEQ ID NO: 12, or conservative modifications thereof. A further aspect is an isolated nucleic acid molecule, or an expression vector, comprising the sequence selected from the group consisting of SEQ ID NOs: 21, 22, 31, 32, 41, and 42, or conservative modifications thereof. The disclosure also provides a transgenic mouse comprising human immunoglobulin heavy and light chain transgenes, wherein the mouse expresses an antibody of the disclosure, as well as hybridomas prepared from such a mouse, wherein the hybridoma produces the antibody of the disclosure.

The disclosure further provides a host cell comprising any of the expression vectors described herein.

In a further aspect, the disclosure provides a method for preparing an anti-integrin α5β1 antibody which comprises expressing the antibody in any of the host cells described herein and isolating the antibody from the host cell.

In a further aspect, the disclosure provides a method for inhibiting growth of tumor cells expressing integrin α5β1, comprising contacting the cells with an antibody or antigen binding portion thereof that binds to human integrin α5β1 with a $K_D$ of $1\times10^{-7}$ M or less and is capable of inducing antibody dependent cellular cytotoxicity. In one case, the antibody is a fully human antibody. In a further case, the antibody or antigen-binding portion thereof is engineered to enhance its ability to induce antibody dependent cellular cytotoxicity. In yet a further case, the enhancement is achieved by mutation of at least one amino acid residue in the Fc region.

In a further aspect, the disclosure provides a method of inhibiting growth of tumor cells expressing integrin α5β1, comprising contacting the cells with any of the antibodies, or antigen-binding portions thereof, as described herein, in an amount effective to inhibit growth of the tumor cells.

In a further aspect, the disclosure provides the use of any of the antibodies or antigen-binding portions thereof, as described herein, for the manufacture of a medicament for the treatment of abnormal cell growth. In still a further aspect, the disclosure provides any of the antibodies or antigen-binding portions thereof, as described herein, for use in the treatment and/or diagnosis of abnormal cell growth. In one embodiment of this method, the abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

The disclosure also provides methods for making "second generation" anti-α5β1 antibodies based on the sequences of the anti-α5β1 antibodies provided herein. For example, the disclosure provides a method for preparing an anti-α5β1 antibody comprising: (a) providing: (i) a heavy chain variable region antibody sequence comprising a CDR1 sequence as shown in SEQ ID NOs: 1, 13, 23, or 33, a CDR2 sequence as shown in SEQ ID NO: 2, 14, 24, or 34 and/or a CDR3 sequence as shown in SEQ ID NO: 3, 15, 25, or 35; and/or (ii) a light chain variable region antibody sequence comprising a CDR1 sequence as shown in SEQ ID NOs: 4, 16, 26, or 36, a CDR2 sequence as shown in SEQ ID NOs: 5, 17, 27, or 37 and/or a CDR3 sequence as shown in SEQ ID NOs: 6, 18, 28, or 38; (b) altering at least one amino acid residue within the heavy chain variable region antibody sequence and/or the light chain variable region antibody sequence to create at least one altered antibody sequence; and (c) expressing the altered antibody sequence as a protein.

Other features and advantages of the instant disclosure will be apparent from the following detailed description and examples which should not be construed as limiting. The contents of all references, Genbank entries, patents and published patent applications cited throughout this specification are expressly incorporated herein by reference.

BRIEF DESCRIPTION OF THE DRAWINGS

FIG. 1A shows the DNA sequence of the 22B5 heavy chain variable region (SEQ ID NO:11); FIG. 1B shows the amino acid sequence of the 22B5 heavy chain variable region (SEQ ID NO:7)—CDR regions are underlined; FIG. 1C shows the DNA sequence of the 22B5 light chain variable region (SEQ ID NO:12); FIG. 1D shows the amino acid sequence of the 22B5 light chain variable region (SEQ ID NO:8)—CDR regions are underlined; FIG. 1E shows the DNA sequence of the 24C7 heavy chain variable region (SEQ ID NO:21); FIG. 1F shows the amino acid sequence of the 24C7 heavy chain variable region (SEQ ID NO:19)—CDR regions are underlined; FIG. 1G shows the DNA sequence of the 24C7 light chain variable region (SEQ ID NO:22); FIG. 1H shows the amino acid sequence of the 24C7 light chain variable region (SEQ ID NO:20)—CDR regions are underlined; FIG. 1I shows the DNA sequence of the 1D9 heavy chain variable region (SEQ ID NO:31); FIG. 1J shows the amino acid sequence of the 1D9 heavy chain variable region (SEQ ID NO:29)—CDR regions are underlined. FIG. 1K shows the DNA sequence of the 1D9 light chain variable region (SEQ ID NO:32); FIG. 1L shows the amino acid sequence of the 1D9 light chain variable region (SEQ ID NO:30)—CDR regions are underlined; FIG. 1M shows the DNA sequence of the 2D2 heavy chain variable region (SEQ ID NO:41); FIG. 1N shows the amino acid sequence of the 2D2 heavy chain variable region (SEQ ID NO:39)—CDR regions are underlined; FIG. 1O shows the DNA sequence of the 2D2 light chain variable region (SEQ ID NO:42); FIG. 1P shows the amino acid sequence of the 2D2 light chain variable region (SEQ ID NO:40)—CDR regions are underlined; FIG. 1Q shows the amino acid sequence of the IgG1 heavy chain constant region with mutations S247D, A338L, and I340E underlined; and FIG. 1R shows the amino acid sequence of the IgG1 light chain constant region.

FIG. 2 shows the alignment of the 22B5 heavy chain variable domain ($V_H$) with the corresponding germline sequence. Also shown is the alignment of the 22B5 light chain variable domain ($V_\kappa$) with the corresponding germline sequence. CDR regions are underlined, identical residues are represented by dashes and dots indicate deletions.

FIG. 8 shows in-vitro ADCC induced by 22B5/DLE compared with 22B5 wt IgG1.

FIG. 10 shows the inhibition activity of 22B5/DLE in the A549-Luc experimental metastasis model.

FIG. 13A: Gross appearance of lungs resected from all groups. FIG. 13B: Quantitation of lung weight (* p<0.05, 1D9 IgG1 DLE vs 1D9 IgG2). FIG. 13C: Quantitation of the numbers of metastatic colonies visible on the lung surface. Statistical analysis by ANOVA and Bonferroni's multiple comparison test (* p<0.05, 1D9 IgG1 DLE vs 1D9 IgG2; * p<0.05, 1D9 IgG1 DLE vs anti-KLH IgG2).

DETAILED DESCRIPTION

Figure 3:
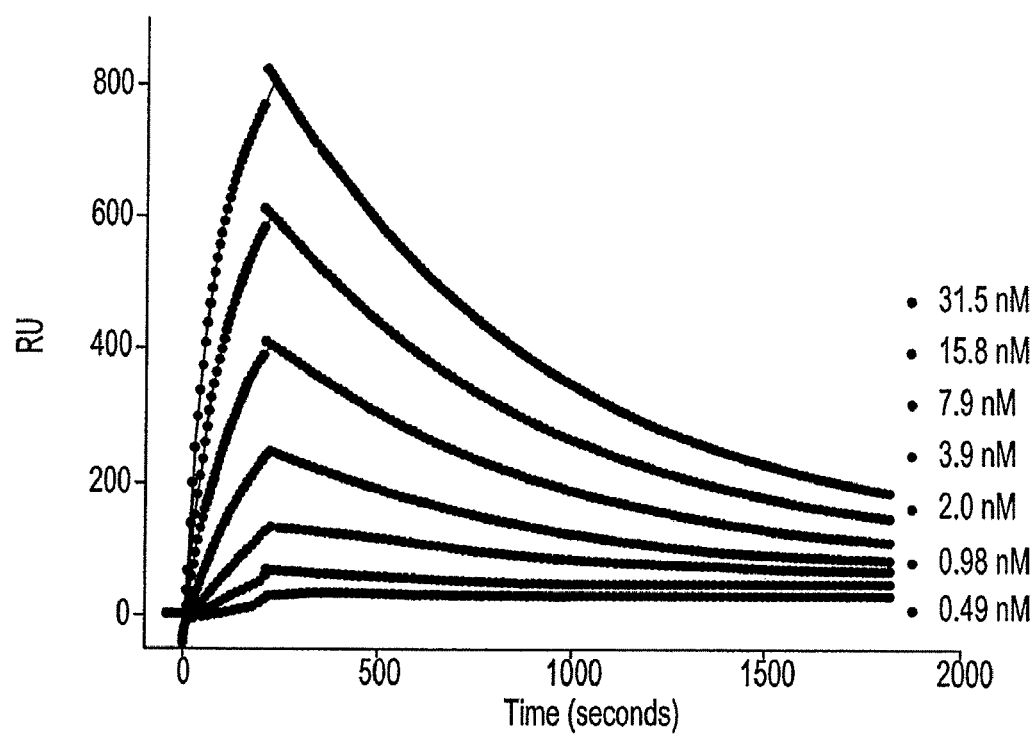
FIG. 3 shows an overlay of the sensorgrams obtained by injecting various concentrations of α5β1 recombinant extracellular domain over immobilized 22B5/DLE. This data was collected in the presence of 4.0 mM $CaCl_2$. The order of injections was from low to high concentration.

The present disclosure relates to isolated monoclonal antibodies, particularly human monoclonal antibodies, that bind specifically to α5β1 with high affinity. In certain cases, the antibodies of the disclosure are derived from particular heavy and light chain germline sequences and/or comprise particular structural features such as CDR regions comprising particular amino acid sequences. The disclosure provides isolated antibodies, methods of making such antibodies, immunoconjugates and bispecific molecules comprising such antibodies and pharmaceutical compositions containing the antibodies, immunoconjugates or bispecific molecules of the disclosure. The disclosure also relates to methods of using the antibodies, such as to detect and, as well as to treat diseases associated with expression of α5β1, such as abnormal cell growth (e.g. cancer). Accordingly, the disclosure also provides methods of using the anti-α5β1 antibodies or antigen binding portions thereof to treat various types of abnormal cell growth, such as cancer.

In order that the present disclosure may be more readily understood, certain terms are first defined. Additional definitions are set forth throughout the detailed description.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present disclosure are generally performed according to methods well known in the art and as described in various general and more specific references that are cited and discussed throughout the present specification unless otherwise indicated. Such references include, e.g., Sambrook and Russell, *Molecular Cloning, A Laboratory Approach*, Cold Spring Harbor Press, Cold Spring Harbor, N.Y. (2001), Ausubel et al., *Current Protocols in Molecular Biology*, John Wiley & Sons, NY (2002), and Harlow and Lane *Antibodies: A Laboratory Manual*, Cold Spring Harbor Laboratory Press, Cold Spring Harbor, N.Y. (1990). Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)).

The terms "α5β1" and "integrin α5β1" are used interchangeably, and include variants, isoforms and species homologs of human α5β1. Native human α5β1, for example, is made up of the α5 subunit (which derives from a precursor sequence that is subsequently cleaved into two chains that are linked by a disulfide bond) (Genbank Accession No. P08648) and a β1 subunit (which derives from a precursor sequence that is subsequently processed into a mature form) (Genbank Accession No. P05556-1). The β1 subunit is known to exist as several isoforms produced by alternative splicing (see, e.g., Genbank Accession Nos. P05556-2, P05556-3, P05556-4, and P05556-5). The human α5β1 antibodies of the disclosure may, in certain cases, cross-react with α5β1 from species other than human. In other cases, the antibodies may be completely specific for human α5β1 and may not exhibit species or other types of cross-reactivity.

An "immune response", as would be understood by the skilled artisan, includes, but is not limited to, any detectable antigen-specific or allogenic activation of a helper T cell or cytotoxic T cell response, production of antibodies, T cell-mediated activation of allergic reactions, and the like. The term encompasses the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the α5β1 integrin.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. Within light and heavy chains, the variable and constant regions are joined by a "J" region of about 12 or more amino acids, with the heavy chain also including a "D" region of about 10 or more amino acids. See generally, Fundamental Immunology Ch. 7 (Paul, W., ed., $2^{nd}$ ed. Raven Press, N.Y. (1989)).

The term "antigen-binding portion" of an antibody (or simply "antibody portion"), as used herein, refers to one or more fragments of an antibody that retain the ability to specifically bind to an antigen (e.g., $\alpha5\beta1$). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$, and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments may be obtained using any suitable technique, including conventional techniques known to those with skill in the art, and the fragments may be screened for utility in the same manner as are intact antibodies.

An "isolated antibody", as used herein, is intended to refer to an antibody that is substantially free of other antibodies having different antigenic specificities (e.g., an isolated antibody that specifically binds $\alpha5\beta1$ is substantially free of antibodies that specifically bind antigens other than $\alpha5\beta1$). An isolated antibody that specifically binds $\alpha5\beta1$ may, however, have cross-reactivity to other antigens, such as $\alpha5\beta1$ molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The terms "human antibody", or "fully human antibody", as used herein, are intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure or antigen binding portions thereof may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "human monoclonal antibody" or "fully human monoclonal antibody" refer to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene, where the B cell is fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" or "class" refers to the antibody class (e.g., IgM or IgG) that is encoded by the heavy chain constant region genes. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans.

As used herein, "subclass" refers to the further specification within an isotype of the heavy chain constant region gene, such as, for example, the IgG1, IgG2, IgG3, or IgG4 subclasses within the IgG isotype.

As used herein, the term "compound" or "pharmaceutical compound" includes antibodies, antigen-binding portions thereof, immunoconjugates, and bispecific molecules.

The phrases "an antibody recognizing an antigen" and "an antibody specific for an antigen" are used interchangeably herein with the term "an antibody which binds specifically to an antigen."

The term "antibody dependent cellular cytotoxicity" or "ADCC" refers to a cell-mediated reaction in which non-specific cytotoxic cells (e.g. NK cells, neutrophils, macrophages, etc.) recognize antibody bound on a target cell and subsequently cause lysis of the target cell. Such cytotoxic cells that mediate ADCC generally express Fc receptors (FcR). The primary cells for mediating ADCC (NK cells) express FcγRIII, whereas monocytes express FcγRI, FcγRII, FcγRIII, and/or FcγRIV. FcR expression on hematopoietic cells is summarized in Ravetch and Kinet, *Annu. Rev. Immunol.*, 9:457-92 (1991). To assess ADCC activity of a molecule, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., *Proc. Natl. Acad. Sci.* (USA), 95:652-656 (1998).

The terms "Fc receptor" or "FcR" are used to describe a receptor that binds to the Fc region of an antibody where the Fc region comprises a hinge region and the $C_H2$ and $C_H3$ domains of the heavy chain. For example, the FcR can be a native sequence human FcR. The FcR can be one that binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see, Daeron, *Annu. Rev. Immunol.*, 15:203-234 (1997)). FcRs are reviewed in Ravetch and Kinet, *Annu. Rev. Immunol.*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *Immunol.*, 117:587 (1976) and Kim et al., J. Immunol., 24:249 (1994)). The primary FcR binding site on immunoglobulin Fc fragments resides in the hinge region between the $C_H1$ and $C_H2$ domains. This hinge region interacts with the FcR1-3 on various leukocytes and triggers these cells to attack the target (Wines et al., *J. Immunol.*, 164:5313-5318 (2000)). The hinge region encompasses, but is no limited to, the sequences described in U.S. Pat. No. 6,165,476.

The term "capable of inducing antibody dependent cellular cytotoxicity" refers to the ability of an agent, such as an antibody, to demonstrate ADCC as measured by assay(s) known to those of skill in the art. Such activity is typically characterized by the binding of the Fc region with various FcRs. Without being limited by any particular mechanism, those of skill in the art will recognize that the ability of an antibody to demonstrate ADCC can be, for example, by virtue of it subclass (such as IgG1 or IgG3), by mutations introduced into the Fc region, or by virtue of modifications to the carbohydrate patterns in the Fc region of the antibody. Such modifications are described, for example, in U.S. Patent Publication No. 2007-0092521.

The term "human antibody derivatives" refers to any modified form of the human antibody, e.g., a conjugate of the antibody and another agent or antibody.

The term "humanized antibody" is intended to refer to antibodies in which CDR sequences derived from the germ-line of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

By the phrase "specifically binds," as used herein, is meant a compound, e.g., a protein, a nucleic acid, an antibody, and the like, which recognizes and binds a specific molecule, but does not substantially recognize or bind other molecules in a sample. For instance, an antibody or a peptide inhibitor which recognizes and binds a cognate ligand (e.g., an anti-α5β1 antibody that binds with its cognate antigen, α5β1) in a sample, but does not substantially recognize or bind other molecules in the sample. Thus, under designated assay conditions, the specified binding moiety (e.g., an antibody or an antigen-binding portion thereof) binds preferentially to a particular target molecule, e.g., α5β1, and does not bind in a significant amount to other components present in a test sample. A variety of assay formats may be used to select an antibody that specifically binds a molecule of interest. For example, solid-phase ELISA immunoassay, immunoprecipitation, BIAcore, FACS, and Western blot analysis are among many assays that may be used to identify an antibody that specifically reacts with α5β1. Typically, a specific or selective reaction will be at least twice the background signal or noise and more typically more than 10 times the background, even more specifically, an antibody is said to "specifically bind" an antigen when the equilibrium dissociation constant ($K_D$) is $\leq 1$ µM, for example $\leq 100$ nM and, further for example, $\leq 10$ nM.

As used herein, an antibody that "specifically binds to human integrin α5β1" is intended to refer to an antibody that binds to human integrin α5β1 with a $K_D$ of $1 \times 10^{-7}$ M or less, $5 \times 10^{-8}$ M or less, $3 \times 10^{-8}$ M or less, $1 \times 10^{-8}$ M or less, or 5×M or less.

The term "$k_{on}$", as used herein, is intended to refer to the on-rate, or association rate of a particular antibody-antigen interaction, whereas the term "$k_{off}$" as used herein, is intended to refer to the off-rate, or dissociation rate of a particular antibody-antigen interaction. The term "$K_D$", as used herein, is intended to refer to the dissociation constant, which is obtained from the ratio of $k_{off}$ to $k_{on}$ (i.e., $k_{off}/k_{on}$) and is expressed as a molar concentration (M). $K_D$ values for antibodies can be determined using methods well established in the art. One method for determining the $K_D$ of an antibody is by using surface plasmon resonance, typically using a biosensor system such as a Biacore® system.

As used herein, the term "high affinity" for an IgG antibody refers to an antibody having a $K_D$ of $1 \times 10^{-7}$ M or less, $5 \times 10^{-8}$ M or less, or $5 \times 10^{-9}$ M or less for a target antigen. However, "high affinity" binding can vary for other antibody isotypes.

For example, "high affinity" binding for an IgM isotype refers to an antibody having a $K_D$ of $10^{-6}$ M or less, $10^{-7}$ M or less, or $10^{-8}$ M or less.

The term "compete", as used herein with regard to an antibody, refers to when a first antibody, or an antigen-binding portion thereof, competes for binding with a second antibody, or an antigen-binding portion thereof, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). For instance, cross-competing antibodies can bind to the epitope, or portion of the epitope, to which the antibodies as disclosed herein bind. Use of both competing and cross-competing antibodies is encompassed by the present disclosure. Regardless of the mechanism by which such competition or cross-competition occurs (e.g., steric hindrance, conformational change, or binding to a common epitope, or portion thereof, and the like), the skilled artisan would appreciate, based upon the teachings provided herein, that such competing and/or cross-competing antibodies are encompassed and can be useful for the methods disclosed herein.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. Conformational and nonconformational epitopes are distinguished in that the binding to the former, but not the latter, is lost in the presence of denaturing solvents.

"Glycoform" refers to a complex oligosaccharide structure comprising linkages of various carbohydrate units. Such structures are described in, e.g., *Essentials of Glycobiology* Varki et al., eds., Cold Spring Harbor Laboratory Press, Cold Spring Harbor, N.Y. (1999), which also provides a review of standard glycobiology nomenclature. Such glycoforms include, but are not limited to, G2, G1, G0, G-1, and G-2 (see, e.g., International Patent Publication No. WO 99/22764).

"Glycosylation pattern" is defined as the pattern of carbohydrate units that are covalently attached to a protein (e.g., the glycoform) as well as to the site(s) to which the glycoform(s) are covalently attached to the peptide backbone of a protein, more specifically to an immunoglobulin protein.

It is likely that antibodies expressed by different cell lines or in transgenic animals will have different glycoforms and/or glycosylation patterns compared with each other. However, all antibodies encoded by the nucleic acid molecules provided herein, or comprising the amino acid sequences provided herein are part of the present disclosure, regardless of the glycosylation of such antibodies.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

As used herein, to "treat" means reducing the frequency with which symptoms of a disease (i.e., tumor growth and/or metastasis, or other effect mediated by the numbers and/or activity of immune cells, and the like) are experienced by a patient. The term includes the administration of the compounds or agents of the present disclosure to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Various aspects of the disclosure are described in further detail in the following subsections.

Anti-α5β1 Antibodies

The antibodies of the disclosure are characterized by particular functional features or properties of the antibodies. For example, the antibodies bind specifically to human α5β1. Preferably, an antibody of the disclosure binds to α5β1 with high affinity, for example with a $K_D$ of $1 \times 10^{-7}$ M or less. Preferably, the antibody binds to human α5β1 with a $K_D$ of $5 \times 10^{-8}$ M or less, $2 \times 10^{-8}$ M or less, $5 \times 10^{-9}$ M or less, $4 \times 10^{-9}$ M or less, $3 \times 10^{-9}$ M or less, or $2.7 \times 10^{-9}$ M or less. Assays to evaluate the binding ability of the antibodies toward α5β1 are known in the art, including for example, ELISAs, Western blots, RIAs, and flow cytometry analysis. Suitable assays are described in detail in the Examples. The binding kinetics (e.g., binding affinity) of the antibodies also can be assessed by assays known in the art, such as by Biacore analysis.

The anti-α5β1 antibodies of the present disclosure are also capable of inducing antibody dependent cellular cytotoxicity (ADCC). Such functionality can be achieved, for example, by the use of a specific subclass (e.g. IgG1, IgG2, IgG3), including mutations to the Fc domain that can further enhance the level of ADCC activity of an antibody. Such mutations and methods of measuring ADCC are described further in the Examples.

Monoclonal Antibody 22B5

One illustrative antibody of the disclosure is the human monoclonal antibody 22B5, as described in Examples 1 and 2. The $V_H$ amino acid sequence of 22B5 is shown in FIG. 1B and is set forth in SEQ ID NO:7. The $V_L$ amino acid sequence of 22B5 is shown in FIG. 1D and is set forth in SEQ ID NO:8. As shown in FIG. 1B and FIG. 2, the heavy chain variable region of 22B5 comprises two mutations back to the human germline gene sequence. That is, 22B5 comprises one mutation from isoleucine to serine at amino acid residue number 30 (I30S) and a mutation from asparagine to serine at amino acid residue number 33 (N33S). As used herein, "22B5" refers to the antibody wherein said I30S and N33S heavy chain variable region germline mutations have been made.

Given that 22B5 can bind to α5β1, the $V_H$ and $V_L$ sequences can be "mixed and matched" with other anti-α5β1 antibodies to create additional anti-α5β1 binding molecules of the disclosure. α5β1 binding of such "mixed and matched" antibodies can be tested using the binding assays described above and in the Examples (e.g., ELISAs). In one case, when $V_H$ and $V_L$ chains are mixed and matched, a $V_H$ sequence from a particular $V_H/V_L$ pairing is replaced with a structurally similar $V_H$ sequence. Likewise, in another case a $V_L$ sequence from a particular $V_H/V_L$ pairing is replaced with a structurally similar $V_L$ sequence.

In another aspect, the disclosure provides antibodies that comprise the heavy chain and light chain CDR1s, CDR2s and CDR3s of 22B5. The amino acid sequence of the $V_H$ CDR1 of 22B5 is shown in SEQ ID NO: 1. The amino acid sequence of the $V_H$ CDR2 of 22B5 is shown in SEQ ID NO: 2. The amino acid sequence of the $V_H$ CDR3 of 22B5 is shown in SEQ ID NO: 3. The amino acid sequence of the $V_L$ CDR1 of 22B5 is shown in SEQ ID NO 4. The amino acid sequence of the $V_L$ CDR2 of 22B5 is shown in SEQ ID NO: 5. The amino acid sequence of the $V_L$ CDR3 of 22B5 is shown in SEQ ID NO: 6. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that 22B5 binds to α5β1 and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" (i.e., CDRs from different α5β1 antibodies can be mixed and matched, although each antibody will typically contain a $V_H$ CDR1, CDR2, and CDR3 and a $V_L$ CDR1, CDR2, and CDR3) to create additional anti-α5β1 binding molecules of the disclosure. α5β1 binding of such "mixed and matched" antibodies can be tested using the binding assays described above and in the Examples (e.g., ELISAs, Biacore analysis). In one case, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence typically is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein.

Accordingly, in another aspect, the disclosure provides an isolated monoclonal antibody, or antigen binding portion thereof comprising: (a) a heavy chain variable region CDR1 comprising the amino acid sequence of SEQ ID NO: 1; (b) a heavy chain variable region CDR2 comprising the amino acid sequence of SEQ ID NO: 2; (c) a heavy chain variable region CDR3 comprising the amino acid sequence of SEQ ID NO: 3; (d) a light chain variable region CDR1 comprising the amino acid sequence of SEQ ID NO: 4; (e) a light chain variable region CDR2 comprising the amino acid sequence of SEQ ID NO: 5; and/or (f) a light chain variable region CDR3 comprising the amino acid sequence of SEQ ID NO: 6; wherein the antibody specifically binds α5β1, preferably human α5β1.

Monoclonal Antibodies 2D2, 24C7 and 1D9

Another illustrative antibody of the disclosure is the human monoclonal antibody 2D2, described in Examples 1 and 8. The $V_H$ amino acid sequence of 2D2 is shown in SEQ ID NO: 39. The $V_L$ amino acid sequence of 2D2 is shown in SEQ ID NO: 40.

Another illustrative antibody of the disclosure is the human monoclonal antibody 24C7, described in Examples 1 and 8. The $V_H$ amino acid sequence of 24C7 is shown in SEQ ID NO: 19. The $V_L$ amino acid sequence of 24C7 is shown in SEQ ID NO: 20.

Another illustrative antibody of the disclosure is the human monoclonal antibody 1D9, described in Examples 1 and 8. The $V_H$ amino acid sequence of 1D9 is shown in SEQ ID NO: 29. The $V_L$ amino acid sequence of 1D9 is shown in SEQ ID NO: 30.

Given that 2D2, 24C7, and 1D9 can bind to α5β1, the $V_H$ and $V_L$ sequences of these antibodies can be "mixed and matched" with other anti-α5β1 antibodies to create additional anti-α5β1 binding molecules of the disclosure. α5β1 binding of such "mixed and matched" antibodies can be tested using the binding assays described above and in the Examples (e.g., ELISAs). In one case, when $V_H$ and $V_L$ chains are mixed and matched, a $V_H$ sequence from a particular $V_H$/$V_L$ pairing is replaced with a structurally similar $V_H$ sequence. Likewise, in another case a $V_L$ sequence from a particular $V_H$/$V_L$ pairing is replaced with a structurally similar $V_L$ sequence.

In another aspect, the disclosure provides antibodies that comprise the heavy chain and light chain CDR1s, CDR2s and CDR3s of 2D2, 24C7, and 1D9. The corresponding amino acid sequences of these CDRs are indicated below.

| Antibody | CDR | SEQ ID NO: |
|---|---|---|
| 2D2 | $V_H$ CDR1 | 33 |
| 2D2 | $V_H$ CDR2 | 34 |
| 2D2 | $V_H$ CDR3 | 35 |
| 2D2 | $V_L$ CDR1 | 36 |
| 2D2 | $V_L$ CDR2 | 37 |
| 2D2 | $V_L$ CDR3 | 38 |
| 24C7 | $V_H$ CDR1 | 13 |
| 24C7 | $V_H$ CDR2 | 14 |
| 24C7 | $V_H$ CDR3 | 15 |
| 24C7 | $V_L$ CDR1 | 16 |
| 24C7 | $V_L$ CDR2 | 17 |
| 24C7 | $V_L$ CDR3 | 18 |
| 1D9 | $V_H$ CDR1 | 23 |
| 1D9 | $V_H$ CDR2 | 24 |
| 1D9 | $V_H$ CDR3 | 25 |
| 1D9 | $V_L$ CDR1 | 26 |
| 1D9 | $V_L$ CDR2 | 27 |
| 1D9 | $V_L$ CDR3 | 28 |

The CDR regions are delineated using the Kabat system (Kabat, E. A., et al. (1991) Sequences of Proteins of Immunological. Interest, Fifth Edition, U.S. Department of Health and Human Services, NIH Publication No. 91-3242).

Given that 2D2, 24C7 and 1D9 bind to α5β1 and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" (i.e., CDRs from different α5β1 antibodies can be mixed and matched, although each antibody will typically contain a $V_H$ CDR1, CDR2, and CDR3 and a $V_L$ CDR1, CDR2, and CDR3) to create additional anti-α5β1 binding molecules of the disclosure. α5β1 binding of such "mixed and matched" antibodies can be tested using the binding assays described above and in the Examples (e.g., ELISAs, Biacore analysis). In one case, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence typically is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein.

Accordingly, in another aspect, the disclosure provides an isolated monoclonal antibody, or antigen binding portion thereof comprising: (a) a heavy chain variable region CDR1 comprising the amino acid sequence of SEQ ID NO: 33; (b) a heavy chain variable region CDR2 comprising the amino acid sequence of SEQ ID NO: 34; (c) a heavy chain variable region CDR3 comprising the amino acid sequence of SEQ ID NO:

35; (d) a light chain variable region CDR1 comprising the amino acid sequence of SEQ ID NO: 36; (e) a light chain variable region CDR2 comprising the amino acid sequence of SEQ ID NO: 37; and/or (f) a light chain variable region CDR3 comprising the amino acid sequence of SEQ ID NO: 38; wherein the antibody specifically binds α5β1, preferably human α5β1.

In another aspect, the disclosure provides an isolated monoclonal antibody, or antigen binding portion thereof comprising: (a) a heavy chain variable region CDR1 comprising the amino acid sequence of SEQ ID NO: 13; (b) a heavy chain variable region CDR2 comprising the amino acid sequence of SEQ ID NO: 14; (c) a heavy chain variable region CDR3 comprising the amino acid sequence of SEQ ID NO: 15; (d) a light chain variable region CDR1 comprising the amino acid sequence of SEQ ID NO: 16; (e) a light chain variable region CDR2 comprising the amino acid sequence of SEQ ID NO: 17; and/or (f) a light chain variable region CDR3 comprising the amino acid sequence of SEQ ID NO: 18; wherein the antibody specifically binds α5β1, preferably human α5β1.

In another aspect, the disclosure provides an isolated monoclonal antibody, or antigen binding portion thereof comprising: (a) a heavy chain variable region CDR1 comprising the amino acid sequence of SEQ ID NO: 23; (b) a heavy chain variable region CDR2 comprising the amino acid sequence of SEQ ID NO: 24; (c) a heavy chain variable region CDR3 comprising the amino acid sequence of SEQ ID NO: 25; (d) a light chain variable region CDR1 comprising the amino acid sequence of SEQ ID NO: 26; (e) a light chain variable region CDR2 comprising the amino acid sequence of SEQ ID NO: 27; and/or (f) a light chain variable region CDR3 comprising the amino acid sequence of SEQ ID NO: 28; wherein the antibody specifically binds α5β1, preferably human α5β1.

Antibodies Having Particular Germline Sequences

In certain aspects, an antibody of the disclosure comprises a heavy chain variable region from a particular germline heavy chain immunoglobulin gene and/or a light chain variable region from a particular germline light chain immunoglobulin gene.

For example, in one aspect, the disclosure provides an isolated monoclonal antibody, or an antigen-binding portion thereof, comprising a heavy chain variable region that is the product of or derived from a human $V_H$ 4-39 gene, wherein the antibody specifically binds α5β1. In another aspect, the disclosure provides and isolated monoclonal antibody, or an antigen-binding portion thereof, comprising a heavy chain variable region that is the product of or derived from a human $V_H$ 3-30.3 gene, wherein the antibody specifically binds α5β1. In yet another aspect, the disclosure provides an isolated monoclonal antibody, or an antigen-binding portion thereof, comprising a light chain variable region that is the product of or derived from a human $V_K$ L6 gene, wherein the antibody specifically binds α5β1. In yet another illustrative aspect, the disclosure provides an isolated monoclonal antibody, or antigen-binding portion thereof, wherein the antibody:

(a) comprises a heavy chain variable region that is the product of or derived from a human VH 4-39 gene (which gene encodes the amino acid sequence set forth in SEQ ID NO: 7) or a human 3-30.3 gene (which gene encodes the amino acid sequence set forth in SEQ ID NOs: 19, 29, or 39);

(b) comprises a light chain variable region that is the product of or derived from a human $V_K$ L6 gene (which gene encodes the amino acid sequence set forth in SEQ ID NOs: 8, 20, 30, or 40); and (c) specifically binds to α5β1, preferably human α5β1.

An example of an antibody having $V_H$ and $V_L$ of $V_H$ 4-39 and $V_K$ L6, respectively, is 22B5. Examples of antibodies having $V_H$ and $V_L$ of $V_H$ 3-30.3 and $V_K$ L6, respectively, are 24C7, 2D2, and 1D9.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. In certain cases, the human antibody is identical in amino acid sequence to the amino acid sequence encoded by the germline Ig gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another aspect, an antibody of the disclosure comprises heavy and light chain variable regions comprising amino acid sequences that are homologous to the amino acid sequences of the illustrative antibodies described herein, and wherein the antibodies retain the desired functional properties of the anti-α5β1 antibodies of the disclosure.

For example, the disclosure provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 7, 19, 29, and 39;

(b) the light chain variable region comprises an amino acid sequence that is at least 80% homologous to the amino acid sequence selected from the group consisting of SEQ ID NOs: 8, 20, 30, and 40; and the antibody exhibits one or more of the following properties:
(i) the antibody binds to human α5β1 with a $K_D$ of $1×10^{-7}$ M or less;
(ii) the antibody is capable of inducing antibody dependent cellular cytotoxicity.

In various examples, the antibody can be, for example, a human antibody, a humanized antibody or a chimeric antibody.

In other examples, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 7, 19, 29, 39, 8, 20, 30, and/or 40, followed by testing of the encoded altered antibody for retained function (i.e., the properties set forth in (i) and/or (ii) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the disclosure. To obtain gapped alignments for comparison purposes, Gapped BLAST can be utilized as described in Altschul et al., (1997) *Nucleic Acids Res.* 25 (17):3389-3402. When utilizing BLAST and Gapped BLAST programs, the default parameters of the respective programs (e.g., XBLAST and NBLAST) can be used. See http://www.ncbi.nlm.nih.gov.

Antibodies with Conservative Modifications

In certain cases, an antibody of the disclosure comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the illustrative antibodies described herein (e.g., 22B5, 1D9, 24C7, and 2D2), or conservative modifications thereof, and wherein the antibodies retain one or more of the desired functional properties of the anti-α5β1 antibodies of the disclosure. Accordingly, the disclosure provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of SEQ ID NOs: 3, 15, 25, and 35, and conservative modifications thereof;
(b) the light chain variable region CDR3 sequence comprises an amino acid sequence selected from the group consisting of SEQ ID NOs: 6, 18, 28, and 38, and conservative modifications thereof; and the antibody exhibits one or more of the following properties:
(i) the antibody binds to human α5β1 with a $K_D$ of $1×10^{-7}$ M or less;
(ii) the antibody is capable of inducing antibody dependent cellular cytotoxicity.

In other cases, the heavy chain variable region CDR2 sequence comprises an amino acid sequence selected from the group consisting of SEQ ID NOs: 2, 14, 24, and 34, and conservative modifications thereof; and the light chain variable region CDR2 sequence comprises an amino acid sequence selected from the group consisting of SEQ ID NOs: 5, 17, 27, and 37, and conservative modifications thereof. In another case, the heavy chain variable region CDR1 sequence comprises an amino acid sequence selected from the group consisting of SEQ ID NOs: 1, 13, 23, and 33, and conservative modifications thereof; and the light chain variable region CDR1 sequence comprises an amino acid sequence selected from the group consisting of SEQ ID NOs: 4, 16, 26, and 36, and conservative modifications thereof.

As used herein, the term "conservative modification" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative modification of a given sequence can include those sequences that are at least 80%, at least 85%, at least 90%, at least 95%, at least 97%, at least 98%, or at least 99% identical to that sequence. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the properties set forth in (i) through (ii) above) using the functional assays described herein. Another type of amino acid modification is to eliminate asparagine-glycine pairs, which form potential deamidation sites, by altering one or both of the residues. In another example, the C-terminal lysine of the heavy chain of an α5β1 antibody of the disclosure has been cleaved, and is thus not present. The C-terminal lysine cleavage can be engineered in advance, or may result from the conditions used to express and purify the antibody. In various cases, the heavy and light chains of the α5β1 antibodies may optionally include a signal sequence.

Antibodies that Bind the Same Epitope as the Illustrative Anti-α5β1 Antibodies of the Disclosure In another aspect, the disclosure provides antibodies that bind to the same epitope on human α5β1 as any of the illustrative α5β1 monoclonal antibodies of the disclosure (i.e., antibodies that have the ability to cross-compete for binding to α5β1 with any of the monoclonal antibodies of the disclosure). For example, the reference antibody for cross-competition studies can be the monoclonal antibody 22B5 (having $V_H$ and $V_L$ sequences as shown in SEQ ID NOs: 7 and 8, respectively), or the monoclonal antibody 24C7 (having $V_H$ and $V_L$ sequences as shown in SEQ ID NOs: 19 and 20, respectively), or the monoclonal antibody 1D9 (having $V_H$ and $V_L$ sequences as shown in SEQ ID NOs: 29 and 30, respectively), or the monoclonal antibody 2D2 (having $V_H$ and $V_L$ sequences as shown in SEQ ID NOs: 39 and 40, respectively). Such cross-competing antibodies can be identified based on their ability to cross-compete with 22B5, 24C7, 1D9, or 2D2 in standard α5β1 binding assays. For example, BIAcore analysis, ELISA assays or flow cytometry may be used to demonstrate cross-competition with the illustrative antibodies of the current disclosure. The ability of a test antibody to inhibit the binding of, for example, 22B5, 24C7, 1D9, or 2D2 to human α5β1 demonstrates that the test antibody can compete with 22B5, 24C7, 1D9, or 2D2 for binding to human α5β1 and thus binds to the same epitope on human α5β1 as 22B5, 24C7, 1D9, or 2D2. In one case, the antibody that binds to the same epitope on human α5β1 as 22B5, 24C7, 1D9, or 2D2 is a human monoclonal antibody. Such human monoclonal antibodies can be prepared and isolated as described, for example, in the Examples.

Engineered and Modified Antibodies

An antibody, or antigen binding portion thereof, of the disclosure further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. Sci. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another aspect of the disclosure pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 1, 13, 23, and 33, SEQ ID NOs: 2, 14, 24, and 34, and SEQ ID NOs: 3, 15, 25, and 35, respectively, and a light chain variable region comprising CDR1, CDR2, and CDR3 sequences comprising an amino acid sequence selected from the group consisting of SEQ ID NOs: 4, 16, 26, and 36, SEQ ID NOs: 5, 17, 27, and 37, and SEQ ID NOs: 6, 18, 28, and 38, respectively. Thus, such antibodies contain the $V_H$ and $V_L$ CDR sequences of the monoclonal antibodies 22B5, 24C7, 1D9, and 2D2, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991), Sequences of Proteins of Immunological Interest, Fifth Edition, U.S. Department of Health and Human Services, NIH Publication No. 91-3242; Tomlinson, I. M., et al. (1992), *J. Mol. Biol.* 227:776-798; and Cox, J. P. L. et al. (1994), *Eur. J. Immunol.* 24:827-836; the contents of each of which are expressly incorporated herein by reference). As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo12 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (X92283), and 3-23 (AJ406678).

Framework sequences for use in the antibodies of the disclosure include, but are not limited to, those that are structurally similar to the framework sequences used by selected antibodies of the disclosure, e.g., similar to the $V_H$ 4-39 and/or the $V_H$ 3-30.3 framework sequences and/or the $V_K$ L6 framework sequences used by illustrative monoclonal antibodies of the disclosure. For example, the $V_H$ CDR1, CDR2, and CDR3 sequences, and the $V_L$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Typically, conservative modifications (as discussed above) are introduced. The mutations may be amino acid substitutions, additions or deletions. Moreover, typically no more than one, two, three, four or five residues within a CDR region are altered.

Accordingly, in another embodiment, the disclosure provides isolated anti-α5β1 monoclonal antibodies, or antigen binding portions thereof, comprising a heavy chain variable region comprising: (a) a $V_H$ CDR1 region comprising an amino acid sequence selected from the group consisting of SEQ ID NOs: 1, 13, 23, and 33 and an amino acid sequence having one, two, three, four or five amino acid substitutions, deletions or additions as compared to SEQ ID NOs: 1, 13, 23, or 33; (b) a $V_H$ CDR2 region comprising an amino acid sequence selected from the group consisting of SEQ ID NOs: 2, 14, 24, and 34, and an amino acid sequence having one, two, three, four or five amino acid substitutions, deletions or additions as compared to SEQ ID NOs: 2, 14, 24, or 34; (c) a $V_H$ CDR3 region comprising an amino acid sequence selected from the group consisting of SEQ ID NOs: 3, 15, 25, and 35, and an amino acid sequence having one, two, three, four or five amino acid substitutions, deletions or additions as compared to SEQ ID NOs: 3, 15, 25, or 35; (d) a $V_L$ CDR1 region comprising an amino acid sequence selected from the group consisting of SEQ ID NOs: 4, 16, 26, and 36, and an amino acid sequence having one, two, three, four or five amino acid substitutions, deletions or additions as compared to SEQ ID NOs: 4, 16, 26, or 36; (e) a $V_L$ CDR2 region comprising an amino acid sequence selected from the group consisting of SEQ ID NOs: 5, 17, 27, and 37, and an amino acid sequence having one, two, three, four or five amino acid substitutions, deletions or additions as compared to SEQ ID NOs: 5, 17, 27, or 37; and (f) a $V_L$ CDR3 region comprising an amino acid sequence selected from the group consisting of SEQ ID NOs: 6, 18, 28, and 38, and an amino acid sequence having one, two, three, four or five amino acid substitutions, deletions or additions as compared to SEQ ID NOs: 6, 18, 28, or 38.

Engineered antibodies of the disclosure include those in which modifications have been made to framework residues within $V_H$ and/or $V_L$, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Can et al.

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure may be chemically modified (e.g., one or more chemical moieties can be attached to the antibody) or be modified to alter its glycosylation, again to alter one or more functional properties of the antibody. Each of these aspects is described in further detail below. The numbering of residues in the Fc region is that of the EU index of Kabat.

In one case, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another case, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another case, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other cases, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another case, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A. For example, the 22B5/DLE antibody described herein uses the IgG1 subclass of the IgG isotype, but has incorporated the following mutations (as compared to the wild-type IgG1 subclass) through site-directed mutagenesis: S247D; A338L; and I340E. Similarly, as described in more detail below, such S247D, A338L, and I340E mutations have been introduced into the 24C7, 1D9 and 2D2 monoclonal antibodies. As described further in the Examples, such mutations can increase the antibody's affinity to Fcγ receptors and thus increase its effector function. Thus, the disclosure provides an antibody that comprises at least one mutation in the Fc region and has detectably greater ADCC response than an otherwise identical antibody not comprising the at least one mutation.

In still another example, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by the disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Typically, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain cases, the antibody to be pegylated is an aglycosylated antibody. Methods for pegylating proteins are known in the art and can be applied to the antibodies of the disclosure. See for example, EP 0 154 316 by Nishimura et al. and EP 0 401 384 by Ishikawa et al.

Methods of Engineering Antibodies

As discussed above, the anti-α5β1 antibodies having $V_H$ and $V_L$ sequences disclosed herein can be used to create new anti-α5β1 antibodies by modifying the $V_H$ and/or $V_L$ sequences, or the constant region(s) attached thereto. Thus, in another aspect of the disclosure, the structural features of an anti-α5β1 antibody of the disclosure, e.g. 22B5, 24C7, 1D9, or 2D2 are used to create structurally related anti-α5β1 antibodies that retain at least one functional property of the antibodies of the disclosure, such as binding to human α5β1. For example, one or more CDR regions of 22B5, 24C7, 1D9, or 2D2, or mutations thereof, can be combined recombinantly with known framework regions and/or other CDRs to create additional, recombinantly-engineered, anti-α5β1 antibodies of the disclosure, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) may be used as the starting material to create a "second generation" sequence(s) derived from the original sequence(s) and then the "second generation" sequence(s) is prepared and expressed as a protein.

Accordingly, in another aspect, the disclosure provides a method for preparing an anti-α5β1 antibody comprising:

(a) providing: (i) a heavy chain variable region antibody sequence comprising a CDR1 sequence selected from the group consisting of SEQ ID NOs: 1, 13, 23, and 33, a CDR2 sequence selected from the group consisting of SEQ ID NOs: 2, 14, 24, and 34, and/or a CDR3 sequence selected from the group consisting of SEQ ID NOs: 3, 15, 25, and 35; and/or (ii) a light chain variable region antibody sequence comprising a CDR1 sequence selected from the group consisting of SEQ ID NOs: 4, 16, 26, and 36, a CDR2 sequence selected from the group consisting of SEQ ID NOs: 5, 17, 27, and 37, and/or a CDR3 sequence selected from the group consisting of SEQ ID NOs: 6, 18, 28, and 38;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-α5β1 antibodies described herein, which functional properties include, but are not limited to:

(i) binds to human α5β1 with a $K_D$ of $1 \times 10^{-7}$ M or less;

(ii) is capable of inducing ADCC.

The functional properties of the altered antibodies can be assessed using standard assays available in the art and/or described herein, such as those set forth in the Examples (e.g., flow cytometry, binding assays).

In certain aspects of the methods of engineering antibodies of the disclosure, mutations can be introduced randomly or selectively along all or part of an anti-α5β1 antibody coding sequence and the resulting modified anti-α5β1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Disclosure

Another aspect of the disclosure pertains to nucleic acid molecules that encode the antibodies of the disclosure. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by any suitable techniques, including alkaline/SDS treatment, CsCl banding, column chromatography, agarose gel electrophoresis and others. See, F. Ausubel, et al., ed. (1987) Current Protocols in Molecular Biology, Greene Publishing and Wiley Interscience, New York. A nucleic acid of the disclosure can be, for example, DNA or RNA and may or may not contain intronic sequences. Typically, the nucleic acid is a cDNA molecule.

Nucleic acids of the disclosure can be obtained using any suitable molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by PCR amplification or cDNA cloning techniques. For antibodies obtained from an immunoglobulin gene library (e.g., using phage display techniques), nucleic acid encoding the antibody can be recovered from the library.

Nucleic acid molecules of the disclosure include, for example, those encoding the $V_H$ and $V_L$ sequences of the 22B5 monoclonal antibody. The DNA sequence encoding the $V_H$ sequence of 22B5 is shown in SEQ ID NO: 11. The DNA sequence encoding the $V_L$ sequence of 22B5 is shown in SEQ ID NO: 12. Other illustrative nucleic acid molecules disclosed herein are those encoding the $V_H$ and $V_L$ sequences of the 24C7, 1D9, and 2D2 monoclonal antibodies. The DNA sequence encoding the $V_H$ sequence of 24C7 is shown in SEQ ID NO: 21. The DNA sequence encoding the VL sequence of 24C7 is shown in SEQ ID NO: 22. The DNA sequence encoding the $V_H$ sequence of 1D9 is shown in SEQ ID NO: 31. The DNA sequence encoding the VL sequence of 1D9 is shown in SEQ ID NO: 32. The DNA sequence encoding the $V_H$ sequence of 2D2 is shown in SEQ ID NO: 41. The DNA sequence encoding the VL sequence of 2D2 is shown in SEQ ID NO: 42.

Once DNA fragments encoding $V_H$ and $V_L$ segments are obtained, these DNA fragments can be further manipulated by any suitable recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. The IgG1 constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly$_4$-Ser)$_3$, such that the V$_H$ and V$_L$ sequences can be expressed as a contiguous single-chain protein, with the V$_L$ and V$_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of the Disclosure

Monoclonal antibodies (mAbs) of the present disclosure can be produced by a variety of techniques, including conventional monoclonal antibody methodology e.g., the standard somatic cell hybridization technique of Kohler and Milstein (1975) *Nature* 256: 495. Other techniques for producing monoclonal antibody also can be employed, e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using suitable molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In some cases, the antibodies of the disclosure are human monoclonal antibodies. Such human monoclonal antibodies directed against α5β1 can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). Preparation and use of the HuMAb Mouse®, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology:* 579-591; and Fishwild, D. et al. (1996) *Nature Biotechnology* 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another case, human antibodies of the disclosure can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-α5β1 antibodies of the disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-α5β1 antibodies of the disclosure. For example, mice carrying both a human heavy chain transchromosome and a human light chain transchromosome, referred to as "TC mice" can be used; such mice are described in Tomizuka et al. (2000) *Proc. Natl. Acad Sci. USA* 97:722-727. Furthermore, cows carrying human heavy and light chain transchromosomes have been described in the art (Kuroiwa et al. (2002) *Nature Biotechnology* 20:889-894) and can be used to raise anti-α5β1 antibodies of the disclosure.

Human monoclonal antibodies of the disclosure can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the disclosure, such mice can be immunized with a purified or enriched preparation of α5β1 antigen and/or recombinant α5β1, or an α5β1 fusion protein, as described by Lonberg, N. et al. (1994) *Nature* 368 (6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 μg) of α5β1 antigen can be used to immunize the human Ig mice intraperitoneally. Moreover, polypeptide fragments of the relevant proteins, e.g., α5 and/or β1, may be used to immunize the mice. For example, the polypeptide fragments may be conjugated to a carrier molecule to increase their immunogenicity. Such carrier molecules are well-known in the art, and include keyhole limpet hemocyanin, bovine serum albumin, thyroglobulin, diphtheria toxoid, and tetanus toxoid, among others.

Detailed procedures to generate fully human monoclonal antibodies to α5β1 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-α5β1 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse® strain can be used, as described in Example 1.

Generation of Hybridomas Producing Human Monoclonal Antibodies

To generate hybridomas producing human monoclonal antibodies of the disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies

Antibodies of the disclosure also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma or phage that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by any suitable methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype and subclass by inserting them into expression vectors already encoding heavy chain constant and light chain constant regions of the desired isotype and subclass such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure typically carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SR promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr− host cells with methotrexate selection/amplification) and the neo gene (for G418 selection).

For expression of the light and heavy chains, the expression vector(s) encoding the heavy and light chains is transfected into a host cell by any suitable techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the disclosure in either prokaryotic or eukaryotic host cells, expression of antibodies in eukaryotic cells, and typically mammalian host cells, is most typical.

Mammalian host cells for expressing the recombinant antibodies of the disclosure include, for example, Chinese Hamster Ovary (CHO) cells (including dhfr− CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and Sp2 cells. In particular, for use with NS0 myeloma or CHO cells, another expression system is the GS (glutamine synthetase) gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using any suitable protein purification methods.

Characterization of Antibody Binding to Antigen

Antibodies, or antigen binding portions thereof, of the disclosure can be tested for binding to α5β1 by, for example, standard ELISA. Briefly, microtiter plates are coated with purified α5β1 at 0.25 μg/ml in PBS, and then blocked with 5% bovine serum albumin in PBS. Dilutions of antibody (e.g., dilutions of plasma from α5β1-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with α5β1 immunogen. Hybridomas that bind with high avidity to α5β1 are subcloned and further characterized. One clone from each hybridoma, which retains the reactivity of the parent cells (by ELISA), can be chosen for making a 5 to 10 vial cell bank stored at −140° C., and for antibody purification.

To purify anti-α5β1 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Further, the epitope bound by the antibody can be characterized by standard methods known in the art. Such methods include producing an array of overlapping peptide fragments of α5 and/or β1 and assessing the binding of the antibody to the various fragments. Alternatively, mutations, e.g., alanine-scanning mutagenesis where each amino acid, is replaced by an alanine residue, can be introduced into the α5 and/or β1 peptide and the binding of the antibody to the mutant peptide can be compared with binding of the antibody to the wild type protein, and thereby identify sites where mutation(s) affect binding. See, e.g., Cunningham et al., (1989) *Science* 244: 1081-1085.

To determine if the selected anti-α5β1 monoclonal antibodies or antigen binding portion thereof bind to unique epitopes, each antibody can be biotinylated using commercially available reagents (Pierce, Rockford, Ill.). Competition studies using unlabeled monoclonal antibodies and biotinylated monoclonal antibodies can be performed using α5β1 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microliter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-α5β1 human IgGs can be further tested for reactivity with α5β1 antigen by Western blotting. Briefly, α5β1 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Immunoconjugates

In another aspect, the present disclosure features an anti-α5β1 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody, or antigen binding portion thereof, of the disclosure include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the disclosure or antigen binding portions thereof using various linker technologies. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies or antigen binding portions thereof of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for preparing radioimmunoconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the disclosure.

The antibody conjugates of the disclosure can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present disclosure features bispecific molecules comprising an anti-α5β1 antibody, or a fragment thereof, of the disclosure. An antibody of the disclosure, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the disclosure, an antibody of the disclosure can be functionally linked (e.g., by chemical coupling, genetic fusion, non-covalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for α5β1 and a second binding specificity for a second target epitope. In a particular aspect of the disclosure, the second target epitope is an Fc receptor, e.g., human FcγRI (CD64) or a human Fcγ receptor (CD89). Therefore, the disclosure includes bispecific molecules capable of binding both to FcγR or FcγR expressing effector cells (e.g., monocytes, macrophages or polymorphonuclear cells (PMNs)), and to target cells expressing α5β1. These bispecific molecules target α5β1 expressing cells to effector cell and trigger Fc receptor-mediated effector cell activities, such as phagocytosis of an α5β1 expressing cells, antibody dependent cell-mediated cytotoxicity (ADCC), cytokine release, or generation of superoxide anion.

In an aspect of the disclosure in which the bispecific molecule is multispecific, the molecule can further include a third binding specificity, in addition to an anti-Fc binding specificity and an anti-α5β1 binding specificity. In one case, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one case, the bispecific molecules of the disclosure comprise as a binding specificity at least one antibody, or an antibody fragment thereof, including, e.g., an Fab, Fab', $F(ab')_2$, Fv, or a single chain Fv. The antibody may also be a light chain or heavy chain dimer, or any minimal fragment thereof such as a Fv or a single chain construct as described in Ladner et al. U.S. Pat. No. 4,946,778.

In one case, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one case, the Fcγ receptor is a human high affinity Fcγ RI. The human FcγRI is a 72 kDa molecule, which shows high affinity for monomeric IgG ($10^8$-$10^9 M^{-1}$).

The production and characterization of certain anti-Fcγ monoclonal antibodies are described by Fanger et al. in PCT Publication WO 88/00052 and in U.S. Pat. No. 4,954,617. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this disclosure are mAb 22, mAb 32, mAb 44, mAb 62 and mAb 197. The hybridoma producing mAb 32 is available from the American Type Culture Collection, ATCC Accession No. HB9469. In other cases the anti-Fcγ receptor antibody is a humanized form of monoclonal antibody 22 (H22). The production and characterization of the 1122 antibody is described in Graziano, R. F. et al. (1995) *J. Immunol* 155 (10): 4996-5002 and PCT Publication WO 94/10332. The H22 antibody producing cell line was deposited at the American Type Culture Collection under the designation HA022CL1 and has the Accession No. CRL 11177.

In still other cases, the binding specificity for an Fc receptor is provided by an antibody that binds to a human IgA receptor, e.g., an Fc-alpha receptor (FcαRI (CD89)), the binding of which is typically not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7 M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are illustrative trigger receptors for use in the bispecific molecules of the disclosure because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the disclosure are murine, chimeric and humanized monoclonal antibodies.

The bispecific molecules of the present disclosure can be prepared by conjugating the constituent binding specificities, e.g., the anti-FcR and anti-α5β1 binding specificities, using any suitable methods. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) *Behring Ins. Mitt.* No. 78, 118-132; Brennan et al. (1985) *Science* 229:81-83), and Glennie et al. (1987) *J. Immunol.* 139:2367-2375). Suitable conjugating agents include SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In one case, the hinge region is modified to contain an odd number of sulfhydryl residues, such as one residue, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')₂ or ligand× Fab fusion protein. A bispecific molecule of the disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a γ counter or a scintillation counter or by autoradiography.

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g., two or more different) antibodies, or immunoconjugates or bispecific molecules of the disclosure. For example, a pharmaceutical composition of the disclosure can comprise a combination of antibodies (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include an anti-α5β1 antibody of the present disclosure combined with at least one other anti-inflammatory or immunosuppressant agent. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. Typically, the carrier is suitable for intravenous, intramuscular, subcutaneous, parenteral, spinal or epidermal administration (e.g., by injection or infusion). Depending on the route of administration, the active compound, i.e., antibody, antigen-binding portion thereof, immunoconjugate, or bispecific molecule, may be coated in a material to protect the compound from the action of acids and other natural conditions that may inactivate the compound.

In certain embodiments, the antibodies of the present disclosure may be present in a neutral form (including zwitter ionic forms) or as a positively or negatively-charged species. In some cases, the antibodies may be complexed with a counterion to form a pharmaceutically acceptable salt. Thus, the pharmaceutical compounds of the disclosure may include one or more pharmaceutically acceptable salts.

A "pharmaceutically acceptable salt" refers to a salt that retains the desired biological activity of the parent compound (e.g. antibody) and does not impart undesired toxicological effects (see e.g., Berge, S. M., et al. (1977) *J. Pharm. Sci.* 66:1-19). For example, the term "pharmaceutically acceptable salt" includes a complex comprising one or more antibodies and one or more counterions, where the counterions are derived from pharmaceutically acceptable inorganic and organic acids and bases.

Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Furthermore, pharmaceutically acceptable inorganic bases include metallic ions. Metallic ions include, but are not limited to, appropriate alkali metal salts, alkaline earth metal salts and other physiological acceptable metal ions. Salts derived from inorganic bases include aluminum, ammonium, calcium, cobalt, nickel, molybdenum, vanadium, manganese, chromium, selenium, tin, copper, ferric, ferrous, lithium, magnesium, manganic salts, manganous, potassium, rubidium, sodium, and zinc, and in their usual valences.

Pharmaceutically acceptable acid addition salts of the antibodies of the present disclosure can be prepared from the following acids, including, without limitation formic, acetic, acetamidobenzoic, adipic, ascorbic, boric, propionic, benzoic, camphoric, carbonic, cyclamic, dehydrocholic, malonic, edetic, ethylsulfuric, fendizoic, metaphosphoric, succinic, glycolic, gluconic, lactic, malic, tartaric, tannic, citric, nitric, ascorbic, glucuronic, maleic, folic, fumaric, propionic, pyruvic, aspartic, glutamic, benzoic, hydrochloric, hydrobromic, hydroiodic, lysine, isocitric, trifluoroacetic, pamoic, propionic, anthranilic, mesylic, orotic, oxalic, oxalacetic, oleic, stearic, salicylic, aminosalicylic, silicate, p-hydroxybenzoic, nicotinic, phenylacetic, mandelic, embonic, sulfonic, methanesulfonic, phosphoric, phosphonic, ethanesulfonic, ethanedisulfonic, ammonium, benzenesulfonic, pantothenic, naphthalenesulfonic, toluenesulfonic, 2-hydroxyethanesulfonic, sulfanilic, sulfuric, nitric, nitrous, sulfuric acid monomethyl ester, cyclohexylaminosulfonic, β-hydroxybutyric, glycine, glycylglycine, glutamic, cacodylate, diaminohexanoic, camphorsulfonic, gluconic, thiocyanic, oxoglutaric, pyridoxal 5-phosphate, chlorophenoxyacetic, undecanoic, N-acetyl-L-aspartic, galactaric and galacturonic acids.

Pharmaceutically acceptable organic bases include trimethylamine, diethylamine, N,N'-dibenzylethylenediamine, chloroprocaine, choline, dibenzylamine, diethanolamine, ethylenediamine, meglumine (N-methylglucamine), procaine, cyclic amines, quaternary ammonium cations, arginine, betaine, caffeine, clemizole, 2-ethylaminoethanol, 2-diethylaminoethanol, 2-dimethylaminoethanol, ethanediamine, butylamine, ethanolamine, ethylenediamine, N-ethylmorpholine, N-ethylpiperidine, ethylglucamine, glucamine, glucosamine, histidine, hydrabamine, imidazole, isopropylamine, methylglucamine, morpholine, piperazine, pyridine, pyridoxine, neodymium, piperidine, polyamine resins, procaine, purines, theobromine, triethylamine, tripropylamine, triethanolamine, tromethamine, methylamine, taurine, cholate, 6-amino-2-methyl-2-heptanol, 2-amino-2-methyl-1,3-propanediol, 2-amino-2-methyl-1-propanol, aliphatic mono- and dicarboxylic acids, phenyl-substituted alkanoic acids, hydroxy alkanoic acids, aromatic acids, aliphatic and aromatic sulfonic acids, strontium, tricine, hydrazine, phenylcyclohexylamine, 2-(N-morpholino)ethanesulfonic acid, bis(2-hydroxyethyl)amino-tris(hydroxymethyl)methane, N-(2-acetamido)-2-aminoethanesulfonic acid, 1,4-piperazinediethanesulfonic acid, 3-morpholino-2-hydroxypropanesulfonic acid, 1,3-bis[tris(hydroxymethyl)methylamino]propane, 4-morpholinepropanesulfonic acid, 4-(2-hydroxyethyl)piperazine-1-ethanesulfonic acid, 2-[(2-hydroxy-1,1-bis(hydroxymethyl)ethyl)amino]ethanesulfonic acid, N,N-bis(2-hydroxyethyl)-2-aminoethanesulfonic acid, 4-(N-morpholino)butanesulfonic acid, 3-(N,N-bis[2-hydroxyethyl]amino)-2-hydroxypropanesulfonic acid, 2-hydroxy-3-[tris(hydroxymethyl)methylamino]-1-propanesulfonic acid, 4-(2-hydroxyethyl)piperazine-1-(2-hydroxypropanesulfonic acid), piperazine-1,4-bis(2-hydroxypropanesulfonic acid) dihydrate, 4-(2-hydroxyethyl)-1-piperazinepropanesulfonic acid, N,N-bis(2-hydroxyethyl)glycine, N-(2-hydroxyethyppiperazine-N'-(4-butanesulfonic acid), N-[tris(hydroxymethyl)methyl]-3-aminopropanesulfonic acid, N-tris(Hydroxymethyl)methyl-4-aminobutanesulfonic acid, N-(1,1-dimethyl-2-hydroxyethyl)-3-amino-2-hydroxypropanesulfonic acid, 2-(cyclohexylamino) ethanesulfonic acid, 3-(cyclohexylamino)-2-hydroxy-1-propanesulfonic acid, 3-(cyclohexylamino)-1-propanesulfonic acid, N-(2-acetamido)iminodiacetic acid, 4-(cyclohexylamino)-1-butanesulfonic acid, N-[tris(hydroxymethyl)methyl]glycine, 2-amino-2-(hydroxymethyl)-1,3-propanediol, and trometamol.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation include, but are not limited to, vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1 to 10 mg/kg. An exemplary treatment regime entails administration once per week, once every two weeks, once every three weeks, once every four weeks, once per month, once every 3 months or once every three to 6 months. Dosage regimens for an anti-$\alpha5\beta1$ antibody or antigen binding portion thereof of the disclosure include, for example, 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1 to 1000 µg/ml and in some methods about 25 to 300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-α5β1 antibody of the disclosure preferably results in a decrease in severity of disease symptoms, an increase in frequency and duration of disease symptom-free periods, or a prevention of impairment or disability due to the disease affliction. For example, for the treatment of α5β1-positive tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Routes of administration for antibodies or antigen binding portions thereof of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody or antigen biding portion thereof of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, a therapeutic composition of the disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain case, the human monoclonal antibodies or antigen binding portions thereof of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V.

Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Disclosure

The antibodies, particularly the human antibodies, antibody compositions and methods of the present disclosure have numerous in vitro and in vivo diagnostic and therapeutic utilities involving the diagnosis and treatment of α5β1 mediated disorders. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles. Preferred subjects include human patients having disorders mediated by α5β1 activity. The methods are particularly suitable for treating human patients having a disorder associated with aberrant α5β1 expression. When antibodies to α5β1 are administered together with another agent, the two can be administered in either order or simultaneously.

Given the specific binding of the antibodies of the disclosure for α5β1, the antibodies of the disclosure can be used to specifically detect α5β1 expression on the surface of cells and, moreover, can be used to purify α5β1 via immunoaffinity purification.

Furthermore, given the expression of α5β1 on various tumor cells (see, e.g. Example 6, FIG. 7), and its involvement in angiogenesis, the human antibodies, antibody compositions and methods of the present disclosure can be used to treat a subject with abnormal cell growth, e.g., a disorder characterized by the presence of tumor cells expressing α5β1 including, for example, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non-Hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In one case, the antibodies (e.g., human monoclonal antibodies, multispecific and bispecific molecules and compositions) or antigen binding portions thereof of the disclosure can be used to detect levels of α5β1, or levels of cells which contain α5β1 on their membrane surface, which levels can then be linked to certain disease symptoms. Alternatively, the antibodies can be used to inhibit or block α5β1 function which, in turn, can be linked to the prevention or amelioration of certain disease symptoms, thereby implicating α5β1 as a mediator of the disease. This can be achieved by contacting a sample and a control sample with the anti-α5β1 antibody under conditions that allow for the formation of a complex between the antibody and α5β1. Any complexes formed between the antibody and α5β1 are detected and compared in the sample and the control.

In another case, the antibodies (e.g., human antibodies, multispecific and bispecific molecules and compositions) or antigen binding portions thereof of the disclosure can be initially tested for binding activity associated with therapeutic or diagnostic use in vitro. For example, compositions of the disclosure can be tested using the flow cytometric assays described in the Examples below.

The antibodies (e.g., human antibodies, multispecific and bispecific molecules, immunoconjugates and compositions) or antigen binding portions thereof of the disclosure have additional utility in therapy and diagnosis of α5β1-related diseases. For example, the human monoclonal antibodies, the multispecific or bispecific molecules and the immunoconjugates can be used to elicit in vivo or in vitro one or more of the following biological activities: to inhibit the growth of and/or kill a cell expressing α5β1; to mediate phagocytosis or ADCC of a cell expressing α5β1 in the presence of human effector cells, or to block α5β1 ligand binding to α5β1.

In a particular case, the antibodies (e.g., human antibodies, multispecific and bispecific molecules and compositions) or antigen binding portions thereof are used in vivo to treat, prevent or diagnose a variety of α5β1-related diseases. Examples of α5β1-related diseases include, among others, abnormal cell growth, such as cancer. In one embodiment, the abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non-Hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

Suitable routes of administering the antibody compositions (e.g., human monoclonal antibodies, multispecific and bispecific molecules and immunoconjugates) or antigen binding portions thereof of the disclosure in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-α5β1 antibodies or antigen binding portions thereof of the disclosure can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin can be intravenously administered as a 100 mg/dose once every four weeks and adriamycin is intravenously administered as a 60 to 75 mg/ml dose once every 21 days. Co-administration of the human anti-α5β1 antibodies, or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the disclosure can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$ to $10^9$ but will vary depending on the therapeutic purpose. In general, the amount will be sufficient to obtain localization at the target cell, e.g., a tumor cell expressing α5β1, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the disclosure and/or effector cells armed with these compositions can be used in conjunction with chemotherapy. Additionally, combination immunotherapy may be used to direct two distinct cytotoxic effector populations toward tumor cell rejection. For example, anti-α5β1 antibodies linked to anti-Fc-gamma RI or anti-CD3 may be used in conjunction with IgG- or IgA-receptor specific binding agents.

Bispecific and multispecific molecules of the disclosure can also be used to modulate FcγR or FcγR levels on effector cells, such as by capping and elimination of receptors on the cell surface. Mixtures of anti-Fc receptors can also be used for this purpose.

The compositions (e.g., human, humanized, or chimeric antibodies, multispecific and bispecific molecules and immunoconjugates) of the disclosure which have complement binding sites, such as portions from IgG1, -2, or -3 or IgM which bind complement, can also be used in the presence of complement. In one case, ex vivo treatment of a population of cells comprising target cells with a binding agent of the disclosure and appropriate effector cells can be supplemented by the addition of complement or serum containing complement. Phagocytosis of target cells coated with a binding agent of the disclosure can be improved by binding of complement proteins. In another case target cells coated with the compositions (e.g., human antibodies, multispecific and bispecific molecules) of the disclosure can also be lysed by complement. In yet another case, the compositions of the disclosure do not activate complement.

The compositions (e.g., human, humanized, or chimeric antibodies, multispecific and bispecific molecules and immunoconjugates) of the disclosure can also be administered together with complement. Accordingly, within the scope of the disclosure are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the disclosure and the complement or serum can be administered separately.

Also within the scope of the present disclosure are kits comprising the antibody compositions of the disclosure (e.g., human antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional human antibodies or antigen binding portions thereof of the disclosure (e.g., a human antibody having a complementary activity which binds to an epitope in the α5β1 antigen distinct from the first human antibody).

Accordingly, patients treated with antibody compositions of the disclosure can be additionally administered (prior to, simultaneously with, or following administration of a human antibody of the disclosure) another therapeutic agent, such as a cytotoxic or radiotoxic agent, which enhances or augments the therapeutic effect of the human antibodies.

In other cases, the subject can be additionally treated with an agent that modulates, e.g., enhances or inhibits, the expression or activity of Fcγ or Fcγ receptors by, for example, treating the subject with a cytokine. Cytokines for administration during treatment with the multispecific molecule include granulocyte colony-stimulating factor (G-CSF), granulocyte-macrophage colony-stimulating factor (GM-CSF), interferon-γ (IFN-γ), and tumor necrosis factor (TNF).

The compositions (e.g., human antibodies, multispecific and bispecific molecules) of the disclosure can also be used to target cells expressing FcγR or α5β1, for example for labeling such cells. For such use, the binding agent can be linked to a molecule that can be detected. Thus, the disclosure provides methods for localizing ex vivo or in vitro cells expressing Fc receptors, such as FcγR, or α5β1. The detectable label can be, e.g., a radioisotope, a fluorescent compound, an enzyme, or an enzyme co-factor.

In a particular case, the disclosure provides methods for detecting the presence of α5β1 antigen in a sample, or measuring the amount of α5β1 antigen, comprising contacting the sample, and a control sample, with a human monoclonal antibody, or an antigen binding portion thereof, which specifically binds to α5β1, under conditions that allow for formation of a complex between the antibody or portion thereof and α5β1. The formation of a complex is then detected, wherein a different complex formation between the sample compared to the control sample is indicative the presence of α5β1 antigen in the sample.

In other cases, the disclosure provides methods for treating an α5β1 mediated disorder in a subject, e.g., abnormal cell growth such as cancer, by administering to the subject the human antibodies or antigen binding portions thereof described above. Such antibodies and derivatives thereof are used to inhibit α5β1 induced activities associated with certain disorders, e.g., angiogenesis, proliferation, and differentiation. By contacting the antibody with α5β1 (e.g., by administering the antibody to a subject), the ability of α5β1 to induce such activities is inhibited and, thus, the associated disorder is treated. The antibody composition can be administered alone or along with another therapeutic agent, such as a cytotoxic or a radiotoxic agent which acts in conjunction with or synergistically with the antibody composition to treat or prevent the α5β1 mediated disease.

In yet another case, immunoconjugates of the disclosure can be used to target compounds (e.g., therapeutic agents, labels, cytotoxins, radiotoxoins immunosuppressants, etc.) to cells which have α5β1 cell surface receptors by linking such compounds to the antibody. Thus, the disclosure also provides methods for localizing ex vivo or in vivo cells expressing α5β1 (e.g., with a detectable label, such as a radioisotope, a fluorescent compound, an enzyme, or an enzyme co-factor). Alternatively, the immunoconjugates can be used to kill cells which have α5β1 cell surface receptors by targeting cytotoxins or radiotoxins to α5β1.

The present disclosure is further illustrated by the following examples which should not be construed as further limiting. The contents of all figures and all references, patents and published patent applications cited throughout this disclosure are expressly incorporated herein by reference in their entirety.

EXAMPLES

Example 1

Generation of a Hybridoma Producing Anti-α5β1 Antibody

Illustrative antibodies in accordance with the disclosure were prepared, selected, and assayed as follows:
Immunization and Hybridoma Generation:

The following immunogens were used for hybridoma generation: purified recombinant human integrin-α5 protein-Fc; integrin-α5-His (R&D Systems, custom order); NIH3T3 cells transfected to express human α5; a Jurkat cell line, a U-937 cell line (ATCC Cat No CRL-1593) and a K-562 cell line (ATCC Cat No CCL-243) which naturally express human integrin α5β1.

Purified recombinant human integrin-α5 protein-Fc is a chimeric construct of the extracellular domain of human integrin α5 (amino acids 42-995) fused to a rat Fc domain that was cloned into the pSecTag2 vector and expressed using the 293-FreeStyle system (Invitrogen). NIH3T3 cells, transfected to express human α5, were produced as follows. Full-length human integrin α5 cDNA (Invitrogen, Cat. No. FL1002, clone ID:3629647) was cloned from full-length human integrin α5 MGC clone (Invitrogen) and subcloned into a retrovirus expression vector (pBabe). The virus particles were generated and used to infect NIH3T3 cells (ATCC Cat No. CRL-1658). Puromycin was added to select for positive stable cell clones. Western Blot and FACS analyses of human α5 protein expression were performed to pick the high expression stable cell clones.

Fully human monoclonal antibodies to human integrin α5β1 were prepared using human Ig transgenic mouse strain Hco7/Hco12 as well as the human transchromosomal/transgenic strain, KM (Medarex, Inc.). These strains all express fully human antibodies that are indistinguishable from antibodies isolated from humans. In these mouse strains, the endogenous mouse kappa light chain gene has been homozygously disrupted as described in Chen et al. (1993) EMBO J. 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) Nature Biotechnology 14:845-851. The HCo7 strain carries the HCo7 human heavy chain transgene as described in U.S. Pat. Nos. 5,545,806, 5,625,825, and 5,545,807. The HCo12 strain carries the HCo12 human heavy chain transgene as described in Example 2 of PCT Publication WO 01/09187. The HCo7/HCo12 strain carries both the HCo7 and the HCo12 heavy chain transgenes. The KM strain carries a human mini-chromosome as described in Ishida et al., (2002), Cloning and Stem Cells, 4: 91-102.

To generate fully human monoclonal antibodies to α5β1, HuMab mice of Hco7/Hco12 and KM strains were immunized with recombinant human integrin-α5 protein-Fc or integrin-α5-His, NIH3T3 cells, transfected to express human α5, and Jurkat cell line, U-937 cell line and K-562 cell line which naturally express human α5β1. General immunization schemes for HuMab mice are described in Lonberg, N. et al (1994) Nature 368(6474): 856-859; Fishwild, D. et al. (1996) Nature Biotechnology 14: 845-851 and PCT Publication WO 98/24884. The mice were 6-16 weeks of age upon the first infusion of antigen. A purified recombinant preparation of human integrin-α5 protein-Fc or integrin-α5-his antigen (15-20 μg), a preparation of transfected NIH3T3 cells or Jurkat cells, U-937 cells, and K-562 cells ($1 \times 10^7$ cells) was used to immunize the HuMab mice intraperitoneally (IP) and subcutaneously (Sc).

Transgenic mice were immunized with antigen in Ribi adjuvant intraperitoneally and subcutaneously in 1-4 week intervals (up to a total of 16 immunizations). The immune response was monitored in blood taken by retro orbital bleeds. The serum was screened by FACS (as described below), and mice with sufficient titers of anti-α5β1 human immunoglobulin were used for fusions. Mice were boosted intravenously with antigen 3 and 2 days before sacrifice and removal of the spleen and/or lymph nodes. Typically, 10-20 fusions for each antigen were performed. A total of 60 Hco7/Hco12 and KM mice were immunized. Several dozen mice were immunized for each antigen.
Selection of HuMab Mice Producing Anti-α5β1 Antibodies:

To select HuMab mice producing antibodies that bound α5β1, sera from immunized mice were screened by flow cytometry (FACS) for binding to a cell line expressing full length human α5β1, and not to a control cell line not expressing α5β1. Briefly, α5-expressing NIH3T3 cells were incubated with serum from immunized mice diluted at 1:20. Cells were washed and specific antibody binding was detected with FITC-labeled anti-human IgG Ab. Flow cytometric analyses were performed on a FACS flow cytometry instrument (Becton Dickinson, San Jose, Calif.). Mice that developed the highest titers of anti-α5β1 antibodies were used for fusions. Fusions were performed as described below and hybridoma supernatants were tested for anti-α5β1 activity by FACS.

Generation of Hybridomas Producing Human Monoclonal Antibodies to α5β1:

The mouse splenocytes and/or lymph node lymphocytes, isolated from the HuMab mice, were fused using electrofusion (E-fusion, Cyto Pulse™ technology, Cyto Pulse™ Sciences, Inc., Glen Burnie, Md.) to the mouse myeloma cell line, Sp2/0 (ATCC, CRL-1581, Manassas, Va.), using manufacturer recommended protocols. Briefly, single cell suspensions of splenic and/or lymph node lymphocytes from immunized mice were fused to equal number of Sp2/0 nonsecreting mouse myeloma cells using E-fusion. Cells were plated at approximately $2\times10^4$ splenocytes/well in flat bottom microtiter plates, and incubated for 10 to 14 days in selective medium containing 10% fetal bovine serum, 10% P388D1 (ATCC, CRL-TIB-63) conditioned medium, 3 to 5% (IGEN) in DMEM (Mediatech, Herndon, Va., Cat. No. CRL 10013), with high glucose, L-glutamine and sodium pyruvate), 5 mM HEPES, 0.055 mM 2-mercaptoethanol, 50 mg/ml gentamycin and 1×HAT (Sigma, Cat. No. CRL-P-7185). After 1 to 2 weeks, cells were cultured in medium in which the HAT was replaced with HT. Approximately 10 to 14 days after cell plating supernatants from individual wells were screened first for whether they contained human gamma, kappa antibodies. The supernatants which were scored positive for human gamma, kappa were then subsequently screened by FACS (described above) for human anti-α5β1.

Monoclonal IgG Antibodies:

The antibody secreting hybridomas were transferred to 24 well plates, screened again and, if confirmed positive for human anti-α5β1 IgG monoclonal antibodies, were subcloned at least twice by limiting dilution. The stable subclones were then cultured in vitro to generate small amounts of antibody in tissue culture medium for further characterization. The procedures described above were used to produce several anti-α5β1 monoclonal antibodies, including antibodies designated as "22B5", "24C7", "1D9", and "2D2", which are described herein.

Example 2

Structural Characterization of Human Monoclonal Antibody 22B5

The cDNA sequences encoding the heavy and light chain variable regions of the 22B5 monoclonal antibody were obtained from the 22B5 hybridoma using standard PCR techniques and were sequenced using standard DNA sequencing techniques.

The nucleotide and amino acid sequences of the heavy chain variable region of 22B5 are shown in FIGS. 1A and 1B and in SEQ ID NOs: 11 and 7, respectively. The nucleotide and amino acid sequences of the light chain variable region of 22B5 are shown in FIGS. 1C and 1D and in SEQ ID NOs: 12 and 8, respectively.

The subclass of the original 22B5 molecule was IgG4. The IgG subclass was switched to IgG1 to provide FcγR binding and effector functions, such as ADCC. Three mutations were introduced into the IgG1 constant region (S247D, A338L, and I340E) by site-directed mutagenesis to further increase binding to FcγRs and effector function activity. 22B5 with the IgG1 subclass and containing these three mutations is referred to as "22B5/DLE" or "22B5 IgG1 DLE". Two mutations of the heavy chain variable domain were returned to germ line to minimize immunogenicity (I30S and N33S). No mutations were found in the light chain variable sequence. The heavy chain of 22B5/DLE is shown as SEQ ID NO: 9, while the light chain of 22B5/DLE is shown as SEQ ID NO: 10.

Comparison of the 22B5 heavy chain immunoglobulin sequence to the known human germline immunoglobulin heavy chain sequences demonstrated that the 22B5 heavy chain utilizes a $V_H$ segment from human germline $V_H$ 4-39, a D segment from the human germline 3-10, and a JH segment from human germline JH 6b. The alignment of the 22B5 $V_H$ sequence to the germline $V_H$ 4-39 sequence is shown in FIG. 2. Further analysis of the 22B5 $V_H$ sequence using the Kabat system of CDR region determination led to the delineation of the heavy chain CDR1, CDR2 and CD3 regions as shown in FIG. 1B, and in SEQ ID NOs: 1, 2 and 3, respectively.

Comparison of the 22B5 light chain immunoglobulin sequence to the known human germline immunoglobulin light chain sequences demonstrated that the 22B5 light chain utilizes a $V_L$ segment from human germline VK L6 and a JK segment from human germline JK 4. The alignment of the 22B5 $V_L$ sequence to the germline VK L6 sequence is shown in FIG. 2. Further analysis of the 22B5 $V_L$ sequence using the Kabat system of CDR region determination led to the delineation of the light chain CDR1, CDR2 and CD3 regions as shown in FIG. 1D, and in SEQ ID NOs: 4, 5 and 6, respectively.

Example 3

Characterization of Binding Specificity and Binding Kinetics of Human Monoclonal Antibody 22B5

In this example, binding affinity and binding kinetics of the 22B5 human anti-α5β1 antibody with the IgG1 DLE mutations (22B5/DLE) were examined by Biacore analysis. Also, binding specificity was examined by flow cytometry (FACS).

Binding Affinity and Kinetics

Binding kinetics and nominal avidity of 22B5/DLE to the extracellular domain of α5β1 was determined using Biacore analysis (Biacore AB, Uppsala, Sweden). To perform BIAcore kinetic analyses, the 22B5/DLE antibody was immobilized on a biosensor chip and various concentrations of human recombinant α5β1 extracellular domain were flowed across the surface at 25.0° C. (see FIG. 3). The binding data were fit globally to a simple one-to-one binding model with drifting baseline. 22B5/DLE binds reversibly to α5β1. The binding constant ($K_D$) to human recombinant α5β1 extracellular domain ranged from 2.7 to 4.1 nM. The $K_D$ was greater when measured in the absence of divalent cations, consistent with cation-dependent activation of integrin. The kinetic binding parameters ranged from $3.4\times10^{-5}$ to $4.5\times10^{-5}$ $M^{-1}$ $s^{-1}$ for the on-rate and from $1.2\times10^{-3}$ to $1.4\times10^{-3}$ $s^{-1}$ for the off-rate (see FIG. 3 and Table 1).

To obtain a nominal avidity measurement, human recombinant α5β1 extracellular domain was immobilized on a biosensor chip and various concentrations of 22B5/DLE were flowed across the surface at 25.0° C. A nominal avidity value was estimated to be 0.05 pM in 20 mM HEPES pH 7.4, 150 mM NaCl, 0.005% P20 with 4.0 mM $MgCl_2$.

TABLE 1

Summary of Binding and Kinetic Data Obtained from BIAcore Studies

| Affinity of 22B5/DLE for α5β1 (Biacore) | |
|---|---|
| $K_D$ ($CaCl_2$) | 2.7 nM |
| $K_D$ ($MgCl_2$) | 4.1 nM |
| On rate ($k_{on}$) ($CaCl_2$) | $4.5 \times 10^{-5}$ $M^{-1}s^{-1}$ |
| On rate ($k_{on}$) ($MgCl_2$) | $3.4 \times 10^{-5}$ $M^{-1}s^{-1}$ |
| Off rate ($k_{off}$) ($CaCl_2$) | $1.2 \times 10^{-3}$ $s^{-1}$ |
| Off rate ($k_{off}$) ($MgCl_2$) | $1.4 \times 10^{-3}$ $s^{-1}$ |
| Avidity of 22B5/DLE for α5β1 ($K_D$, Biacore) | 0.05 pM |

$CaCl_2$ refers to buffer conditions of 10 mM HEPES pH 7.4, 150 mM NaCl, 0.005% P20 with 4.0 mM $CaCl_2$; $MgCl_2$ refers to buffer conditions of 10 mM HEPES pH 7.4, 150 mM NaCl, 0.005% P20 with 4.0 mM $MgCl_2$.

Cellular Affinity for α5β1 Determination by FACS

Figure 4:
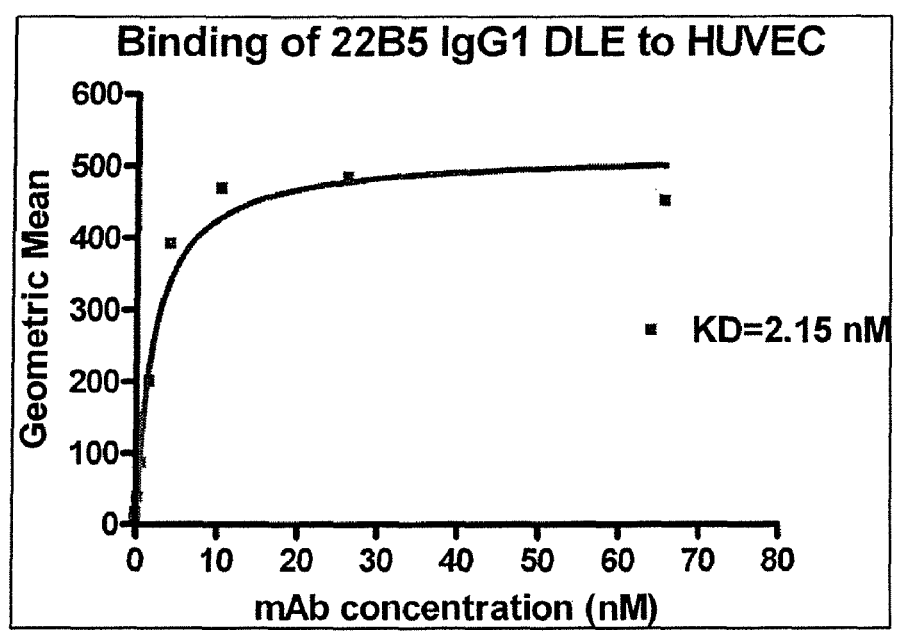
FIG. 4 shows dose-dependent binding of 22B5/DLE to HUVEC by FACS.

The 22B5/DLE antibody was tested for its binding affinity to cell surface integrin α5 using a FACS assay, employing endogenous human integrin α5β1 expressing cells (HU-VEC). Briefly, the cells were detached using trypsin-EDTA and washed with cold PBS. After being aliquoted into 96-well plates, the cells were blocked by serum and incubated with different concentrations of specific mAb for 1 hour at 4° C. Subsequently, the cells were washed and incubated with an anti-human κ secondary antibody conjugated with the R-PE fluorophore and analyzed using a FACSCalibur flow cytometer. 10,000 events were collected for each sample without applying any gating. For $K_D$ determination, the Geometric Mean of each sample histogram was calculated and plotted as a function of the mAb concentration. $K_D$ was calculated after fitting to a two-state equilibrium model. 22B5/DLE binds to endogenous α5β1 with $K_D$ of 2.15 nM (n=4) in HUVEC (see FIG. 4).

Example 4

Affinity for Fcγ Receptors by Biacore

Figure 5:
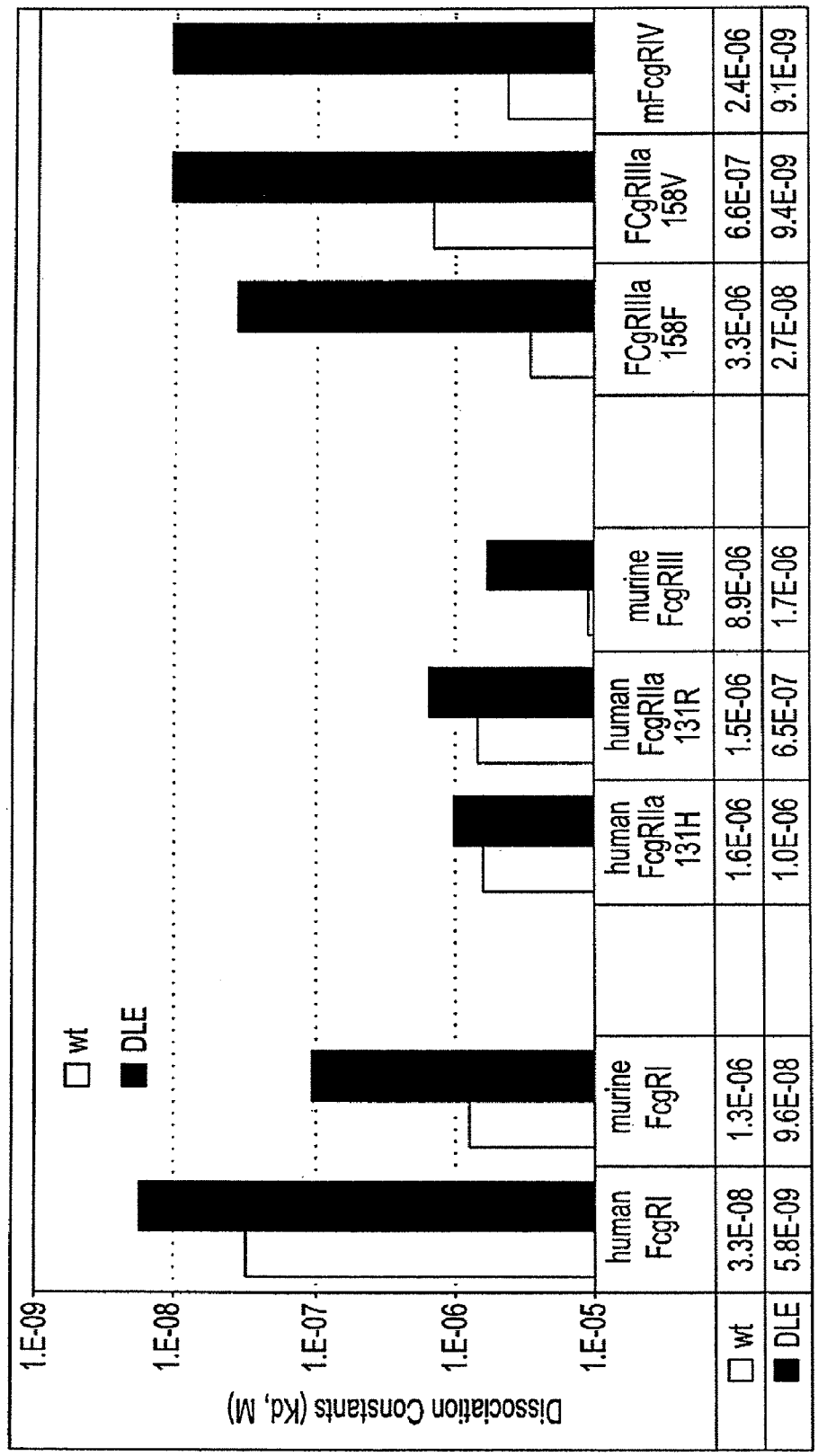
FIG. 5 shows equilibrium dissociation constants comparing human and mouse Fcγ receptors. "wt" refers to 22B5 wild type IgG1; "DLE" refers to 22B5/DLE.

The ability of 22B5/DLE, which contains the IgG1 DLE triple mutations (as discussed previously in Example 2), to enhance binding to the FcγRs was evaluated in a Biacore binding experiment. The FcγR binding affinities of 22B5/DLE were compared with the binding affinity of wild type (wt) IgG1. The three classes of FcγRs tested were: 1) the high affinity receptor FcγRI; 2) the two polymophic variants of the low affinity receptor FcγRIIa/131H and FcγRIIa/131R; and 3) the two polymorphic variants of the medium affinity receptor, FcγRIIIa/158F and FcγRIIIa/158V. The results (shown in FIG. 5, and summarized in Table 2) show an approximate 6-fold increase for the high affinity receptor FcγRI. A 122- and 70-fold enhancement for binding to the medium affinity receptor FcγRIII/158F and 158V, respectively, was observed. The binding affinity comparison of 22B5/DLE and wild type IgG1 was also evaluated against the murine Fcγ receptors. The greatest enhancement in binding was to the mFcγRIV, followed by mFcγRI, and mFcγRIII (see FIG. 5).

TABLE 2

Biacore binding to FcγRs ($K_D$, Fold enhancement over wt IgG1)

| FcγR | $K_D$ (Fold enhancement over wt IgG1) |
| --- | --- |
| Human FcγRI | 5.8 nM (6 X) |
| Human FcγRIIa/131H | 1000 nM (1.6 X) |
| Human FcγRIIa/131R | 650 nM (2.3 X) |
| Human FcγRIII/158F | 27 nM (122 X) |
| Human FcγRIII/158V | 9.4 nM (70 X) |
| Murine FcγRI | 96 nM (14 X) |
| Murine FcγRIII | 1700 nM (5 X) |
| Murine FcγRIV | 9.1 nM (260 X) |

Example 5

Cellular Functional Activity of 22B5/DLE

Cell Adhesion Blockade

Figure 6:
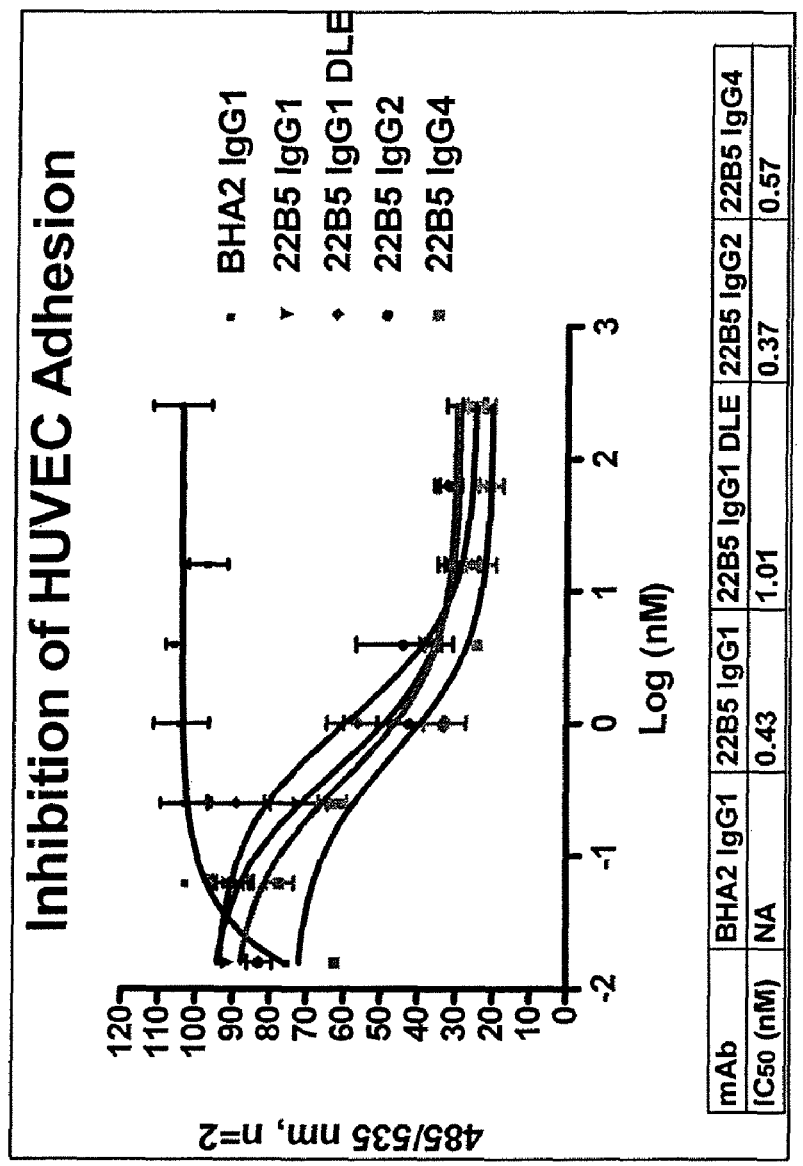
FIG. 6 shows the results of a HUVEC cellular adhesion blockade assay. The results indicate the level of inhibition of HUVEC adhesion to fibronectin for 22B5 and various subclass variants as well as the negative control (BHA2 IgG1). The calculated $IC_{50}$ values are also shown.

The ability of 22B5/DLE to interrupt integrin α5β1-mediated cell adhesion was tested. Cell adhesion assays were performed by pre-incubating HUVEC cells with an antibody (22B5/DLE, 22B5 IgG1, IgG2 and IgG4 subclass variants, or a negative control mAb (BHA2 IgG1)) and subsequently plated in fibronectin (FN) or collagen coated plates. HUVEC cells (15,000) were mixed with antibody in adhesion buffer (Hepes-buffered salt solution containing glucose and bovine serum albumin) for 20 minutes at room temperature. Cells were added to the wells of 96-well plate coated with fibronectin or collagen, and allowed to adhere to the plate for one hour at 37° C./5% $CO_2$. Non-adherent cells were removed by washing each well three times. The amount of adherent cells remaining in each well was measured. The adherent cells were lysed by the addition of a buffer containing the CyQUANT GR dye and fluorescence was measured at Ex/Em: 485/535 nm with a plate reader. As can be seen in FIG. 6, function-blocking integrin α5β1 mAbs selectively inhibit HUVEC adhesion to fibronectin, but not to collagen (negative control). As shown in FIG. 6, the $IC_{50}$ for 22B5/DLE and its subclass variants (wild type IgG1, IgG1 DLE, IgG2, and IgG4) were similar in this one-hour assay. These data demonstrate that binding of the antibody with α5 and/or α5β1 inhibits binding of the integrin with fibronectin. These data further indicate that the antibody binds α5β1 when it is expressed on the surface of the cells. That is, the epitope recognized by the antibody is available when the α5 and β1 chains are associated and the epitope is available for binding when the integrin is expressed on the cell surface.

Example 6

In-Vitro ADCC Effector Function

Figure 7:
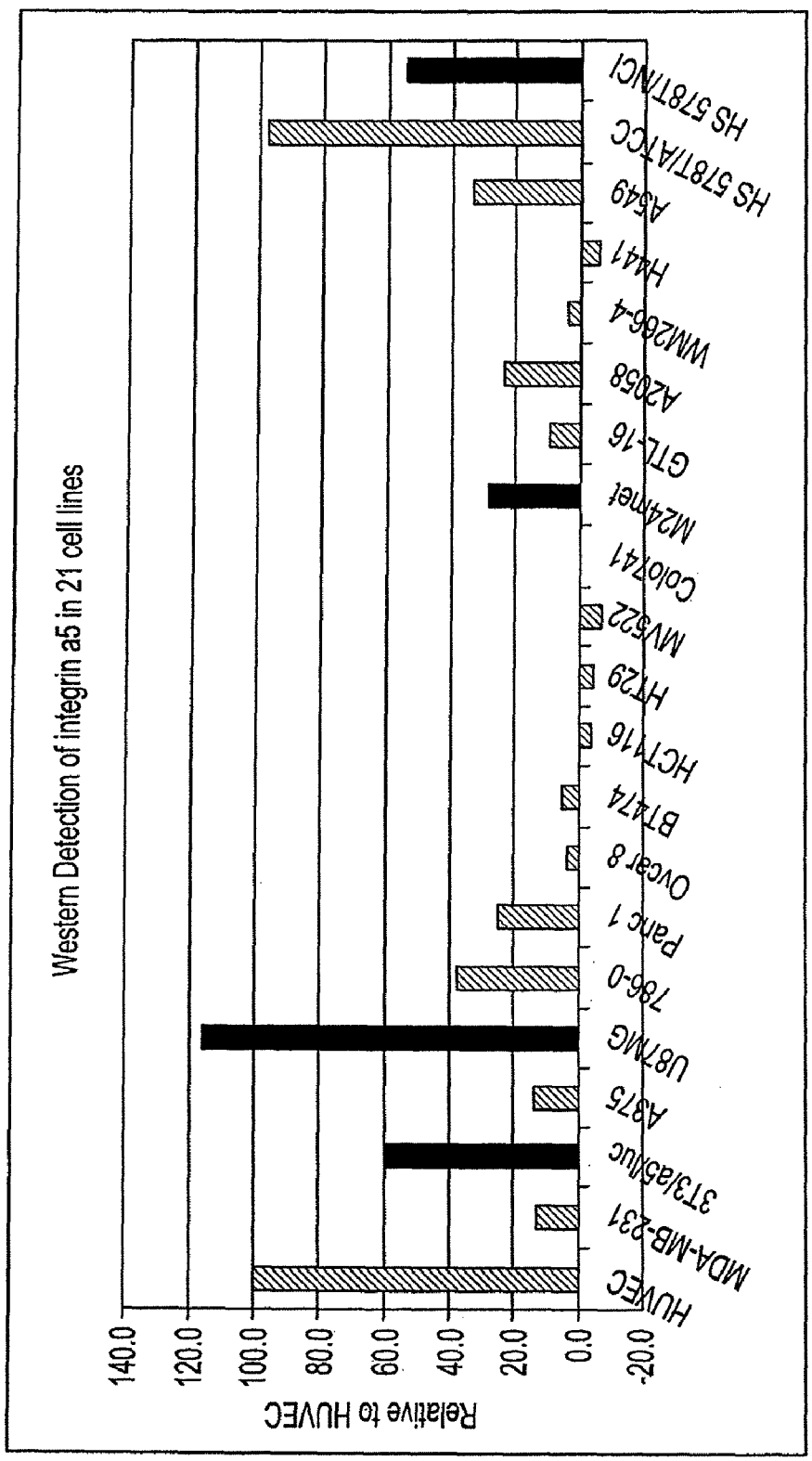
FIG. 7 shows human α5 expression from HUVEC and 20 tumor cell lines measured by Western Blotting.

Effector function activities were assessed through ADCC assays in the presence of human peripheral blood mononuclear cells (PBMCs) against α5β1-positive target cells using standard methods. Integrin α5 expression levels across a range of cell lines were measured by Western blot analysis, as follows. Cells were lysed in RIPA Lysis Buffer (Upstate) containing protease (Roche) and phosphatase inhibitors (Calbiochem). Lysates (3 μg of total protein each) were electrophoresed on SDS-PAGE gel and immunoblotted with anti-integrin α5 antibodies. Immunoreative bands were identified and analyzed by Odyssey Infrared Imaging System from LI-COR Bioscience. An example of the range of expression is shown in FIG. 7.

To measure ADCC, effector cells (PBMCs) were isolated using Ficoll gradient centrifugation from San Diego Blood Bank samples, according to standard methods. Ten thousand target cells (HUVEC or tumor lines) were pre-incubated with antibody in growth medium at room temperature for 20 minutes, then one million human PBMCs (E:T=100:1) were added, and the mixture was incubated at 37° C./5% $CO_2$ for 4 hours. ADCC mediated cell lysis was measured using lactate dehydrogenase (LDH) release detection (Roche) or ToxiLight BioAssay Kit (Cambrex), following standard protocols.

Figure 8A:
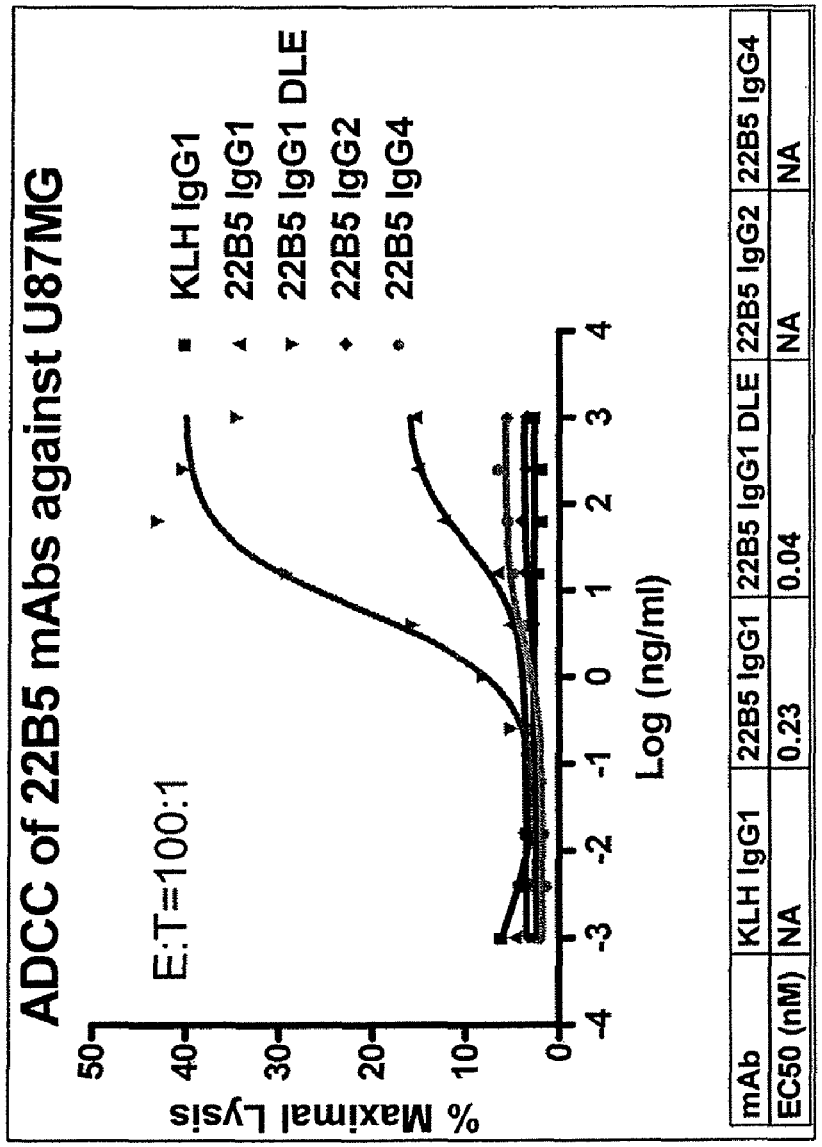
FIG. 8A shows a LDH-based detection assay measuring ADCC of U87MG cells in the presence of human PBMCs by 22B5/DLE and 22B5 wt IgG1.
Figure 8B:
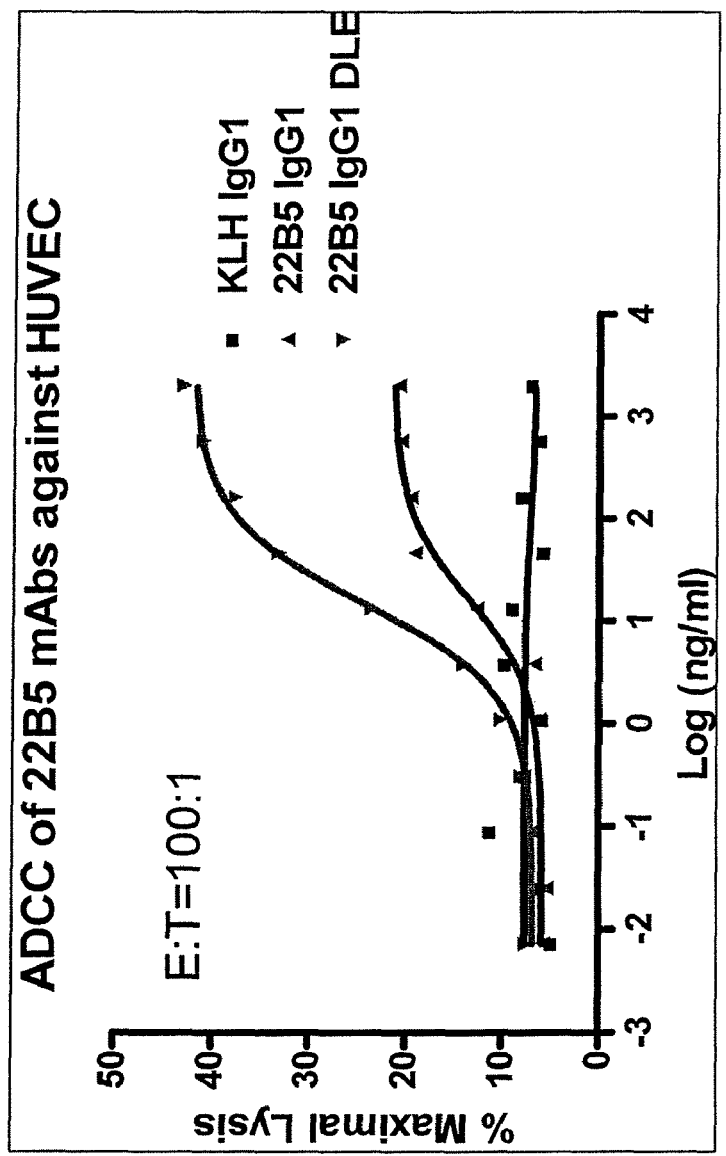
FIG. 8B shows a ToxiLight-based detection assay measuring ADCC of HUVECs in the presence of human PBMCs by 22B5/DLE and 22B5 wt IgG1.

22B5/DLE binds to tumor or endothelial-expressed integrin α5β1 and promotes ADCC (up to 80% target cell lysis) with an $EC_{50}$ of 0.04 nM compared with 0.23 nM for wt 22B5 IgG1. These data indicate that the DLE mutation enhanced ADCC activity compared with wild type IgG1. No ADCC was observed for either 2285 IgG2 or 22B5 IgG4 in the four-hour assay. KLH IgG1 was used as a negative control mAb. Examples of ADCC in HUVEC and a representative tumor line (U87MG) are shown in FIG. 8 (representatives of both detection methods).

Figure 9:
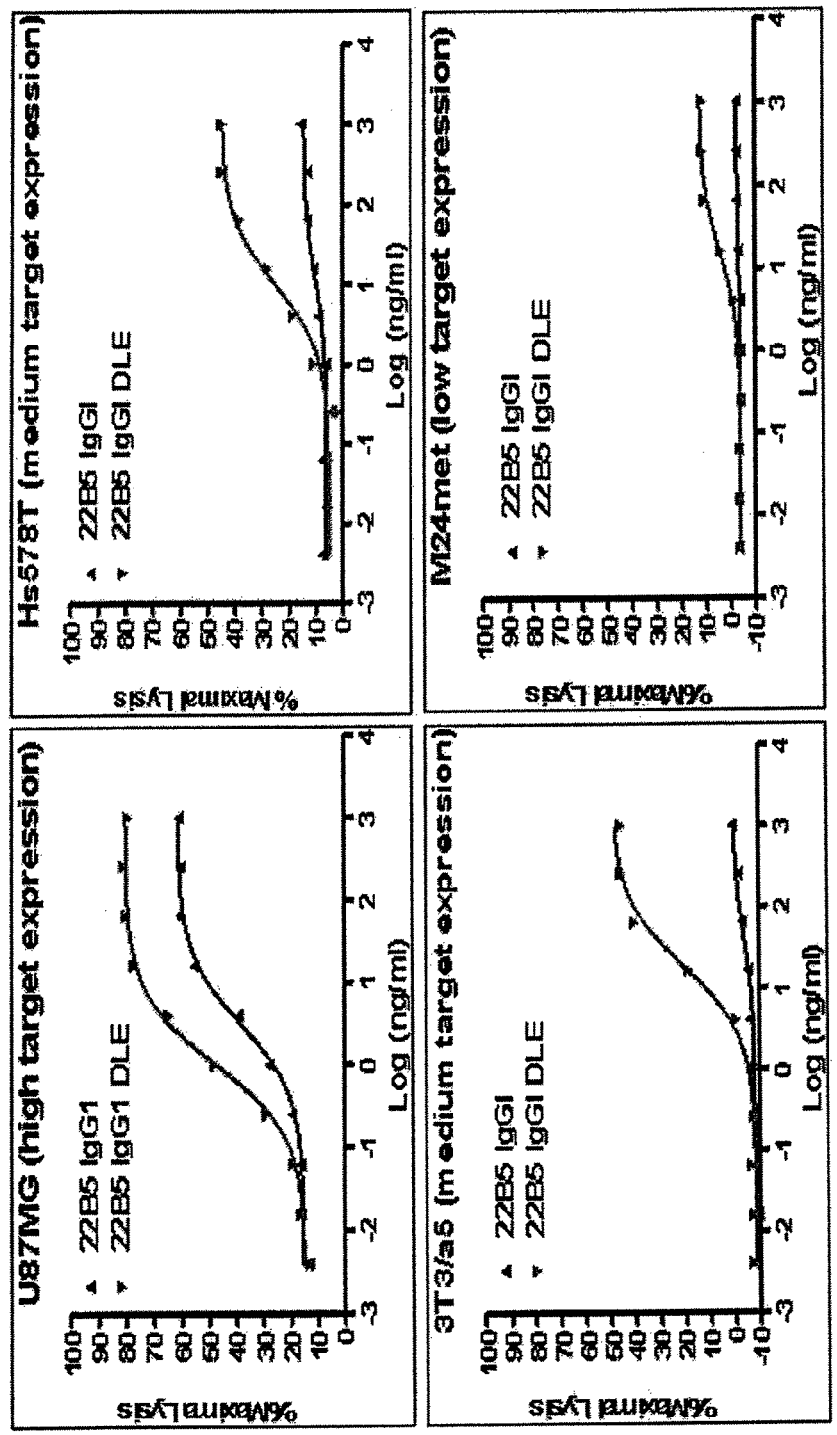
FIG. 9 shows LDH-based detection assays that indicate substantial ADCC enhancement from 22B5/DLE over wt 22B5 IgG1 across a broad range of antigen expression levels.

The cellular cytotoxicity induced by 22B5/DLE and wt 22B5 IgG1 correlates with the level of α5β1-expression by the cell line, as shown by the data provided in FIG. 9. The cells with highest expression of α5β1 (panel A, U87MG) demonstrated the highest level of cell toxicity, while the cell lines with medium expression (FIG. 9, Hs578T and 3T3,α5) demonstrated intermediate cytotoxicity. Notably, 22B5/DLE enhanced the ADCC effects in M24met cells, which expressed low level of α5β1 (examples in the lower panel of FIG. 9). These data demonstrate that ADCC is mediated, at least in part, by antibody binding with α5β1 expressed by the cell.

Example 7

In Vivo Anti-Metastatic Efficacy

In addition to its pro-proliferation, pro-migration and pro-survival activities in endothelial and tumor cells, integrin α5β1 is also implicated in tumor metastasis by promoting tumor cell extravasation and migration to distant organs. The following study aimed to demonstrate anti-metastatic efficacy of 22B5/DLE in a preclinical model.

Inhibition of A549-Luc Experimental Metastasis to the Lung

A549-Luc is a human non-small cell lung cancer (NSCLC) cell line transfected with the luciferase gene. When implanted intravenously, it preferably localizes in the lung, which can be measured by bioluminescence imaging (BLI). In this study, A549-Luc cells were injected ($3 \times 10^6$ per animal) via tail vein in SCID BALB/c mice that had received a pre-dose of the relevant antibody two days prior to the injection. Following implantation, animals were dosed once a week until week 8. Bioluminescence of individual animals was measured once a week until week 20.

Figure 10A:
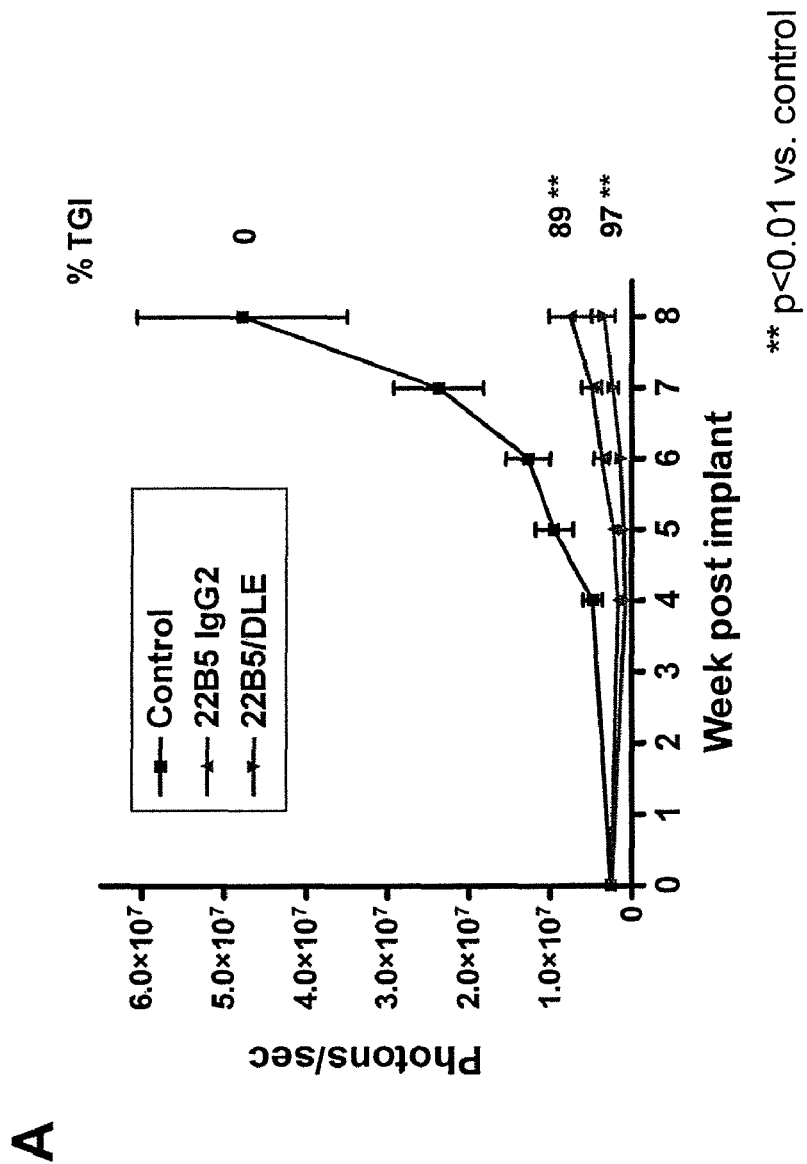
FIG. 10A: Lung metastasis volume measured by BLI at week 8 (n=11 for the control group, n=14 for the 22B5 IgG2 group and n=12 for the 22B5/DLE group).

22B5/DLE exhibited superior anti-tumor metastasis efficacy with a TGI (tumor growth inhibition) of 97% at week 8 (final week of dosing), which is statistically significant ($p<0.01$) compared with the control group. Dosing with 22B5 IgG2, which is not expected to mediate ADCC in this model, also achieved a significant TGI of 89% at week 8 (FIG. 10A). The p values of the comparison between 22B5/DLE and 22B5 IgG2 at weeks 5, 6, 7, and 8 were 0.07, 0.03, 0.08 and 0.17, respectively. All treatments were stopped after week 8 while daily monitoring for adverse physiological signs and weekly measurements by BLI of the animals were continued.

Figure 10B:
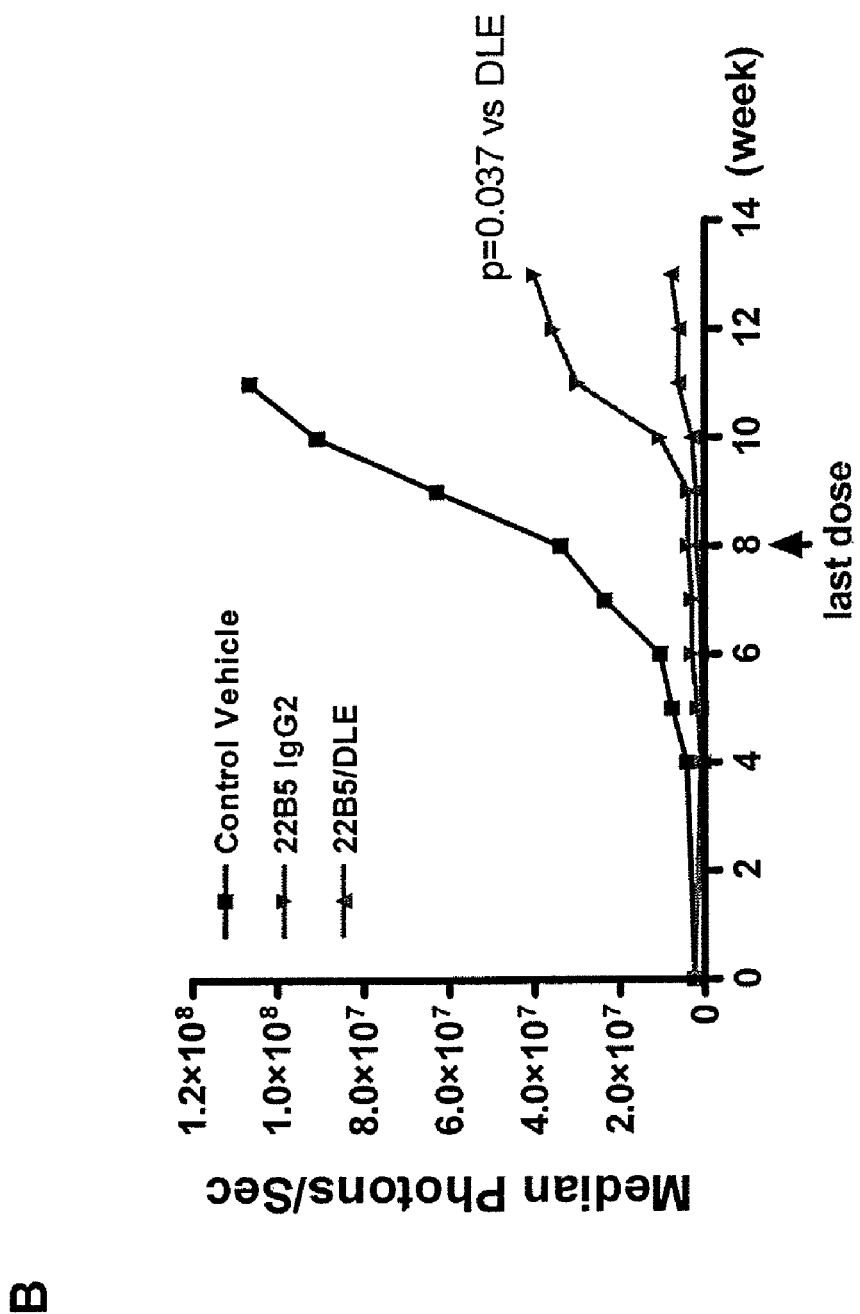
FIG. 10B: Regrowth of lung tumors in the 22B5 IgG2 treated group after dosing was stopped. By comparison, the 22B5/DLE treated group showed little regrowth.
Figure 10C:
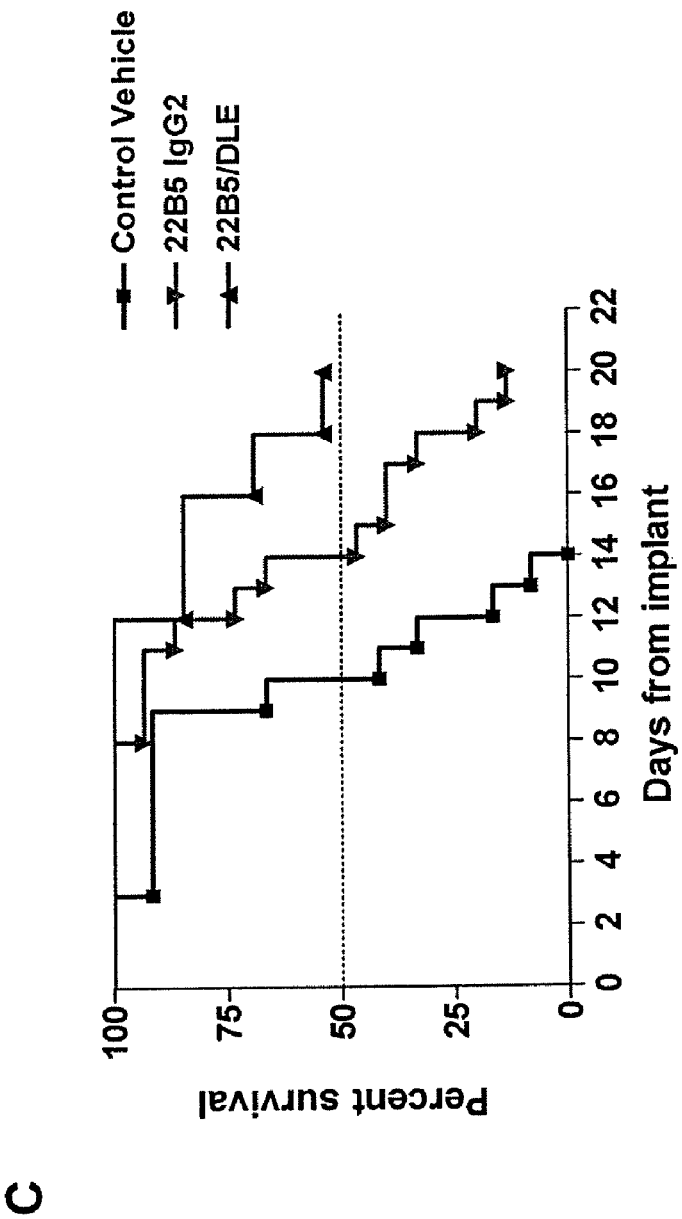
FIG. 10C: Kaplan-Meier Plot of animal survival rate of each treatment group (endpoint=BLI $1\times10^8$ photons/second), $p<0.0001$ for control vehicle group comparing to all other groups, and $p<0.05$ for comparison between 22B5/DLE and 22B5 IgG2 groups.

Tumors in the 22B5/DLE treated group remained suppressed through week 13, whereas those in 22B5 IgG2 treated group began to grow rapidly approximately 2 weeks after dosing cessation (FIG. 10B). The study end point was considered reached when tumor BLI reached $1 \times 10^8$ photons/second, at which time the mice were sacrificed. The Kaplan-Meier plot (FIG. 10C) shows that 22B5/DLE significantly extended the median survival time of the animals to 20 weeks compared with 14 weeks for 22B5 IgG2 treated animals and 10 weeks for the control group.

These data demonstrate that in this model, the anti-tumor effect of 22B5 is not mediated exclusively by ADCC. That is, 22B5-IgG2 inhibited tumor growth/invasion even though human IgG2 is not known to mediate effector functions, including cell cytotoxicity, and yet the antibody mediated anti-tumor effects. Further, the data demonstrated that tumor growth remained suppressed after administration of 22B5-IgG1-DLE was stopped. These data show that blocking of α5β1 binding with FN mediates an anti-tumor effect (22B5-IgG2) which is further enhanced by ADCC (22B5-IgG1/DLE).

Example 8

Structural Characterization of Human Monoclonal Antibodies 24C7, 1D9, and 2D2

The cDNA sequences encoding the heavy and light chain variable regions of the 24C7, 1D9, and 2D2 monoclonal antibodies were obtained from the 24C7, 1D9, and 2D2 (respectively) hybridomas using standard PCR techniques and were sequenced using standard DNA sequencing techniques.

The nucleotide and amino acid sequences of the heavy chain variable region of 24C7 are shown in FIGS. 1E and 1F and in SEQ ID NOs: 21 and 19, respectively. The nucleotide and amino acid sequences of the light chain variable region of 24C7 are shown in FIGS. 1G and 1H and in SEQ ID NOs: 22 and 20, respectively.

The nucleotide and amino acid sequences of the heavy chain variable region of 1D9 are shown in FIGS. 1I and 1J and in SEQ ID NOs: 31 and 29, respectively. The nucleotide and amino acid sequences of the light chain variable region of 1D9 are shown in FIGS. 1K and 1L and in SEQ ID NOs: 32 and 30, respectively.

The nucleotide and amino acid sequences of the heavy chain variable region of 2D2 are shown in FIGS. 1M and 1N and in SEQ ID NOs: 41 and 39, respectively. The nucleotide and amino acid sequences of the light chain variable region of 1D9 are shown in FIGS. 1O and 1P and in SEQ ID NOs: 42 and 40, respectively.

The subclass of the original 24C7, 1D9, and 2D2 molecules was IgG1. For the IgG1 subclass, three mutations were introduced into the IgG1 constant region (S247D, A338L, and I340E) by site-directed mutagenesis to further increase binding to FcγRs and effector function activity. Thus, 24C7 with the IgG1 subclass and containing these three mutations is referred to as "24C7/DLE" or "24C7 IgG1 DLE". Similarly, analogous antibodies with these three mutations are referred to herein as "1D9/DLE" or "1D9 IgG1 DLE", and "2D2/DLE" or "2D2 IgG1 DLE". Similarly, antibodies with the two mutations S247D and I340E are referred to herein as "DE" mutants, e.g. "24C7/DE", or "24C7 IgG1 DE". Similar designations for any of the antibodies as described herein and with any one, two, or three of the mutations mentioned above, are referred to in a similar manner. For example, "1D9/DE" refers to the 1D9 antibody as described herein, with an IgG1 subclass with the following mutations in the Fc region—S247D and I340E. Similarly, "2D2/L" would refer to the 2D2 antibody as described herein, with an IgG1 isotype and containing the A338L mutation, and so forth.

Comparison of the 24C7 heavy chain immunoglobulin sequence to the known human germline immunoglobulin heavy chain sequences demonstrated that the 24C7 heavy chain utilizes a $V_H$ segment from human germline $V_H$ 3-30.3, a D segment from the human germline 7-27, and a JH segment from human germline JH 6b. Analysis of the 24C7 $V_H$ sequence using the Kabat system of CDR region determination led to the delineation of the heavy chain CDR1, CDR2 and CD3 regions as shown in FIG. 1F, and in SEQ ID NOs: 13, 14 and 15, respectively.

Comparison of the 24C7 light chain immunoglobulin sequence to the known human germline immunoglobulin light chain sequences demonstrated that the 24C7 light chain utilizes a $V_L$ segment from human germline VK L6 and a JK segment from human germline JK 2. Analysis of the 24C7 $V_L$ sequence using the Kabat system of CDR region determination led to the delineation of the light chain CDR1, CDR2 and CD3 regions as shown in FIG. 1H, and in SEQ ID NOs: 16, 17 and 18, respectively.

Comparison of the 1D9 heavy chain immunoglobulin sequence to the known human germline immunoglobulin heavy chain sequences demonstrated that the 1D9 heavy chain utilizes a $V_H$ segment from human germline $V_H$ 3-30.3, and a JH segment from human germline JH 6b. The D segment could not be assigned a germline gene because of extensive mutations. Analysis of the 1D9 $V_H$ sequence using the Kabat system of CDR region determination led to the delineation of the heavy chain CDR1, CDR2 and CD3 regions as shown in FIG. 1J, and in SEQ ID NOs: 23, 24 and 25, respectively.

Comparison of the 1D9 light chain immunoglobulin sequence to the known human germline immunoglobulin light chain sequences demonstrated that the 1D9 light chain utilizes a $V_L$ segment from human germline VK L6 and a JK segment from human germline JK 1. Analysis of 1D9 $V_L$ sequence using the Kabat system of CDR region determination led to the delineation of the light chain CDR1, CDR2 and CD3 regions as shown in FIG. 1L, and in SEQ ID NOs: 26, 27 and 28, respectively.

Comparison of the 2D2 heavy chain immunoglobulin sequence to the known human germline immunoglobulin heavy chain sequences demonstrated that the 2D2 heavy chain utilizes a $V_H$ segment from human germline $V_H$ 3-30.3, a D segment from the human germline 7-27, and a JH segment from human germline JH 6b. Analysis of the 2D2 $V_H$ sequence using the Kabat system of CDR region determination led to the delineation of the heavy chain CDR1, CDR2 and CD3 regions as shown in FIG. 1N, and in SEQ ID NOs: 33, 34 and 35, respectively.

Comparison of the 2D2 light chain immunoglobulin sequence to the known human germline immunoglobulin light chain sequences demonstrated that the 2D2 light chain utilizes a $V_L$ segment from human germline VK L6 and a JK segment from human germline JK 3. Analysis of the 2D2 $V_L$ sequence using the Kabat system of CDR region determination led to the delineation of the light chain CDR1, CDR2 and CD3 regions as shown in FIG. 1P, and in SEQ ID NOs: 36, 37 and 38, respectively. A table showing the gene utilization for antibodies 22B5, 2D2, 24C7, and 1D9 monoclonal antibodies is shown below as Table 3.

TABLE 3

| | Gene Utilization | | | | |
|---|---|---|---|---|---|
| | Heavy Chain | | | Light Chain | |
| Antibody | VH | D | JH | VK | JK |
| 22B5 | 4-39 | 3-10 | JH 6b | Vk L6 | JK 4 |
| 2D2 | 3-30.3 | 7-27 | JH 6b | Vk L6 | JK 3 |
| 24C7 | 3-30.3 | 7-27 | JH 6b | Vk L6 | JK 2 |
| 1D9 | 3-30.3 | Not determined | JH 6b | Vk L6 | JK 1 |

Example 9

Characterization of Binding Specificity and Binding Kinetics of Human Monoclonal Antibodies 22B5, 24C7, 1D9, and 2D2

In this example, binding specificity of the 22B5, 24C7, 1D9, and 2D2 human anti-α5β1 antibodies of IgG1 subclass—with and without the IgG1 DLE mutations (i.e. "22B5 G1 DLE", "22B5 G1", "1D9 G1 DLE", "1D9 G1" etc.) was examined by flow cytometry using fluorescence activated cell sorting (FACS).

Cellular Affinity for α5β1 Determination by FACS

Figure 11A:
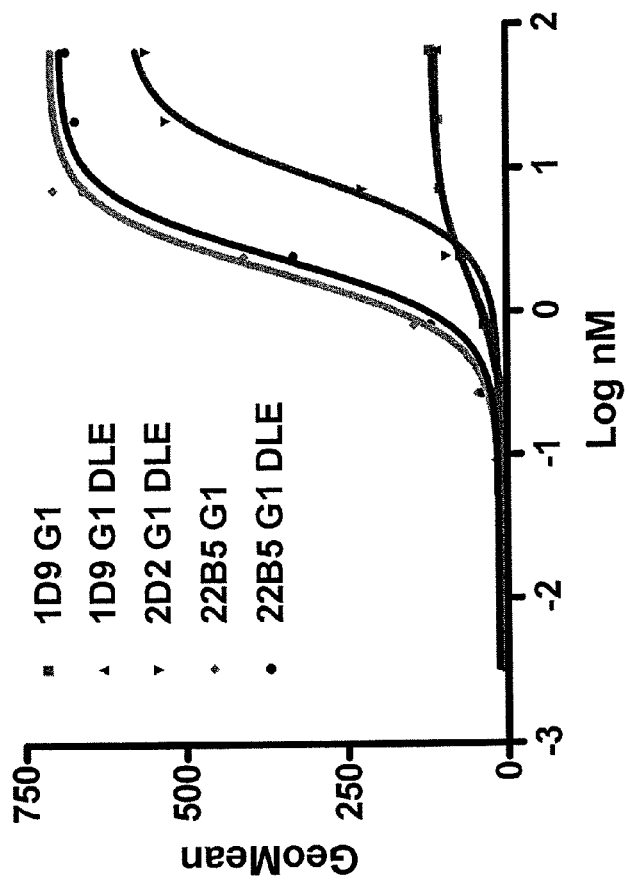
FIGS. 11A and 11B show dose-dependent binding of 1D9, 1D9/DLE, 24C7/DLE, 2D2/DLE, 22B5, and 22B5/DLE to HUVEC by FACS.
Figure 11B:
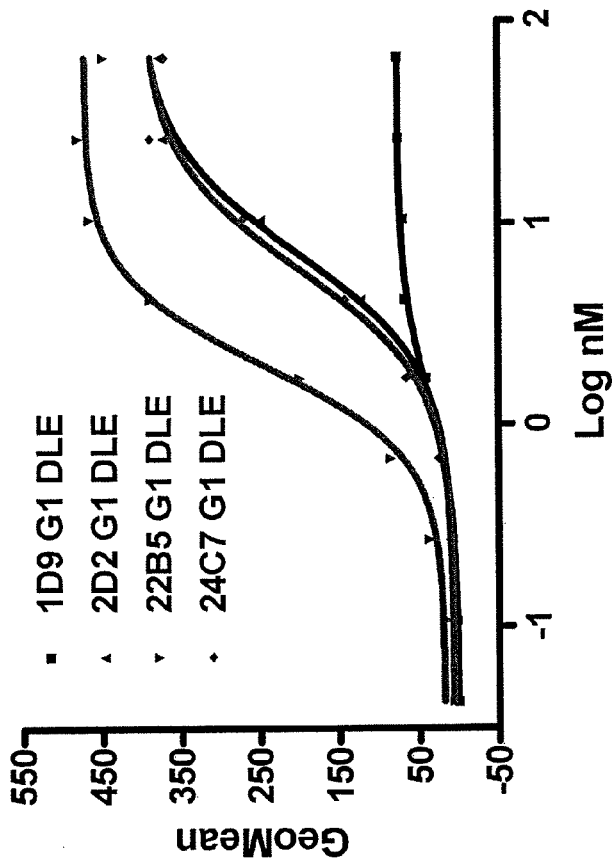

The 22B5/DLE, 24C7/DLE, 1D9/DLE, and 2D2/DLE antibodies were tested for their binding affinity to cell surface integrin α5 using a FACS assay, employing endogenous human integrin α5β1 expressing cells (HUVEC). Briefly, the cells were detached using trypsin-EDTA and washed with cold PBS. After being aliquoted into 96-well plates, the cells were blocked by serum and incubated with different concentrations of specific mAb for 1 hour at 4° C. Subsequently, the cells were washed and incubated with an anti-human κ secondary antibody conjugated with the R-PE fluorophore and analyzed using a FACSCalibur flow cytometer. 10,000 events were collected for each sample without applying any gating. For $K_D$ determination, the Geometric Mean of each sample histogram was calculated and plotted as a function of the mAb concentration. $K_D$ was calculated after fitting to a two-state equilibrium model. Results are shown in FIGS. 11A and 11B.

Example 10

In vitro ADCC Effector Function of Human Monoclonal Antibodies 22B5, 24C7, 1D9, and 2D2

Figure 12:
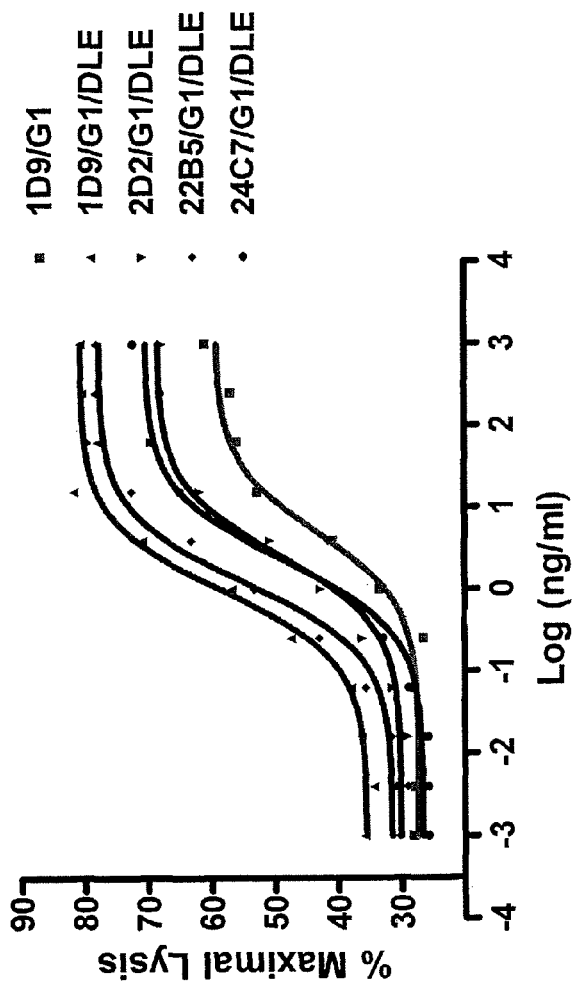
FIG. 12 shows in-vitro ADCC induced by 1D9, 1D9/DLE, 2D2/DLE, 22B5/DLE, and 24C7/DLE.

Effector function activities were assessed through antibody-dependent cell-mediated cytotoxicity (ADCC) assays as described previously in Example 6. $EC_{50}$ values for promoting ADCC (up to 80% target cell lysis) in a representative tumor line (U87MG) are shown in FIG. 12 for the antibodies 1D9, 1D9/DLE, 2D2/DLE, 22B5/DLE, and 24C7/DLE.

Example 11

In Vivo ADCC-Dependent Anti-Tumor Efficacy in a Syngeneic Model of Metastatic Melanoma To demonstrate an ADCC specific response the human monoclonal antibody 1D9/DLE (which binds to human and murine α5β1 but does not functionally neutralize α5β1) was tested in a tumor growth inhibition (TGI) model in syngenic mice with intact immune effector cells. Specifically, ADCC-mediated anti-tumor activity was evaluated in a syngeneic mouse model in which murine melanoma B16F10 cells expressed α5β1. Integrin α5-expressing mouse melanoma line B16F10 is highly metastatic and primarily colonizes to the lung once injected intravenously. The tumor cells were injected intravenously into immune-competent C57BL/6 mice. B16F10 cells ($2 \times 10^5$ per animal) were injected via tail vein into the syngeneic host C57BL/6 mice pre-dosed with antibodies (10 mg/kg, n=10 per group) 1 day prior to injection. The animals were dosed subcutaneously with antibody once a week for a total of 3 weeks. The animals were sacrificed and the lungs were resected at day 21.

Figure 13:
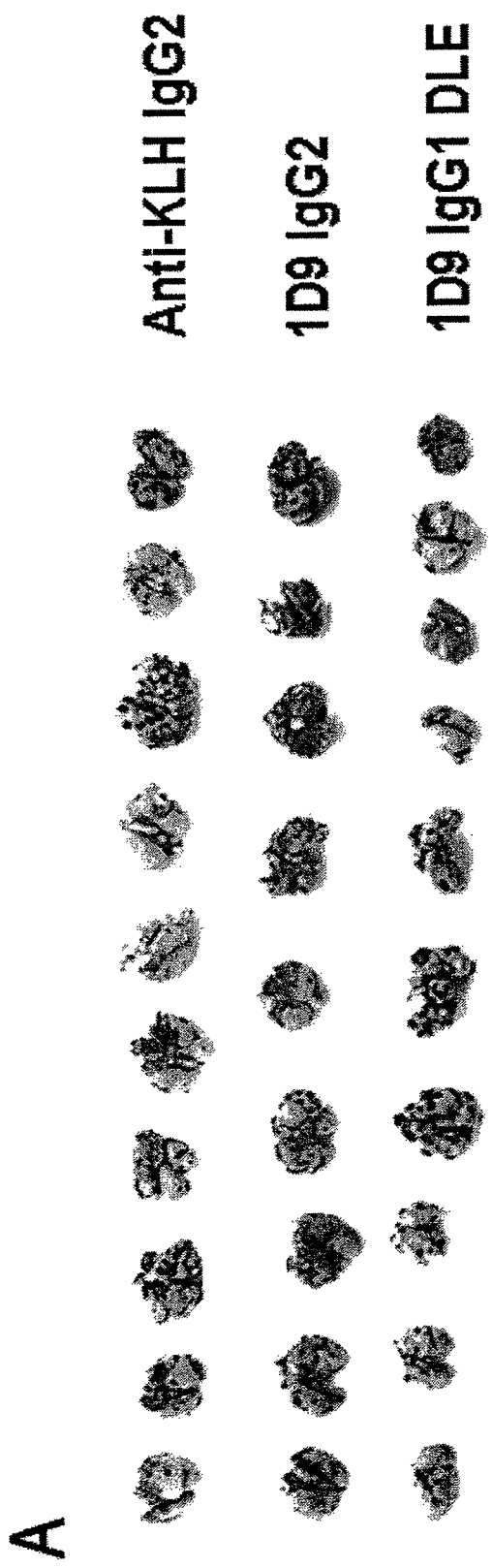
FIG. 13 shows ADCC-dependent anti-tumor efficacy of 1D9/DLE in a syngeneic model of metastatic melanoma.
Figure 13:
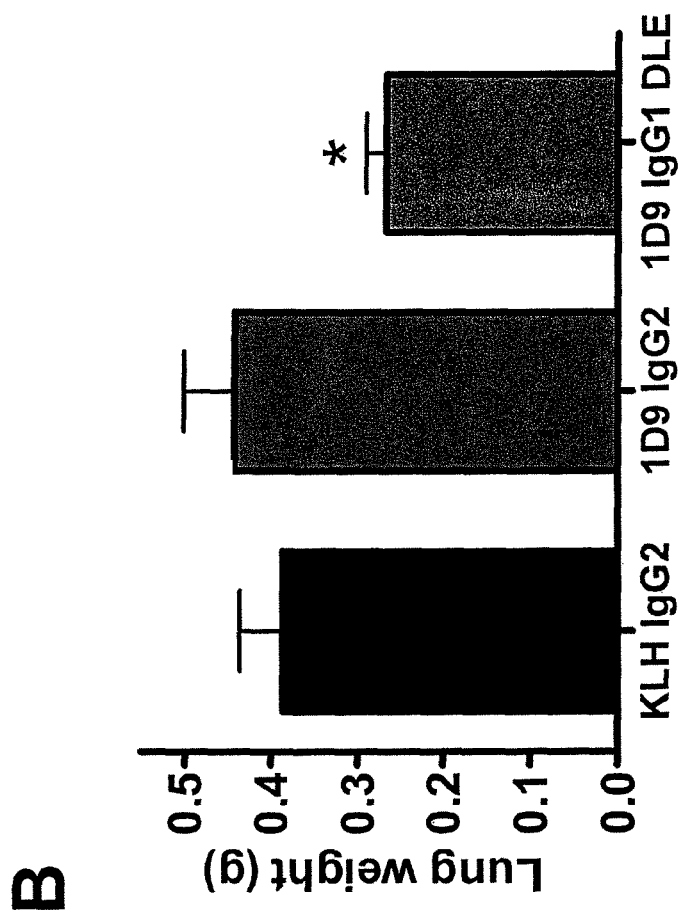
Figure 13:
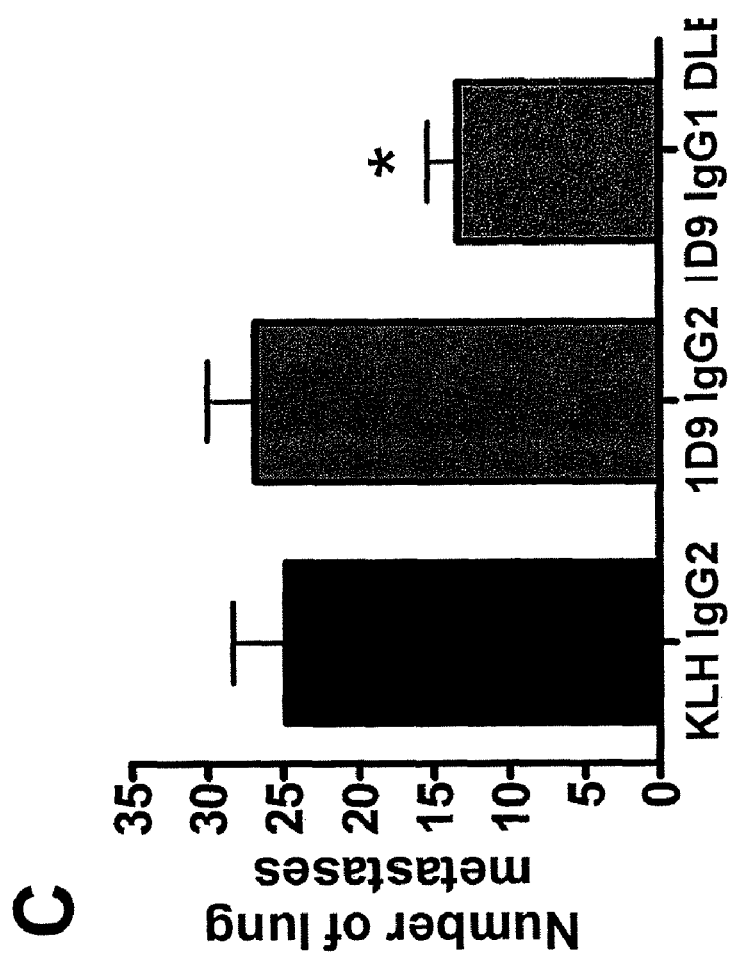

As shown by the results in FIG. 13, the 1D9/DLE antibody produced significant in vivo anti-tumor efficacy indicating that an ADCC response alone is sufficient to produce TGI. To delineate the specific impact of ADCC in the model, animals were treated with 1D9 IgG2 (not known to mediate ADCC) and 1D9 IgG1 DLE (IgG1 isotype with Fc enhancement by virtue of the DLE mutations). A greater anti-tumor efficacy was observed with 1D9 IgG1 DLE than with 1D9 IgG2. Because the isotype pairs have identical amino acid sequences in the antigen binding domain and in vitro activities, the data show that enhanced ADCC as a result of DLE mutations was responsible for the superior efficacy of 1D9 IgG1 DLE.

Deposit Information

Applicants have deposited the heavy and light chain variable regions of the antibody designated as 22B5 herein with the American Type Culture Collection (ATCC) Manassas, Va. 20110-2209 U.S.A. The 22B5 VH region was deposited on Jul. 16, 2008, and was assigned ATCC Deposit No. PTA-9377. The 22B5 VL region was deposited on Jul. 16, 2008, and was assigned ATCC Deposit No. PTA-9377. These deposits were made under the provisions of the Budapest Treaty on the International Recognition of the Deposit of Microorganisms for the Purpose of Patent Procedure and the Regulations thereunder (Budapest Treaty). These deposits will be maintained without restriction in the ATCC depository for a period of 30 years, or 5 years after the most recent request, or for the effective life of the patent, whichever is longer, and will be replaced if the deposits become non-viable during that period. Availability of the deposited materials is not to be construed as a license to practice any aspects of the present disclosure in contravention of the rights granted under the authority of any government in accordance with its patent laws. The foregoing written specification is considered to be sufficient to enable one skilled in the art to practice all aspects of the present disclosure. The present disclosure is not to be limited in scope by the materials deposited since the deposited embodiment is intended as a single illustration of certain aspects of the disclosure and any constructs that are functionally equivalent are within the scope of this disclosure. The deposit of material herein does not constitute an admission that the written description herein is inadequate to enable the practice of any aspect of the disclosure, including the best mode thereof, nor is it to be construed as limiting the scope of the claims to the specific illustrations that it represents. Indeed, various modifications of the disclosure in addition to those shown and described herein will become apparent to those skilled in the art from the foregoing description and fall within the scope of the appended claims.

SUMMARY OF SEQUENCE LISTING

| SEQ ID NO: | SEQUENCE |
|---|---|
| 1 | $V_H$ CDR1 a.a. 22B5 |
| 2 | $V_H$ CDR2 a.a. 22B5 |
| 3 | $V_H$ CDR3 a.a. 22B5 |
| 4 | $V_L$ CDR1 a.a. 22B5 |
| 5 | $V_L$ CDR2 a.a. 22B5 |
| 6 | $V_L$ CDR3 a.a. 22B5 |
| 7 | $V_H$ a.a. 22B5 |
| 8 | $V_L$ a.a. 22B5 |
| 9 | Heavy a.a. 22B5/DLE |
| 10 | Light a.a. 22B5 |
| 11 | $V_H$ n.a. 22B5 |
| 12 | $V_L$ n.a. 22B5 |
| 13 | $V_H$ CDR1 a.a. 24C7 |
| 14 | $V_H$ CDR2 a.a. 24C7 |
| 15 | $V_H$ CDR3 a.a. 24C7 |
| 16 | $V_L$ CDR1 a.a. 24C7 |
| 17 | $V_L$ CDR2 a.a. 24C7 |
| 18 | $V_L$ CDR3 a.a. 24C7 |
| 19 | $V_H$ a.a. 24C7 |
| 20 | $V_L$ a.a. 24C7 |
| 21 | $V_H$ n.a. 24C7 |
| 22 | $V_L$ n.a. 24C7 |
| 23 | $V_H$ CDR1 a.a. 1D9 |
| 24 | $V_H$ CDR2 a.a. 1D9 |
| 25 | $V_H$ CDR3 a.a. 1D9 |
| 26 | $V_L$ CDR1 a.a. 1D9 |
| 27 | $V_L$ CDR2 a.a. 1D9 |
| 28 | $V_L$ CDR3 a.a. 1D9 |
| 29 | $V_H$ a.a. 1D9 |
| 30 | $V_L$ a.a. 1D9 |
| 31 | $V_H$ n.a. 1D9 |
| 32 | $V_L$ n.a. 1D9 |
| 33 | $V_H$ CDR1 a.a. 2D2 |
| 34 | $V_H$ CDR2 a.a. 2D2 |
| 35 | $V_H$ CDR3 a.a. 2D2 |
| 36 | $V_L$ CDR1 a.a. 2D2 |
| 37 | $V_L$ CDR2 a.a. 2D2 |
| 38 | $V_L$ CDR3 a.a. 2D2 |
| 39 | $V_H$ a.a. 2D2 |
| 40 | $V_L$ a.a. 2D2 |
| 41 | $V_H$ n.a. 2D2 |
| 42 | $V_L$ n.a. 2D2 |
| 43 | IgG1 a.a. heavy chain constant regions with A247D, A338L, and I340E mutations |
| 44 | IgG1 a.a. light chain constant region |

(a.a. = amino acid; n.a. = nucleic acid)

We claim:

1. An isolated nucleic acid molecule encoding an antibody, or antigen-binding portion thereof, that binds to human integrin α5β1, wherein said antibody or antigen-binding portion comprises:
   (a) a heavy chain CDR1 as set forth in SEQ ID NO:1;
   (b) a heavy chain CDR2 as set forth in SEQ ID NO:2;
   (c) a heavy chain CDR3 as set forth in SEQ ID NO:3;
   (d) a light chain CDR1 as set forth in SEQ ID NO:4;
   (e) a light chain CDR2 as set forth in SEQ ID NO:5; and
   (f) a light chain CDR3 as set forth in SEQ ID NO:6.

2. The nucleic acid molecule of claim 1, wherein said antibody or antigen-binding portion comprises a heavy chain variable region amino acid sequence as set forth in SEQ ID NO:7.

3. The nucleic acid molecule of claim 1, wherein said antibody or antigen-binding portion comprises a light chain variable region amino acid sequence as set forth in SEQ ID NO:8.

4. The nucleic acid molecule of claim 1, wherein said antibody or antigen-binding portion comprises a heavy chain variable region amino acid sequence as set forth in SEQ ID NO:7; and a light chain variable region amino acid sequence as set forth in SEQ ID NO:8.

5. The nucleic acid molecule of claim 1, wherein said antibody comprises a heavy chain amino acid sequence as set forth in SEQ ID NO:9; and a light chain amino acid sequence as set forth in SEQ ID NO:10.

6. An isolated vector comprising the nucleic acid molecule of claim 1.

7. An isolated host cell transformed with the vector of claim 6.

8. A method for preparing an anti-α5β1 antibody or antigen-binding portion thereof, comprising culturing the host cell of claim 7 under conditions that result in production of the antibody or antigen-binding portion, and isolating the antibody or antigen-binding portion from the host cell or culture.

* * * * *